Figure 1:
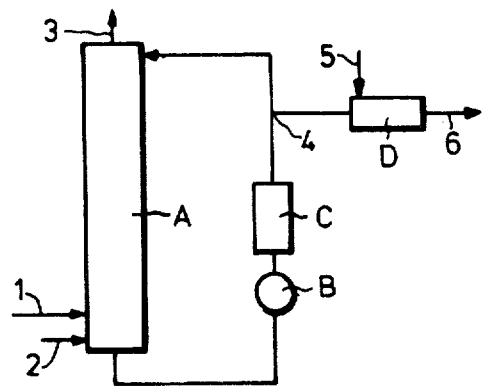

United States Patent [19]

Wagner

[11] 4,379,862

[45] Apr. 12, 1983

[54] PROCESS FOR THE PREPARATION OF POLYURETHANE RESINS USING LOW MOLECULAR WEIGHT POLYHYDROXYL COMPOUNDS PREPARED BY THE CONDENSATION OF FORMALDEHYDE

[75] Inventor: Kuno Wagner, Leverkusen, Fed. Rep. of Germany

[73] Assignee: Bayer Aktiengesellschaft, Leverkusen, Fed. Rep. of Germany

[21] Appl. No.: 282,219

[22] Filed: Jul. 10, 1981

Related U.S. Application Data

[62] Division of Ser. No. 122,931, Feb. 20, 1980, Pat. No. 4,301,310, which is a division of Ser. No. 829,173, Aug. 30, 1977, Pat. No. 4,219,508.

[30] Foreign Application Priority Data

May 11, 1977 [DE] Fed. Rep. of Germany ....... 2721186

[51] Int. Cl.$^3$ .............................................. C08G 18/14
[52] U.S. Cl. .................................... 521/158; 521/170; 528/76; 528/80; 528/85

[58] Field of Search ................. 521/158, 170; 528/85, 528/76, 80

[56] References Cited

U.S. PATENT DOCUMENTS

| | | | |
|---|---|---|---|
| 4,205,138 | 5/1980 | Müller et al. | 521/158 |
| 4,221,876 | 9/1980 | Wagner | 521/158 |
| 4,247,654 | 1/1981 | Wagner | 521/158 |
| 4,288,566 | 9/1981 | Müller et al. | 521/158 |
| 4,300,003 | 11/1981 | Möhring et al. | 521/158 |

Primary Examiner—Maurice J. Welsh
Attorney, Agent, or Firm—Gene Harsh; Joseph C. Gil; Richard A. Elder

[57] ABSTRACT

This invention relates to a process for the preparation of polyurethane resins by the reaction of polyisocyanates with a mixture of various low molecular weight hydroxyaldehydes, hydroxyketones and polyhydric alcohols obtained by an improved process for the condensation of formaldehyde with itself.

1 Claim, 2 Drawing Figures

PROCESS FOR THE PREPARATION OF POLYURETHANE RESINS USING LOW MOLECULAR WEIGHT POLYHYDROXYL COMPOUNDS PREPARED BY THE CONDENSATION OF FORMALDEHYDE

This application is a division, of application Ser. No. 122,931 filed Feb. 20, 1980, now U.S. Pat. No. 4,301,310 which itself is a division of application Ser. No. 829,173 filed Aug. 30, 1977, now U.S. Pat. No. 4,219,508.

BACKGROUND OF THE INVENTION

Polyhydroxyl compounds have become of great commercial importance in various fields. They are used on a large industrial scale, for example, for the manufacture of non-ionic surface active compounds, as antifreezes, as moisturizers and plasticizers and as starting components for the production of synthetic resins such as polyester and polyether resins. Polyhydric alcohols are at present obtained from naturally occurring substances such as sugar or cellulose materials or synthesized by the oxidation of petroleum derivatives.

In view of the world food situation, it is undesirable to use naturally occurring substances as raw materials for industrial products if these substances can be used as carbohydrate sources for nutrition. On the other hand, in view of the shortage of petroleum sources, the price of products which are dependent upon petroleum is constantly increasing. Moreover, the supply of petroleum products is not ensured in the long term.

It would therefore be desirable to find processes for the manufacture of polyhydroxyl compounds from raw materials which are independent of petroleum and other naturally occurring substances.

Since the work of Butlerow and Loew (Ann. 120, 295 (1861) and J. pr. Chem., 33, 321 (1886)) in the last century it has been known that hydroxyaldehydes and hydroxy ketones are formed from the condensation of formaldehyde hydrate (hereinafter the term "condensation of formaldehyde" should always be understood to mean "condensation of formaldehyde hydrate with itself") under the influence of basic compounds such as calcium hydroxide or lead hydroxide. Since formaldehyde can be obtained from coal or natural gas by way of methanol, this would in theory be a possible source of hydroxyl compounds which would be independent of petroleum. Polyhydric alcohols could then be synthesized by electrolytic reduction or by catalytic or chemical hydrogenation.

However, in spite of several proposals for the synthesis of polyhydroxyl compounds by the condensation of formaldehyde, no commercially viable process has yet been developed for such a synthesis, since no one has succeeded in synthesizing mixtures of polyhydroxyl compounds in which the hydroxyl functionality is clearly reproducible. Moreover, the known processes give rise to hydroxyaldehyde and hydroxyketone mixtures which are difficult to hydrogenate and only with very large quantities of catalyst. This high catalyst consumption has hitherto indicated that the synthesis of polyhydroxyl compounds by the autocondensation of formaldehyde hydrate is uneconomic. This has prevented the condensation of formaldehyde hydrate from being used as a basis for a commercial process for the synthesis of polyhydric alcohols.

Due to the disproportionating reaction of formaldehyde to methanol and formic acid which takes place at the same time, only moderate yields have been obtained by the known processes so that the working up of the aqueous or aqueous/alcoholic solutions obtained involved considerable costs which rendered the process uneconomical.

It is known that the disproportionation of formaldehyde into methanol and formic acid is very powerfully catalyzed by basic compounds. It has been shown by Pfeil, Chemische Berichte 84, 229 (1951) that the reaction velocity of this co-called Cannizzaro reaction depends upon the square of the formaldehyde concentration whereas the reaction velocity of formaldehyde polyaddition (C—C linkage) depends directly upon the formaldehyde concentration (Pfeil and Schroth, Chemische Berichte 85, 303 (1952)). The proportion of the desired polyhydroxyl compounds obtained to the quantity of methanol and formic acid produced is therefore shifted in favor of the unwanted compounds as the aldehyde concentration increases. In most of the known processes, it is therefore proposed that the condensation of formaldehyde to hydroxyaldehyde and hydroxyketones should be carried out in solutions having a low formaldehyde concentration in order to keep the quantity of by-products as low as possible. In that case, the water used as solvent must subsequently be removed by distillation to recover the hydroxyaldehydes and hydroxyketones formed in the process. This involves considerable energy costs due to the high heat of evaporation of water. Processes for the condensation of formaldehyde from dilute aqueous solutions are therefore uneconomical. Moreover, if distillation is prolonged, the hydroxyaldehydes and hydroxyketones undergo considerable decomposition and discoloration reactions.

A process for the preparation of aliphatic hydroxyaldehydes in which a 40% formalin solution is reacted with thallium or thallium hydroxide has been described in German Patent No. 822,385. However, this process is of doubtful value in view of the toxicity of thallium. Moreover, thallium hydroxide is difficult to obtain. The yields of this process are relatively low, ranging from 70 to 80%.

With a view to preventing the Cannizzaro reaction, it has also been proposed to react formaldehyde solutions with calcium hydroxide or lead hydroxide in the presence of methanol, ethanol or other polar organic solvents as described in German Patent No. 830,951 and Gorr and Wagner, Biochemische Zeitschrift, 262, 361 (1933). However, the addition of organic solvents again reduces the formaldehyde content of the solution. These processes would therefore also seem to be uneconomical in view of the additional energy costs required for evaporating the added solvent to work up the hydroxyaldehydes and hydroxyketones formed.

A process for the preparation of oxy-oxo compounds in which aqueous formaldehyde solutions at concentrations of up to 30% are reacted with lead oxide or lead acetate and inorganic bases to form sugar-like compounds which reduce Fehling's solution in the cold has been described in German Patent No. 884,794. In this process, however, the formaldehyde solution must be heated for 7 to 8 hours; the volume/time yield is therefore unsatisfactory. The relatively low yields (approximately 80%, based on the quantity of formaldehyde put into the process) are also by no means satisfactory.

A process for the preparation of hydroxyaldehydes and hydroxyketones in which the exothermic condensation of formaldehyde with itself is regulated by the controlled addition of inorganic or organic bases to a formaldehyde solution containing lead, tin, calcium, barium, magnesium, cerium or thorium compounds and a compound which is capable of enediol formation, such as glucose, ascorbic acid, fructose, benzoin, glycol aldehyde, erythrose, reductose, invert sugar or condensation products of formaldehyde, has been disclosed in U.S. Pat. No. 2,224,910. Although this process gives rise to a mixture of hydroxyaldehydes and hydroxyketones from relatively concentrated formaldehyde solutions without the addition of organic solvents, this advantage is offset by various disadvantages. If the reaction is carried out at a low pH value, the reaction product consists mainly of hydroxyaldehyde and hydroxyketone mixtures having a low hydroxyl functionality. Moreover, only moderate reaction velocities are attained at low pH values, so that the volume/time yields obtained in this variation of the process are not satisfactory. To overcome these disadvantages, it is recommended in the Specification to start formaldehyde condensation at a low pH value and to complete it at a higher value. However, at pH values of 7 or higher, lead catalyzed formaldehyde condensation proceeds so rapidly, spontaneously and uncontrollably, that it is not possible by this variation of the process to obtain mixtures of hydroxyaldehydes and hydroxyketones with a reproducible distribution of components. The reaction times and conditions can no longer be accurately controlled. Furthermore, it is well known that in an alkaline medium and at elevated temperatures, hydroxyaldehydes, hydroxyketones and monosaccharides decompose into dark colored compounds in part containing carboxyl groups.

A major disadvantage of the processes previously known is that the substances used as the source of formaldehyde are aqueous formalin solutions. As is well known, these are obtained on an industrial scale by a multistage process of absorption of formaldehyde from formaldehyde-containing synthesis gases in water in a series of absorption columns, followed by removal of the water by distillation to concentrate the product. These steps of the process which have up to now been necessary render the manufacture of sugar aldehydes and ketones from formaldehyde (hereinafter referred to as "formoses") and of the sugar alcohols (hereinafter-referred to as "formite") obtained from them by hydrogenation a relatively uneconomical process. It is therefore an object of the present invention to provide an economical, variable, reproducible and commercially generally applicable process by which formose-sugar mixtures of various desired molecular compositions can be produced in high yields. This process should be capable of providing colorless formoses and formites and, if desired for special purposes, it should also be able to give rise to sugar mixtures with a reddish yellow color which are already strongly caramelized and which may then be used for the applications mentioned above.

DESCRIPTION OF THE INVENTION

It has now surprisingly been found that the hot synthesis gases obtained from the large scale industrial production of formaldehyde can be used directly as a source of formaldehyde for the production of formose. This is particularly surprising because, as will be explained more fully later, it was to be expected that the substantial quantities of carbon dioxide which are invariably present in synthesis gases would inactivate the metal catalysts required for formaldehyde condensation.

It was found, however, that the synthesis gases which contained formaldehyde could be used for the production of formose without previous purification. Although these synthesis gases may contain relatively small quantities of formaldehyde, the formaldehyde can be absorbed quantitatively with unexpectedly high volume/time yields by the process according to the invention in spite of the high flow velocities of the gases. The absorbed formaldehyde can be irreversibly converted into formose-sugar mixtures. According to the reaction conditions employed, these mixtures may also contain reduction and oxidation products produced by a Cannizzaro reaction and aldol condensation products as by-products.

The present invention thus relates to a process for the preparation of a mixture of low molecular weight polyhydric alcohols and, optionally, hydroxyaldehydes and hydroxyketones by the condensation of formaldehyde in an aqueous reaction medium in the presence of a metal compound as catalyst and of a compound capable of enediol formation as cocatalyst, characterized in that synthesis gases containing formaldehyde are conducted continuously or intermittently at temperatures from 10° to 150° C., preferably 70° to 110° C., into an absorption liquid containing (a) 5 to 99% by weight, preferably 30 to 80% by weight of water, (b) 0.1 to 90% by weight, preferably 3 to 80% by weight, most preferably 10 to 70% by weight of compounds capable of enediol formation as cocatalysts, (c) 0 to 20% by weight, preferably 0.01 to 10% by weight, most preferably 0.1 to 5% by weight of soluble or insoluble metal compounds, preferably compounds of metals of the first to eighth sub-Group or of the second to fourth Main Group of the Periodic System of Elements, as catalysts, optionally bound to high molecular weight carriers, and (d) 0 to 60% by weight, preferably 5 to 40% by weight of one or more monohydric or preferably polyhydric low molecular weight alcohols and/or higher molecular weight polyhydroxyl compounds and having a pH of from 3 to 10, preferably from 5 to 8. The formaldehyde is condensed at the same time or, if the absorption solution does not contain catalyst, the formaldehyde is subsequently caused to condense by the addition of catalyst. The condensation of formaldehyde hydrate with itself is stopped in known manner by cooling and/or by inactivation of the catalyst with acids when the residual formaldehyde content in the reaction mixture is from 0 to 10% by weight, preferably from 0.1 to 6.0% by weight. The catalyst is then removed in known manner. If desired, the aldehyde and keto groups in the reaction product are reduced to hydroxyl groups.

It is known that hydroxyaldehydes and hydroxy ketones can be reduced with formaldehyde. Pentaerythritol, for example, can be synthesized from acetaldehyde and formaldehyde. The acetaldehyde is first methylolated to pentaerythrose and then reduced with excess formaldehyde. Such crossed-Cannizzaro reactions can only be carried out in a highly alkaline medium. It was therefore extremely surprising to find that, in the new process, this reduction can be carried out with yields of from 30 to 75% both in a slightly alkaline medium and even in a slightly acid medium. A high proportion of the carbonyl groups are advantageously already reduced at this stage. Subsequent removal of the remaining carbonyl groups by hydrogenation or reduction is thereby considerably simplified.

Another surprising finding is that if oxygen-free synthesis gases are used and if pH values above 9 are avoided, highly concentrated aqueous solutions of hydroxyaldehydes and hydroxyketones are obtained, which are light in color or completely colorless and require no purification. On the other hand, in the processes known in the art, troublesome, strongly colored by-products are formed due to the decomposition reactions. These by-products cannot be removed or only with great effort and at considerable expense. Moreover, these highly colored solutions obtained by the known art processes are difficult or impossible to hydrogenate to polyhydric alcohols and at best only with low yields. On the other hand, catalytic hydrogenation of the reaction mixtures according to the invention after removal of the lead catalyst e.g. by simple precipitation or by means of ion exchangers can be carried out under the mild conditions normally used for the catalytic hydrogenation of sugars.

In the process according to the invention, glycol aldehyde is first formed from two molecules of formaldehyde. Glyceraldehyde is then formed from it by further addition of formaldehyde in accordance with the following reaction scheme:

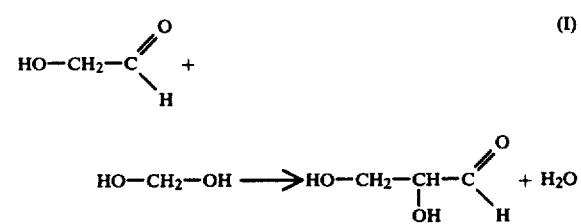

This then gives rise to the mixtures of hydroxy aldehydes and ketones according to the invention by a large number of subsequent reactions, some of which are illustrated below by way of example:

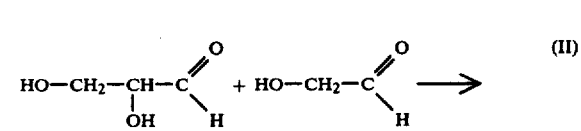

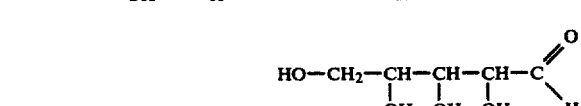

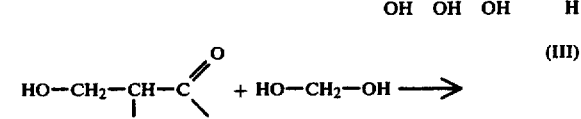

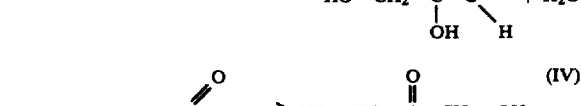

-continued

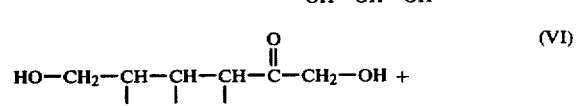

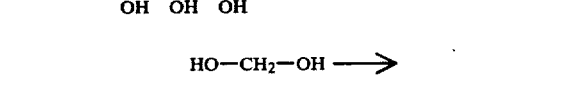

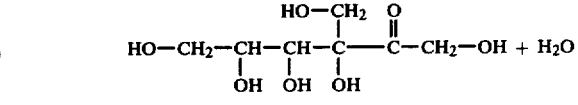

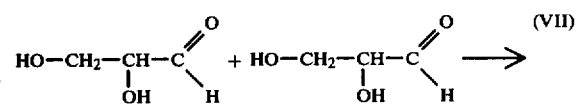

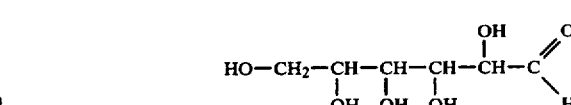

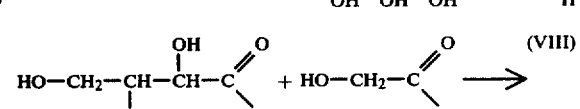

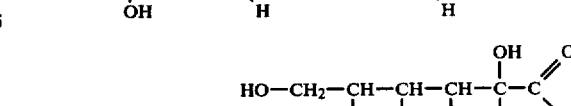

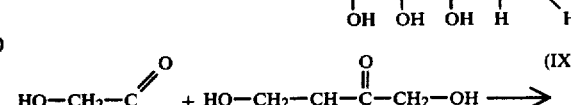

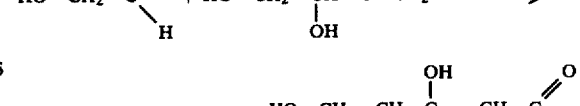

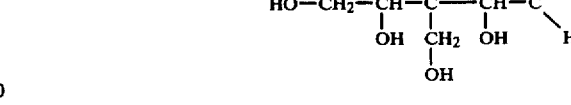

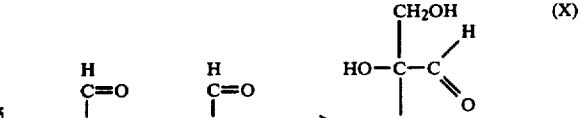

Acyloin condensation

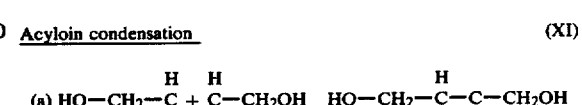

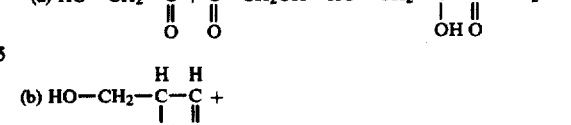

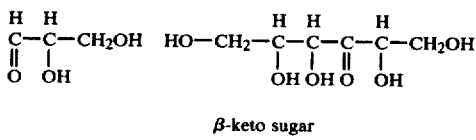

β-keto sugar

According to the invention the condensation of formaldehyde is catalyzed by metal compounds which may be readily soluble or only sparingly soluble in water, in particular by compounds of the first to eighth sub-Groups and the second to fourth Main Groups of the Periodic System of Elements. The following compounds, used alone or as mixtures, are examples of suitable catalysts according to the invention: Calcium oxide, calcium hydroxide, the hydroxides of lithium, beryllium, scandium, bismuth, aluminum, magnesium, zinc, strontium, tin, thallium, barium and the rare earths; the oxides of these metals, mixed oxides and hydroxides of these metals with each other, for example mixed compounds of calcium hydroxide with oxides and oxyhydrates of the rare earths, aluminum hydroxide, freshly precipitated titanium hydroxides, chromium-III hydroxide, the hydroxides and oxyhydrates of molybdenum, tungsten, manganese-(II), iron-(II), iron-(III), cobalt, nickel and vanadium, the oxides and hydroxides of divalent and tetravalent lead, aluminum oxyhydrates; hydrates of alumina, if desired as mixtures with hydroxides and oxyhydrates of trivalent and pentavalent antimony, freshly precipitated silicic acid and polysilicic acids and salts of the above mentioned metals with any organic acids, in particular organic carboxylic acids. Ash residues of any origin, particularly those of plants and biological masses (for example clarification slurry) contain a wide spectrum of compounds of calcium, magnesium, potassium and various trace elements and are therefore particularly valuable and at the same time inexpensive catalysts for the process according to the invention.

Among compounds of the kind mentioned above, those which are only sparingly soluble in water are preferably first dissolved or dispersed in the cocatalytically active compounds capable of enediol formation because they dissolve relatively easily in these cocatalysts by complex formation.

According to the invention, it is particularly advantageous to use calcium or lead compounds as catalysts e.g. the oxides, hydroxides and formates of calcium and lead and the acetate, nitrate, carbonate, oxalate, phenolate, thiophenolate and salicylate of divalent lead.

If used for formose formation, all the above mentioned catalysts should preferably be present in quantities of about 0.01 to 10% by weight, most preferably 0.1 to 5% by weight, based on the quantity of reaction mixture.

If lead(II) ions are used as catalysts, it is advantageous to remove them as elementary lead by electrolytic cathodic depositin. In that case, the lead can be returned to the production process as catalyst, for example by converting it into the acetate or by oxidizing it anodically and at the same time dissolving it.

The waste products formed in the known processes, which are not ecologically harmless, are thus prevented from forming in the process according to the invention. In view of the possibility of recycling the lead catalyst, the process is therefore superior to the known processes, on ecological as well as economical grounds.

The metal ions used as catalysts are easily and preferably removed from the reaction mixture by pumping the reaction solution over cation active ion exchangers. Analysis by atomic absorption has shown that reaction solutions which have been treated in this way contain, for example, only 0.5 ppm of lead ions.

The ion exchangers, for example those which are partly or completely charged with lead after some time due to removal of lead from the reaction solutions, or ion exchangers which have been charged with metal ions, preferably lead ions, by deliberately directing a stream of metal salt solution over them, may also be used as catalysts for the condensation of formaldehyde hydrate with itself under the conditions of the process of the invention. It has been found, for example, that calcium or lead-charged ion exchanger resins, (e.g. the known sulphonated polystyrene resins cross-linked with divinyl benzene, cross-linked acrylic acid resins or urea formaldehyde resins which have been modified with acid groups) catalyze the formaldehyde condensation as successfully as soluble lead or calcium salts. It is particularly advantageous that much smaller quantities of lead can then be used than in the processes known in the art. Another advantageous feature is that these lead charged ion exchangers are obtained directly by the removal of lead ions from the reaction solution and, after their use as catalyst, they can be used again for the removal of lead ions.

According to a preferred embodiment of the process of the invention, it is particularly advantageous to adopt the following procedure: A certain quantity of ion exchanger resin charged with lead (or any other metal) is pumped as solid catalyst through the absorption column or, in a discontinuous variation of the process, it is used as solid bed catalyst. During the reaction, lead ions are given off to the absorption liquid so that the solid catalyst gradually becomes depleted of lead ions. After repeated use, that part of the ion exchanger resin which was used as solid catalyst only contains such a small quantity of lead ion that its catalytic action diminishes. After it has been washed with water, it can therefore be used for removing lead from the reaction mixture.

The other part of the ion exchanger resin, which was used for removing lead from the solution, is now heavily charged with lead ions. That part which was used for removing lead from the reaction solution is now pumped through the absorption column or used as solid bed catalyst in a second absorption column while the other part, which is by now no longer completely charged with lead, can be used for absorbing lead ions from the end product.

The lead required for catalysis can thus be completely utilized without fresh quantities of lead salts having to be continuously supplied or harmful by-products being formed. This variation of the process is therefore particularly interesting on economical and ecological grounds.

The solid catalysts used for the process according to the invention may in principle be any high molecular weight, insoluble, cross-linked or uncross-linked resins which contain metal ions such as divalent lead, calcium, zinc, tin, magnesium or aluminum bound to acid groups. The preferred ionic matrices are commercial polystyrene resins cross-linked with divinylbenzene which contain, for example, $SO_3H$ groups, $COOH$ groups or

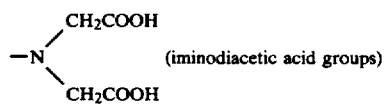

in the molecular structure.

Other preferred macromolecular, insoluble formose catalysts are, for example, phenol-formaldehyde condensates containing built-in salicylic acid groups or

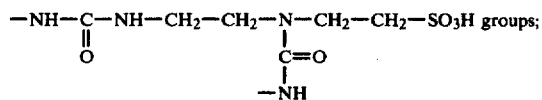

or polymethylene ureas having the following recurrent structural units

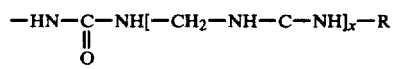

in which

R represents hydrogen, $CH_2OH$, $CH_2-OCH_3$ or $CH_2-OC_2H_5$ and x represents a value from 0 to 20, which polymethylene ureas contain in their molecular structure the following groups:

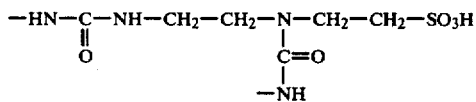

and/or

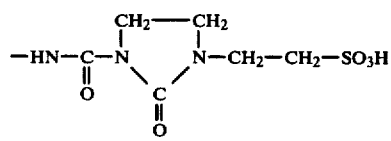

and/or

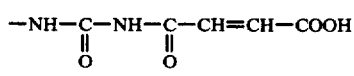

and/or

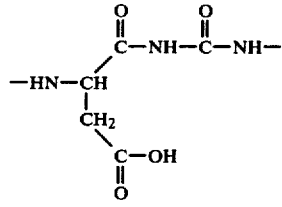

and/or

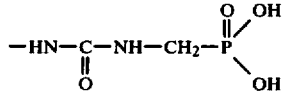

which are saturated with lead or calcium, tin, magnesium or aluminum ions, ions of rare earth elements, etc.

Mixed melamine and urea condensates with formaldehyde in which melamine and urea are present in a molar ratio of from 1:1 to 0.5:1 and which contain approximately 180 milliequivalents per 100 g of the above mentioned ionic groups condensed into the molecular structure are also of interest as high molecular weight, insoluble formose catalysts. Also of interest are the saponified copolymers of maleic acid anhydride and styrene having the following structural units:

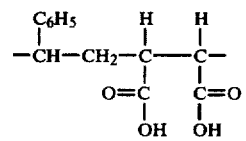

as well as insoluble copolymers of acrylic acid or methacrylic acid with styrene, butadiene, vinyl acetate, butyl acrylate, acrylamide, N-methoxymethylmethacrylamide, β-hydroxyalkylacrylates, etc. which are charged with, for example, lead(II) or calcium ions.

Polymers of acrylic and methacrylic acid which are cross-linked, for example with divinylbenzene, and which are in the form of gels which readily swell may also be used as catalysts, for example in the form of their calcium or lead salts. Ion exchanger resins suitable for use as catalysts according to the invention generally contain from 50 to 300, preferably from 180 to 250, milliequivalents of ionic groups per 100 g of solid substance.

The synthesis gases obtained from the large scale industrial production of formaldehyde generally contain, depending on the method by which they have been produced, about 1 to 10 volume % of carbon dioxide in addition to about 1 to 20 volume % of formaldehyde. Since most of the metals mentioned above, for example, also the preferred catalysts, calcium and lead, form insoluble carbonates at medium pH values, it was to be expected that when synthesis gases containing formaldehyde were used as source of formaldehyde for the production of formose, the catalysts used would be rapidly inactivated. It has surprisingly been found, however, that in spite of the very large quantities of carbon dioxide present—in the preferred, continuous process according to the invention, an approximately 300 to 600-fold molar excess of carbon dioxide over metal catalyst is present—no interference with the catalytic activity of the metal ions takes place. As has already been indicated above, this is presumably due to the surprisingly high capacity of formose to form very stable complexes with a wide variety of metal ions.

The liquids used according to the invention as absorbents for the formaldehyde-containing synthesis gases contain compounds which are capable of enediol formation, which compounds powerfully accelerate the condensation of formaldehyde to formose when used together with the metal catalysts described above. In theory, any compounds which contain a hydroxyl group in the α-position to a keto or aldehyde group may be used as such cocatalysts, e.g. also those compounds which are used as cocatalysts in the processes already known in the art. As is known, α-hydroxy carbonyl compounds are in tautomeric equilibrium with enediols as follows:

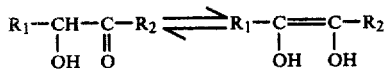

In the above reaction scheme, $R_1$ and $R_2$ represent hydrogen, alkyl, hydroxyalkyl, polyhydroxyalkyl or aryl groups.

The following are examples of such cocatalysts: Glucose, ascorbic acid, fructose, benzoin, glycol aldehyde, glyceraldehyde, erythrose, reductones and invert sugar, various hydrolyzed polysaccharides and higher molecular weight polymeric enediols such as those which according to results of recent research carried out by the present Applicant are also present in caramelized sugars and in branched chain formoses which contain keto and aldehyde groups.

According to the invention, however, the preferred cocatalysts are formoses, which may be prepared by any method of preparation. Formoses contain numerous enediols, for example as represented in the following reaction scheme. They have an extremely powerful accelerating effect on formaldehyde condensation and in particular they eliminate the induction period at the beginning of the formation of formose.

cocatalysts. Particularly preferred cocatalysts are formoses which are characterized by the following molar ratios:

Compounds with 3 carbon atoms/compounds with 4 carbon atoms: 0.5:1–2.0:1;

Compounds with 4 carbon atoms/compounds with 5 carbon atoms: 0.2:1–2.0:1;

Compounds with 5 carbon atoms/compounds with 6 carbon atoms: 0.5:1–5.0:1;

the proportion of components having from 3 to 6 carbon atoms amounting to at least 75% by weight, preferably more than 85% by weight, based on the total quantity of cocatalyst.

These preferred cocatalysts advantageously develop their catalytic activity even at pH values below 7. The Cannizzaro reaction or reactions at these pH values which cause yellowing and caramelization only occur to a very slight extent. Completely colorless formose mixtures can be obtained if desired. For this purpose, it has been found particularly advantageous to use, as cocatalysts, formoses which have been prepared by the condensation of formaldehyde with the aid of lead as catalyst. Such colorless formose mixtures are also easily hydrogenated and give rise to exceptionally light colored products on alkoxylation. Another advantage of Scheme for the formation of various enediol equilibria in formoses:

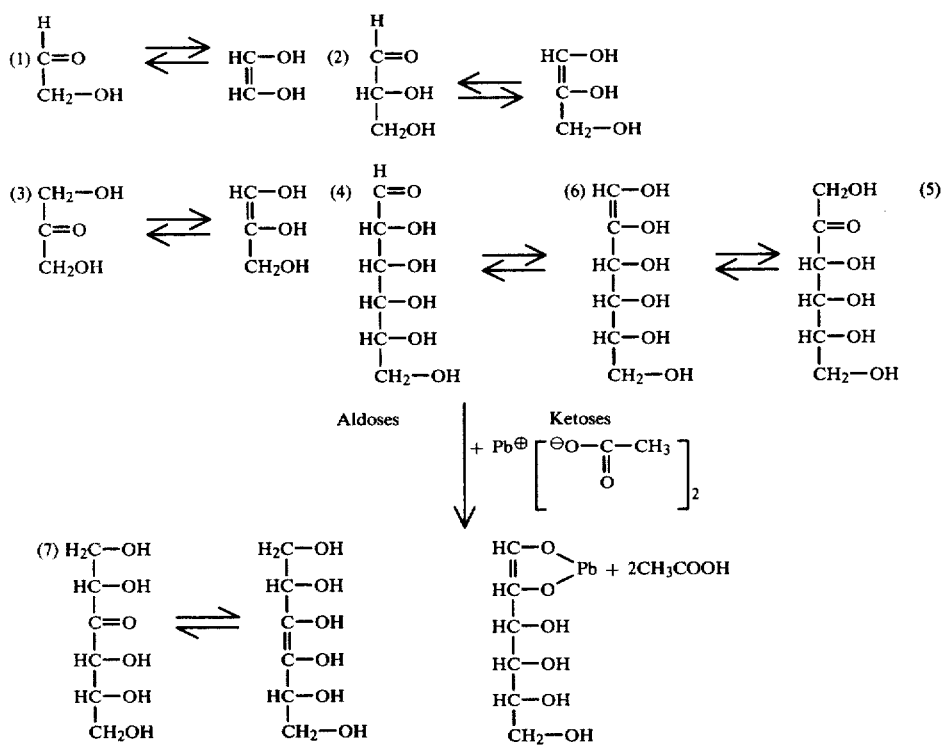

The enediol compounds represented in the above scheme can form very stable complexes with various metals, for example with lead, calcium, magnesium, zinc, tin, aluminum, barium, strontium, manganese, nickel, cobalt and thallium, as shown above schematically by the example of enediol 6. Each metal atom may have two or three enediols as ligands.

As will be explained in more detail below, mixtures of the formoses according to the invention with any monohydric or polyhydric alcohols may also be used as using formoses as cocatalysts is the considerably increased speed of absorption or absorption capacity of aqueous formose solutions for gaseous formaldehyde. Thus, for example, 10% aqueous formose solutions can absorb approximately 40% by weight of formaldehyde within a few minutes at 80° to 100° C. A 75% aqueous formose solution can absorb as much as about 60% by weight of formaldehyde under the same conditions.

Below are shown the compositions of two typical formoses which can be used as cocatalysts in the process according to the invention:

| (A) | 1. Hydroxyacetaldehyde: | 0.2% by weight |
|---|---|---|
| | 2. Glyceraldehyde or dioxyacetone: | 2.6% by weight |
| | 3. C$_4$—polyhydroxyaldehydes or ketones: | 4.6% by weight |
| | 4. C$_5$—polyhydroxyaldehydes or ketones: | 24.8% by weight |
| | 5. C$_6$—polyhydroxyaldehydes or ketones | 44.5% by weight |
| | 6. C$_7$—polyhydroxyaldehydes and ketones | 23.5% by weight |
| (B) | 1. Hydroxyacetaldehyde: | 16.8% by weight |
| | 2. Glyceraldehyde or dioxyacetone: | 21.0% by weight |
| | 3. C$_4$—polyhydroxyaldehydes or polyhydroxyketones: | 29.9% by weight |
| | 4. C$_5$—polyhydroxyaldehydes or polyhydroxyketones: | 25.1% by weight |
| | 5. C$_6$—polyhydroxyaldehydes or polyhydroxyketones: | 7.2% by weight |

The formoses mentioned above as examples, which may be prepared by any known processes in the art, generally also contain approximately 10 to 40% by weight of polyhydroxyl compounds which contain no carbonyl groups.

The proportions in which the individual components are mixed in the formoses used as cocatalysts can be varied by controlled addition of, for example, glyceraldehyde, erythrose, fructose, glucose or honey. According to the invention it is also possible, as will be explained below, to add to the cocatalysts up to 400% by weight of various alcohols, aldehydes or ketones, for example, acetaldehyde, isobutyraldehyde, butyraldehyde, methyl ethyl ketone, acetone, diethylketone, cyclohexanone or ethyl acetoacetate.

Among the preferred cocatalysts according to the invention may also be included mixtures of hydroxyketones, hydroxyaldehydes, hydroxycarboxylic acids and ketocarboxylic acids of the kind obtained by partial oxidation of polyols which carry hydroxyl groups on at least two adjacent carbon atoms and have a molecular weight of between 62 and 250.

It does not matter whether the oxidation of polyhydric alcohols is carried out in a completely separate reaction step, immediately before the condensation reaction according to the invention or only later, in the reaction mixture itself. For practical reasons, however, it is preferred to carry out this oxidation reaction while the reactants flow along the mixing path to the reaction vessel for the formaldehyde condensation reaction. The most preferred method is to let the oxidation reaction take place in situ in the absorption liquid already containing formaldehyde. It is to be regarded as extremely surprising that it is even possible to obtain sufficient quantities of cocatalyst by this last mentioned variation of the process, which is particularly preferred according to the invention. Owing to the ease with which formaldehyde can be oxidized (it may be remembered here that the usual method of determining formaldehyde consists of oxidizing it with hydrogen peroxide according to the following equation:

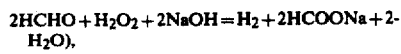
2HCHO + H$_2$O$_2$ + 2NaOH = H$_2$ + 2HCOONa + 2-H$_2$O), it was reasonable to assume that if the oxidizing agent reacted with the polyhydric alcohol to form hydroxyaldehydes, ketones, carboxylic acids, etc., it would do so to only a very minor extent and that it would mainly attack the formaldehyde which was present in a concentrated form.

The reaction mechanism of this variation of the process according to the invention and the mode of action of the catalyst are still to a large extent unknown. This applies particularly to the initial phase of the condensation reaction, during which the accelerating action of the catalyst/cocatalyst system according to the invention is particularly important. It may be assumed, however, without this asumption in any way restricting the scope of protection of the present invention, that the hydroxyaldehyde or hydroxyketone formed in the first stage of oxidation of a polyhydric alcohol is not alone responsible for the catalytic effect. This follows partly from the fact that aldehyde functions are much more easily oxidized than hydroxyl groups. Partial oxidation of polyhydric alcohols always results in only very small quantities of hydroxyaldehydes in addition to the main product, which consists of hydroxycarboxylic acids, and partly from the observation that a hydroxyaldehyde, e.g. glycol aldehyde or glyceraldehyde, alone or mixed with the corresponding polyalcohol only gives rise to the formation of unsatisfactory, brown discolored products when it is used as cocatalyst for the condensation of formaldehyde. It is, in fact, more likely, although surprising, that the hydroxycarboxylic acids act as cocatalysts, either alone or as synergistic combinations with the traces of hydroxyaldehydes and/or hydroxyketones, and possibly also non-oxidized polyol, present.

The quantity of cocatalytically active, partially oxidized alcohol or alcohol mixture can be varied within wide limits in this variation of the process of the invention. In many cases, more than sufficient quantities of cocatalyst can be produced from only 1% by weight of alcohol, based on the quantity of formaldehyde put into the process. However, it is advantageous to use larger quantities, about 2 to 10% by weight, based on the quantity of the formaldehyde in the absorption liquid, of polyhydric alcohol or alcohol mixtures, particularly when oxidation is carried out in situ, so that a sufficient quantity of oxidation products of these alcohols will be formed at the beginning of the formaldehyde condensation reaction and be available as cocatalysts.

The quantity of polyhydric alcohol or alcohol mixture should not generally lie below the lower limit of 0.001 hydroxyl equivalents, base on 1 mol of formaldehyde put into the process. The cocatalytical activity is otherwise too weak. There is in principle no upper limit to the quantity used although for practical reasons it is preferred not to exceed a quantity corresponding to 0.10 hydroxyl equivalents. It is particularly advantageous to operate within a range of from 0.002 to 0.02 hydroxyl equivalents, based on 1 mol of formaldehyde.

The upper limit of the quantity of oxidizing agent to be put into the process is set by the quantity of polyhydric alcohol or alcohol mixture present since only those alcohols which are partially oxidized, to hydroxyaldehydes, -ketones and -carboxylic acids, act as cocatalysts (see above). By "partially oxidized" is meant in the context of this invention that not more than 85%, preferably less than 70%, most preferably less than 50%, of all the hydroxyl groups of the polyhydric alcohol are oxidized. According to the invention, one may, of course, use a larger quantity of oxidizing agent than the maximum quantity theoretically calculated from these figures since some of the oxidizing agent is lost by reaction with formaldehyde, particularly in the preferred variation in which the cocatalyst is formed in situ. However, one should not use more oxidizing agent than is theoretically required for the oxidation of all the hydroxyl groups of the polyhydric alcohol to keto groups or carboxyl groups because otherwise too many side reactions take place which reduce the total yield of formaldehyde condensation products.

As in the case of alcohol, the quantity of oxidizing agent used should also not fall below the lower limit of 0.001 equivalents per mol of formaldehyde because otherwise the proportion of cocatalytically active oxidation products is too low.

Examples of alcohols which are suitable for the preparation of the cocatalyst by partial oxidation, preferably along the mixing path or in situ, include propylene glycol-(1,2), butylene glycol-(2,3), hexanediol-(2,3) and -(3,4), 2-methyl-1,2-propanediol, butanetriol-(1,2,4), hexanetriol-(1,2,6), erythritol, quinitol, mannitol, sorbitol and methyl glycoside. Polyhydric alcohols, having at least one primary hydroxyl group are preferred, particularly ethylene glycol and glycerol as well as the sugar alcohol mixtures formed in the formaldehyde condensation process and reduced by a crossed Cannizzarro reaction.

Any known oxidizing agents for alcohols may be used for the partial oxidation of the above mentioned dihydric or higher hydric alcohols, or mixtures thereof, which have at least two adjacent hydroxyl groups. The following are examples of such oxidizing agents: Compounds of divalent copper, e.g. copper(II) nitrate; compounds of trivalent iron, e.g. iron(III) chloride and potassium hexacyanoferrate (III); compounds of monovalent silver, e.g. silver(I) oxide; compounds of tetravalent or heptavalent manganese, e.g. manganese dioxide or potassium permanganate; compounds of pentavalent vanadium, e.g. divanadium pentoxide; compounds of hexavalent chromium, e.g. chromium trioxide, chromic acid, sodium or potassium dichromate; selenium dioxide, osmium tetroxide, hydrogen peroxide; oxygen compounds of nitrogen, e.g. alkali metal hyponitrite, nitrous acid or its salts; nitric acid or its salts; halogens and their heptavalent oxygen compounds, e.g. sodium periodate or potassium perchlorate; inorganic or organic peracids or their salts, e.g. sodium pyrosulphate, ammonium peroxy disulphate, peracetic acid and perbenzoic acids; lastly, oxygen or air. It is preferable to use readily available oxygen-containing compounds, such as nitric acid, hydrogen peroxide and chromic acid.

Potassium permanganate and lead(IV) oxide, which acts both as oxidizing agent and as catalyst, are particularly preferred. Anodic oxidation may also be carried out.

As already mentioned above, the cocatalyst could in principle be prepared separately by the partial oxidation of the polyhydroxy compound and then added in the required quantity to the absorption liquid. In many cases, however, the partially oxidized polyhydric alcohols are not stable in storage and tend to undergo reactions which cause brown discoloration. For this reason, and for reasons of simplicity, it is more suitable to mix the polyhydric alcohol and oxidizing agent along the mixing path, i.e. immediately before introduction into the absorption column, or to add the oxidizing agent to the absorption liquid of water, polyhydroxyl compound having at least two adjacent hydroxyl groups, and optionally catalyst. Even when oxidation is carried out in a separate step or along the mixing path, it is preferable to oxidize the polyhydric alcohol in the presence of the metal catalyst. Presumably, when this method is employed, the enediol compounds formed as intermediate products are absorbed by the metal ions by complex formation and thereby converted into a catalytically highly active form.

Apart from formoses and the oxidation products of polyhydric alcohols described above, it is also advantageous to use as cocatalysts honey-like easily pourable hemiacetals of formaldehyde of polyhydroxy aldehydes and polyhydroxy ketones, particularly of formoses, as represented by way of example in the following formulae:

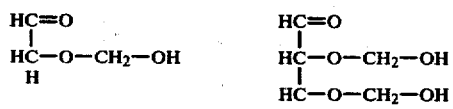

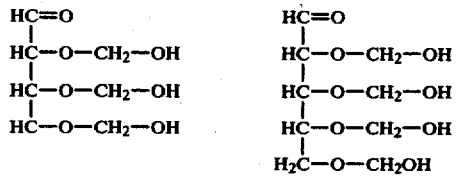

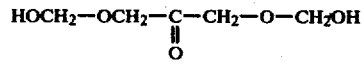

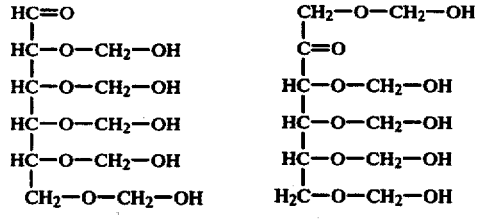

In the presence of water, these hemiacetals very rapidly establish a dissociation equilibrium with the corresponding hydroxyl compounds and free formaldehyde. In this way they give rise to compounds which are again capable of enediol formation, as illustrated by way of example in the following reaction scheme of hemiacetals of hydroxyacetaldehyde and glyceraldehyde:

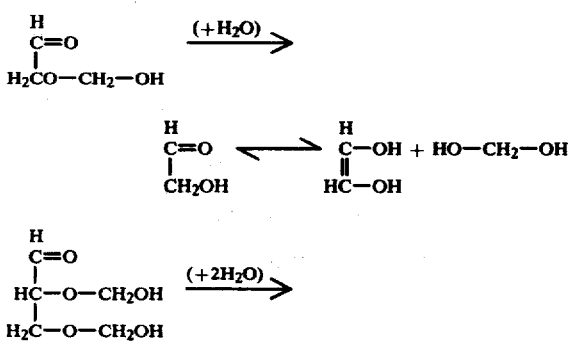

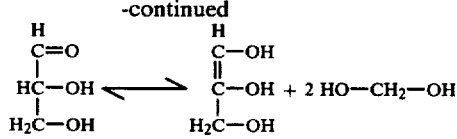

If the hemiacetals described above are used together with monohydric alcohols (e.g. methanol, ethanol, ethylene glycol monomethyl ether or ethylene glycol monoethyl ether) or polyhydric alcohols free hydroxyaldehydes or hydroxyketones are then again formed by trans-hemiacetalization of these monohydric or polyhydric alcohols. These free hydroxyaldehydes or hydroxyketones formed are in tautomeric equilibrium with the enediol form. The highly fluid hemiacetals of formose described above are completely stable in storage. They may be prepared, for example, by mixing formose with the formaldehyde hemiacetal of methanol or by introducing gaseous formaldehyde into formose. The formose hemiacetals may also contain a proportion of polyoxymethylene ether residues.

The use of the above described hemiacetals of hydroxy aldehydes and hydroxyketones as cocatalysts is particularly advantageous for the preferred, continuous method of producing formose according to the invention, since a large quantity of formaldehyde is introduced into the reaction mixture at the initial phase of the reaction and consequently the time required for establishing a stationary flow equilibrium is greatly reduced.

Polyhydroxyaldehydes and ketones which have been pretreated by heat and/or with small quantities of bases e.g. alkali metal hydroxides or tertiary amines, particularly formoses which have been pretreated in this way, may also be added as cocatalysts to the absorption liquid. Molecular rearrangement and dehydration reactions take place in such pretreated sugars to give rise to reddish to reddish brown higher molecular weight condensates with conjugated double bonds and possible also allenestructures the exact constitution of which have not yet been elucidated.

The enol content or enediol content is substantially increased in such modified sugars:

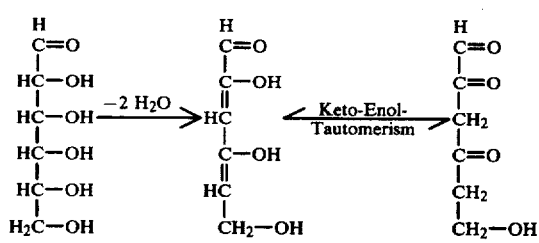

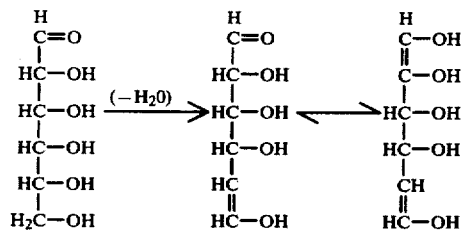

It has been discovered from experimental results not yet published by the Applicant that methylol end groups in sugars with conjugated polyene structures have a similar reactivity in aldol reactions to hydrogen atoms in the α-position of carbonyl groups. Compounds such as those of the type illustrated in the first of the two above schemes of formulae are therefore capable of aldol condensation accompanied by considerable intensification of color due to the increasing concentrations of conjugated double bonds:

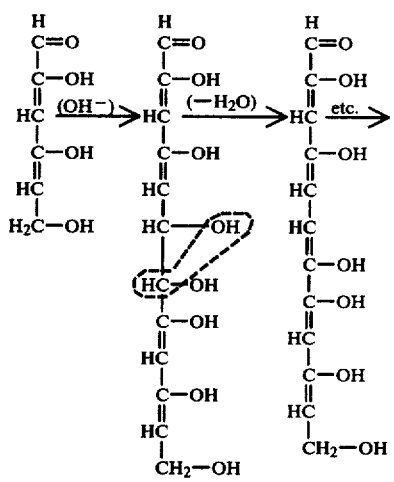

In addition, intermolecular aldol condensations take place between open chain sugars in accordance with the following reaction scheme, leading to branched chain sugars

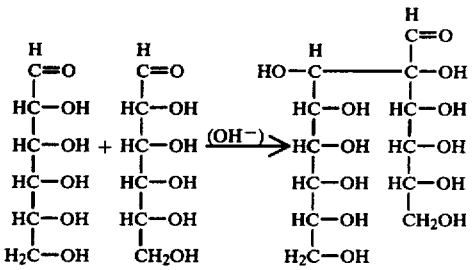

which may in turn be converted into highly colored polyenes due to the activating effect of the carbonyl group on the α- and β-hydroxyl groups, with the elimination of water:

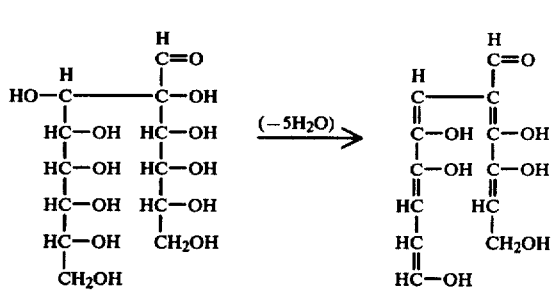

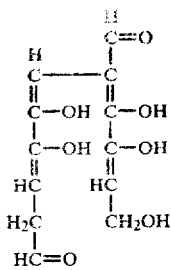

Such higher molecular weight, colored condensation products are also excellent cocatalysts for the process according to the invention.

It has been found that all naturally occurring invert sugars, i.e. the sugar occuring in various types of honey from the honey bee, which in nature generally have water contents of about 10 to 20% by weight and nitrogen contents of about 0.2 to 0.8% by weight, are excellent absorbents with cocatalytic activity for the process according to the invention. By diluting them with water and/or alcohols such as methanol, ethylene glycol or propylene glycol, these honeys can be adjusted to the preferred concentrations for absorption liquids according to the invention, ranging from about 3 to 70% by weight, most preferably from 10 to 60% by weight.

Solutions of artificial invert sugar may also be used as absorption liquids according to the invention, e.g. in the form of 5 to 80% solutions in water and/or monohydric or polyhydric alcohols, preferably ethylene glycol, with viscosities of about 2 to 1000 mPas. These invert sugars are hydrolysates of any disaccharides and/or polysaccharides, e.g. of cane sugar, mixtures of cane sugar and invert sugars, hydrolysates of trehalose (disaccharide), maltose or isomaltose, hydrolysates of corn or potato starch and of pectine materials (amylose and amylopectine), cellobiose and lactose, hydrolysates of galactose, glucose mixtures, raffinose hydrolysates (trisaccharide), cellulose hydrolysates, hydrolysates of dextrins, which may be mixed with non-hydrolyzed dextrins, hydrolysates of Schardinger dextrins (cyclic dextrins), hydrolysates of glycogen, hydrolysates of glucose-6-phosphoric acid, hydrolysates of glucose-1-phosphate (Cori ester), fructose-6-phosphate, degraded pectin materials (polygalacturonic acids), degraded glucosamines and hydrolysates of molasses residues.

Aqueous and alkaline extracts of hydrolysates of homogenized vegetable cells and/or of biomasses have also proved to be excellent absorption liquids with cocatalytic activity for the conversion of formaldehyde into formose-sugar mixtures, e.g. degraded, soluble oligo-ribonucleic acids and desoxyribonucleic acids and their mixtures, adenosine phosphate, adenosine triphosphate, uridine triphosphate, cytidine triphosphate or their calcium, lead, thallium, zinc, barium, tin or magnesium salts.

Such hydrolysates can easily be obtained by acid hydrolysis of any vegetable materials, preferably by hydrolysis of yeasts of all kinds, e.g. baker's yeast, or they can be obtained from biomasses from any commercial fermentation processes since all biomasses are similar in their desoxyribonucleic acid and ribonucleic acid composition with regard to the ribose and desoxyribose constituents. Moreover, all vegetable materials and biomasses contain reserves of monosaccharides, oligosaccharides and polysaccharides which are converted into soluble, cocatalytically active compounds by hydrolysis.

It has surprisingly been found that sugar derivatives of as yet unknown composition which are obtained by the so-called Maillard reaction are also suitable absorption liquids. They have a high cocatalytic activity for the formose synthesis according to the invention. As is known, acid-catalyzed or alkaline-catalyzed Maillard reactions of sugars with primary or secondary amino groups, (e.g. from amino acids, proteins or ethanolamine) result in deep colored substances. In the preliminary stage, they are still soluble in water. The Maillard reaction is also known in the literature as "non-enzymatic browning of sugars" (see Advances in Protein Chemistry, Volume 29, 1975, page 185, Academic Press).

This Maillard reaction mainly consists of carbonylamine reactions, formation of α-aminoalcohols, formation of N-substituted glucosamines, rearrangement reactions of glycosylamines to ketosamines, Amadori rearrangements, Heyns rearrangements, formation of diketoamines and secondary reactions as indicated schematically below by the reaction of cyclohemiacetals of sugars:

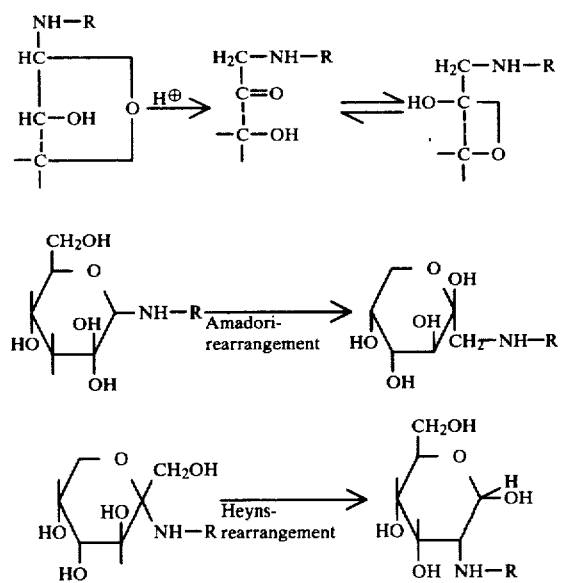

It is possible that equilibrium positions of the cyclohemiacetal forms, with enolamines of the following constitution:

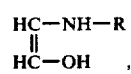

in intermediate products of the Maillard reaction, are of decisive importance for the cocatalytic activity in the formation of formoses.

In the Maillard reaction, dialdehydes and α,β-unsaturated aldehydes are formed in a preliminary stage as decomposition products of amino sugars, e.g. in accordance with the following reaction scheme (see Advances in Protein Chemistry, Volume 29, 1975, page 188, Academic Press):

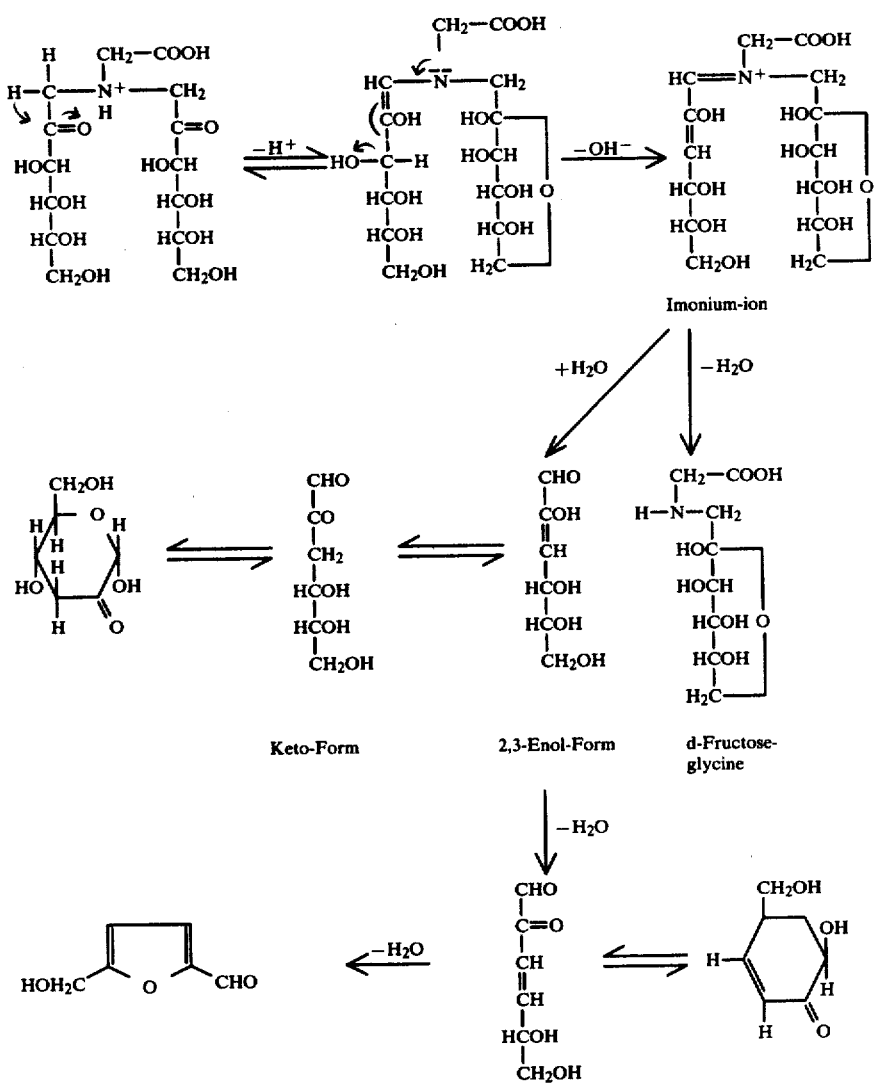

Aqueous or alcoholic solutions of such mixtures of sugar derivatives represented in the above scheme of formulae are also valuable absorption liquids which function as cocatalysts for the formation of formose.

The liquids used according to the invention as absorbents for the formaldehyde and the synthesis gas contain from 0.1 to 90% by weight, preferably 3 to 70% by weight, most preferably 10 to 60% by weight, of compounds capable of enediol formation as cocatalysts in the form of aqueous or alcoholic solutions. The alcohol component of these solutions may consist of monohydric or polyhydric alcohols, for example, ethylene glycol, diethylene glycol, triethylene glycol, trimethylol propane, sorbitol or pentaerythritol.

The preferred process according to the invention is a continuous one in which the absorption liquid is circulated by pumping in countercurrent to the formaldehyde-containing synthesis gas. It is suitable to use higher concentrations of cocatalyst in the continuous process than those used for the intermittent variation of the process, in which the synthesis gas is made to flow through a static absorption liquid until the liquid is saturated with it. In the continuous process, the concentration of cocatalyst in the absorption liquid is approximately 3 to 90% by weight, preferably 20 to 70% by weight, most preferably from 40 to 60% by weight. However, in all variations of the process according to the invention, it is preferred to use the highest possible concentration of cocatalyst in the absorption medium because this greatly increases the capacity of the liquid to absorb formaldehyde as well as increasing the velocity of formose formation. This is true even when only small quantities of metal catalyst are present. If large amounts are used on that average, the formaldehyde from the synthesis gas is almost quantitatively converted into formose after only about 8 to 12 minutes.

As has already been repeatedly mentioned above, the absorption liquids according to the invention may also contain from 0 to about 60% by weight, preferably 10 to 40% by weight of monohydric or preferably polyhydric alcohols having a molecular weight of from 32 to 400 as well as polyols with a molecular weight of between 400 and 10,000 without thereby reducing the absorption of formaldehyde or its irreversible conversion into formose. On the contrary, the absorption capacity of the absorbent is substantially increased by the addition of such hydroxyl compounds because, as already explained above, formaldehyde is very rapidly bound reversibly in the form of hemiacetal groups.

This hemiacetal formation also substantially reduces the vapor pressure of the formaldehyde above the absorption liquid. This again leads to almost quantitative absorption of the formaldehyde from the synthesis gas after only one passage through the absorption liquid. Moreover, the addition of alcohol considerably reduces the viscosity of the absorption liquid as well as the end products, which is advantageous for subsequent processing.

Suitable monohydric and polyhydric alcohols having a molecular weight of from 32 to 400 include, for example, the following: methanol, ethanol, propanol, the isomeric butanols, 2-ethylhexanol, all of the polyhydroxyl compounds already mentioned in detail above as components for the preparation of cocatalysts by the partial oxidation of polyols, in particular ethylene glycol, glycerol, trimethylol propane, formites, diethylene glycol, triethylene glycol, propanediol(1,2), propanediol-(1,3), butanediol-(1,4), N-methyldiethanolamine, N-ethyl-diethanolamine, ethoxylated or propoxylated ethylenediamine, ethoxylated or propoxylated hydrazine or substituted hydrazine (e.g. N,N-dimethyl or -diethyl-hydrazine), water insoluble but emulsifiable polyhydric alcohols such as castor oil, hexanetriol and 2-ethylhexanediol-(1,3) as well as ethoxylation and propoxylation products of all the monohydric and polyhydric alcohols mentioned above. The polyhydroxyl compounds already well known in polyurethane chemistry, which are described in more detail below, are suitable polyols with a molecular weight of between 400 and 10,000.

When formose is prepared in absorption liquids which contain such monohydric or polyhydric alcohols, the formation of formose may be followed by the preparation of acetalized, ketalized or partially acetalized formose mixtures by adjusting the pH to about 1 to 3 and removing water.

Hemiacetals of any of the above mentioned alcohols may, of course, be added to the absorption liquid, for example the following hemiacetals:

$$CH_3-O-CH_2OH,\ C_2H_5-O-CH_2OH,\ \underset{\underset{CH_2-O-CH_2OH.}{|}}{CH_2-OC_2H_5}$$

Liquid hemiacetals of polyalcohols having the following constitutional formulae are particularly preferred:

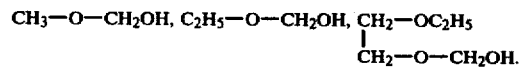

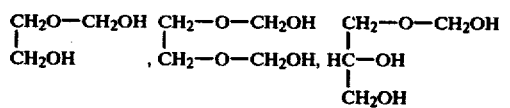

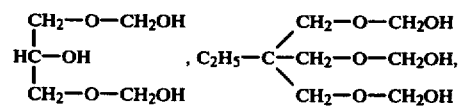

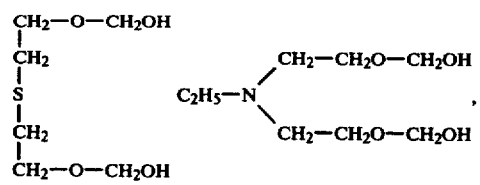

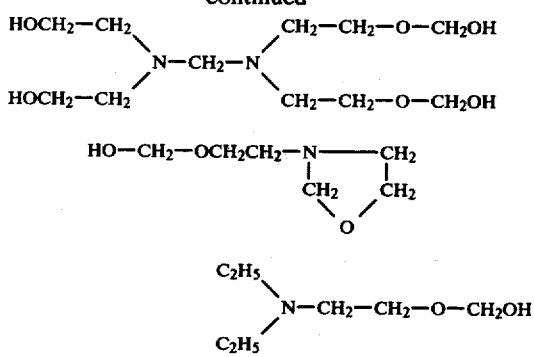

The addition of alcohols or hemiacetals to the absorption liquids not only increases their capacity for the absorption of formaldehyde but also facilitates the removal of water from the formose mixtures which, in the continuous process, are continuously discharged from the absorption columns. The cause of this effect is the reduction in the viscosity of formose. The reaction products can be dehydrated under milder conditions in a vacuum or in thin layer evaporators. Due to the low viscosity of such a modified formose, it may be mixed with substantial quantities of fillers such as polymethyleneureas (aminoplast condensates), hydrates of alumina, cryolite, calcium carbonate, silicates, quartz powder, calcium sulphate, antimony oxides, melamine-formaldehyde condensates, dicyandiamide condensates and dyes. The use of basic hemiacetals in the absorption liquid greatly increases the reactivity of the resulting formose-polyol mixtures towards polyisocyanates.

In addition to the hydroxyaldehydes and hydroxyketones which are capable of enediol formation, from 1 to 50% by weight, preferably from 5 to 20% by weight of aldehydes or ketones which have no hydroxyl groups on the carbon atom in the α-position may be added to the absorption liquid. If these aldehydes or ketones contain hydroxyl groups on other carbon atoms, they are capable of hemiacetal formation and of subsequent aldol condensation. A cross Cannizzaro reaction is also possible on the aldehyde groups. Examples of such aldehydes and ketones include acetaldehyde, acetone, propionaldehyde, butyraldehyde, isobutyraldehyde, methyl ethyl ketone, cyclopentanone, cyclohexanone, mesityloxide, isophorone, acetophenone and their methylol derivatives which can be obtained by basic catalyzed partial or complete aldolization with formaldehyde on the carbon atom in the α-position to the keto group. The following formulae represent examples of such compounds:

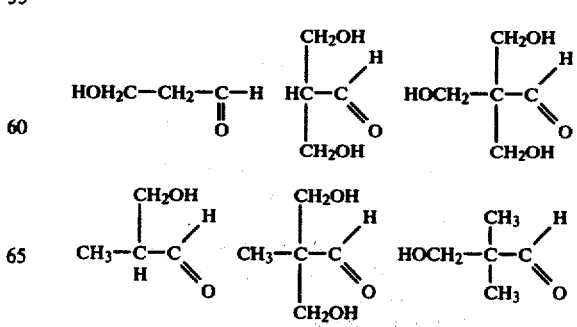

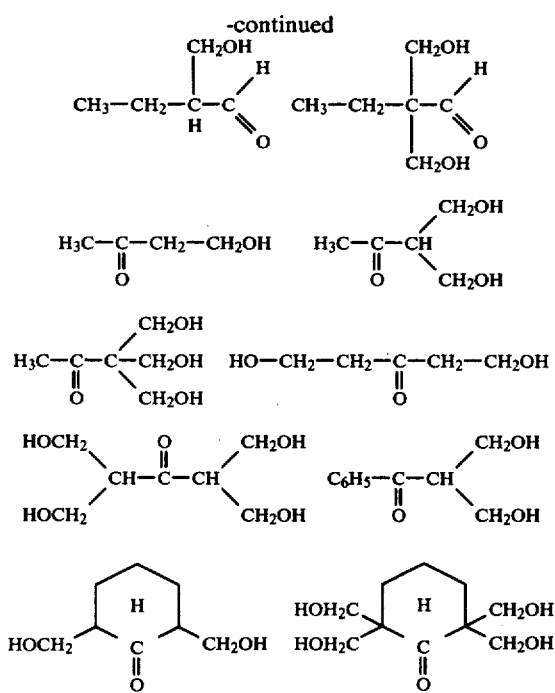

By-products from the commercial production of trimethylolpropane from butyric acid and formaldehyde, such as 2-ethylacrolein, may also be added to the absorption liquids. 2-Ethylacrolein, for example, is converted into 2,2-dimethylolalkanol in the presence of tertiary amine catalysts such as triisobutylamine in accordance with the following reaction scheme:

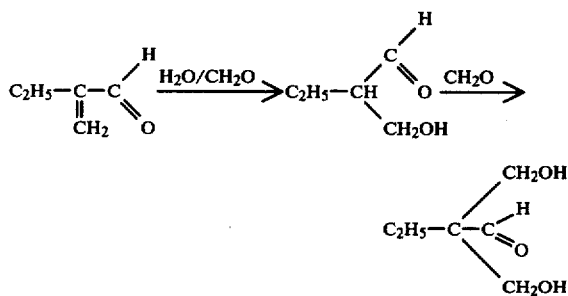

These methylolated aldehydes and ketones also bring about an advantageous reduction in the viscosity of the formoses prepared according to the invention.

According to another preferred variation of the process of the invention, from 1 to 50% by weight, preferably from 10 to 40% by weight of compounds which are capable of aminoplast formation may be added to the absorption liquid. Examples of such compounds include urea, symmetrically or asymmetrically substituted ureas such as N,N-dimethylurea (or-diethyl or -dibutyl urea), thiourea, dicyandiamide melamine, oxamide, ethylene urea, ε-caprolactam, pyrrolidone-(2), acetylene diurein and the N-methylol compounds of all these aminoplast monomers. Urea and ε-caprolactam are particularly suitable for this purpose.

As is known, in the presence of water and formaldehyde, the aminoplast formers mentioned above are in equilibrium with the corresponding N-methylol compounds. At the pH ranges observed according to the invention, the dissociation equilibrium is established so rapidly that even the formaldehyde bound in the N-methylol group is quantitatively converted into formose. After their dehydration, the formose mixtures obtained by this variation of the process contain high concentrations of aminoplast monomers which have the advantageous effect of drastically reducing their viscosity. When such modified formoses are reacted with polyisocyanates in the presence of blowing agents, they give rise to rigid polyurethane foams which are highly flame resistant.

By the addition of catalytic quantities of cyanides, for example sodium cyanide, copper-(I)cyanide, potassium cyanide, calcium cyanide or lead-(II) cyanide, the formoses prepared according to the invention can be enriched with keto sugars which are formed by acyloin condensation. Products containing increased proportions of sugars having from 7 to 10 carbon atoms are thereby obtained. The quantity of cyanide used for this purpose is preferably from 0.05 to 1%, based on the reaction mixture.

Various tertiary amines may also be added at relatively high concentrations, 0.2 to 8% by weight, preferably 1 to 3% by weight, based on the total reaction mixture, during or after formation of formose. This is done, particularly when working up the products of the process, if it is desired to bring about rearrangement reactions and dehydration reactions of formose to produce reddish or reddish brown caramelized sugars. Relatively high molecular weight sugars with conjugated double bonds of the kind which have already been described above as possible cocatalysts for the process according to the invention are obtained by this variation of the process. Such caramelized sugars are particularly suitable for the manufacture of flame resistant polyurethane foams.

Any synthesis gases obtained from the commercial production of formaldehyde may be used for the process according to the invention. Industrial processes for the manufacture of formaldehyde include, for example, the dehydration of methanol or the oxidation of methanol on suitable catalysts, for example silver or iron molybdenum oxide, in the presence of air, optionally steam and formaldehyde waste gases. Another method is the oxidation of methane or ethylene or higher olefines or dimethylether with air or oxygen or oxygen-containing gases on suitable catalysts. These commercial synthesis gases generally contain as their main component 20 to 70 volume % of nitrogen, 1 to 20 volume % of formaldehyde, 1 to 10 volume % of carbon dioxide and in most cases, depending on the particular manufacturing process, substantial quantities of water vapor. The remaining components are air, carbon monoxide, hydrogen and residues of starting products or of by-products such as methanol, methane, ethylene, higher olefins, methylformate, dimethylether and acetals and hemiacetals of formaldehyde. The residue of oxygen which may still be present in a synthesis gas may be used directly as the oxidizing agent in any variation of the process according to the invention in which the cocatalyst is to be obtained in situ by the oxidation of polyols which have at least two hydroxyl groups on adjacent carbon atoms. In many cases, however, the formose mixtures tend to undergo reactions which cause brown discoloration in the presence of oxygen. Synthesis gases which are free from oxygen are therefore preferred according to the invention.

The synthesis gases obtained from the industrial production of formaldehyde may also be used in the crude state for the process according to the invention, that is to say without prior purification. This is particularly advantageous for economic reasons. As already explained above, it is surprisingly found that the large quantities of carbon dioxide normally present in synthesis gases do not interfere with the formation of formose.

As repeatedly mentioned above, the present process may be carried out either intermittently or, preferably, continuously. In either case, the absorption liquid may still be free from catalyst but preferably already contains the metal catalyst in a dissolved or suspended form. The present process is generally carried out at normal pressure. If, in view of the particular purpose for which the end product is to be used, it is desired to bring about pronounced caramelizing reactions and other secondary reactions such as molecular rearrangements or sugar condensations, the process may be carried out at elevated pressures and temperatures of from 110° to 150° C. The elevated pressures used for this purpose are preferably 5 to 150 bar, in particular 10 to 70 bar. However, the process according to the invention may, of course, also be carried out at reduced pressure with chilled synthesis gases. The temperature of the absorption liquid is generally from 70° to 110° C., preferably from 80° to 100° C. but in special cases it may be preferred to carry out the formation of formose at lower temperatures, e.g. from 10° to 55° C., preferably from 15° to 50° C. The synthesis gases are generally introduced into the absorption columns at a temperature of about 90° to 250° C., preferably 100° to 140° C. A saving in energy can be obtained by using the heat stored in the synthesis gases, which are chilled to about 300° C. during their productions and/or the heat liberated in the formation of formose, for the partial dehydration of the products of the process. A considerable advantage in this respect is the fact that the large volumes of inert gas present in the synthesis gas act as carriers for water. Instead of using the heat liberated in this way, it may be supplied to various cycles of the production of formaldehyde, for example the evaporator cycles for methanol and/or water, so that optimum use can be made of the thermal energy obtainable from the manufacture of formaldehyde or the formation of formose.

In the discontinuous variation of the process, the synthesis gas is passed through a column which is filled with stationary absorption liquid. To accelerate the exchange of material between the two phases, the absorption column preferably contains packing bodies of known kind which have a large surface area, e.g. Raschig rings, saddle rings, sieve bottom plates or fine wire mesh. The solid catalysts based on ion exchangers, which are the preferred catalysts according to the invention, may, of course, also serve as packing in the absorption column. The synthesis gas is passed through the absorption column until the absorption liquid is saturated, i.e. until substantial quantities of formaldehyde leave the top of the column together with the inert gases. The absorption liquid preferably already contains the catalyst required for the process according to the invention, so that the formation of formose can already begin at the formaldehyde absorption stage. The advantage of this method is that it allows a given volume of absorption liquid to absorb a larger quantity of formaldehyde. If desired, however, the process according to the invention may, of course, be carried out by conducting the synthesis gases into a catalyst-free absorption liquid until the liquid is saturated and only then adding the catalyst to start the reaction.

As already mentioned above, however, it is most economical to carry out the process according to the invention continuously. In that case, the absorption liquid is kept in circulation and preferably passed in countercurrent to the hot synthesis gases. In this preferred variation of the process, it is also advantageous, in order to facilitate mass transfer, to use absorption columns in the form of the known packing columns, bubble tray columns, sieve plate columns or trickle film columns. Bubble columns may, of course, also be used for the process of the invention. Both in the continuous and in the discontinuous variation of the present process, the average residence time of the formaldehyde-containing synthesis gases in the absorption columns is generally between 0.3 and 10 seconds, preferably between 0.6 and 3 seconds.

FIG. 1 is a highly simplified schematic representation of an apparatus suitable for continuously carrying out the process of the invention. Hot synthesis gas containing formaldehyde is introduced at 1 into absorption column A which is filled with absorption liquid. Additives such as catalysts, oxidizing agents, bases, alcohols, aldolizable aldehydes or ketones, aminoplast formers, etc. may be fed in at 2. Absorption liquid is kept in circulation by pump B and carried in countercurrent to the synthesis gas. The gases containing water vapor but freed from formaldehyde leave the absorption column at 3. A heatable and coolable residence vessel in which the formation of formose can take place is represented at C. Part of the absorption liquid containing formose and residues of formaldehyde is continuously discharged at 4 and transferred to another residence vessel D in which various additives (catalysts, bases, acids, aminoplast formers, etc.) may again be added at 5. The reaction product leaves the apparatus at 6.

In the continuous variation of the process, the catalyst may also be added to the absorption liquid itself, as already mentioned above, so that the absorption of formaldehyde and the condensation of formaldehyde to formose take place simultaneously, but alternatively, the catalyst may be added after removal of the product (for example, at position 5 of FIG. 1), so that the formation of formose takes place mainly outside the circulation.

In the continuous variation of the process according to the invention, a distinction should be made between the starting phase and the stationary state. During the starting phase of the process, synthesis gas is conducted through the absorption liquid which is kept in circulation by the pump and which contains the cocatalyst, water, optionally monohydric or polyhydric alcohols, the catalyst and other additives in the proportions indicated above. During this starting phase, the concentration of free formaldehyde and in some cases (if catalysts are present in the absorption liquid) of formose increases until a flow equilibrium is eventually established between the quantity of formaldehyde introduced by the synthesis gas and the reaction product remove from circulation. The duration of this starting phase depends not only on the volumes of the absorption column, pump, conduits and, where used, residence vessels, but also, to a major extent, on the initial composition of the absorption liquid. The starting phase can be considerably shortened if as much formose and aqueous formalin solution as corresponds to the stationary state is added to the absorption liquid from the beginning. The cocatalyst solution is therefore advantageously mixed with an approximately 30 to 60% by weight hot, aqueous formaldehyde solution before it is used as absorption liquid. It is surprising to find that 60% by weight formaldehyde solutions, which are normally completely unstable, can be mixed with aqueous solutions of formose or invert sugar without even traces of insoluble, $\alpha,\omega$-dihydroxypolyoxymethylene (paraformaldehyde) precipitating out.

The starting phase may last from a few seconds to about 2 hours, in most cases from 1 to 60 minutes, depending on the initial composition of the absorption liquid and the dimensions of the reactor.

Owing to the extremely high absorption capacity of the cocatalyst solutions for formaldehyde, particularly if they contain formose and/or other sugars and/or alcohols, and the very rapid condensation of formaldehyde to formose, extremely large volumes of formaldehyde-containing synthesis gas can be used per unit volume of absorption liquid and unit time. For example, it is quite possible to conduct approximately 20 cubic meters of synthesis gas, containing about 4 m$^3$ of formaldehyde, through an approximately 50% aqueous formose solution circulating at the rate of 30 liters per hour without the exhaust gases at the head of the absorption column containing significant quantities of free formaldehyde (see Example 1).

The stationary formaldehyde concentration in the absorption liquid depends, of course, on the selected variation of the process (formation of formose either simultaneous with formaldehyde absorption or only after the absorption liquid leaving the absorption apparatus) and on the parameters of the process (volume of synthesis gas introduced per unit time; total volume of absorption liquid; average residence time of the absorption liquid in the absorption column; concentration of catalyst or cocatalyst in the absorption liquid; use of alcohols in the absorption liquid; temperature; pressure). As a general rule, however, the stationary formaldehyde concentration in the absorption column, when catalysts are used in the absorption liquid, is in the region of about 0.5 to 10% by weight, preferably between 1 and 5% by weight. If catalyst is added only outside the circulation of absorption liquid, the stationary formaldehyde concentration in the circulation is, of course, higher. Under these conditions it is about 2 to 70% by weight, preferably 10 to 50% by weight.

The concentration of formose in the absorption liquid similarly depends on the selected variation of the process. If the absorption liquid already contains a metal catalyst, so that the formation of formose and absorption of formaldehyde takes place simultaneously, the absorption liquid may advantageously be adjusted to a formose content of approximately 20 to 90% by weight, preferably 30 to 70% by weight, most preferably 40 to 60% by weight. If the catalyst is added only after the circulation of absorption liquid, the liquid may contain relatively small quantities of cocatalyst, i.e. at least 0.1% by weight, preferably more than 3% by weight, most preferably more than 5% by weight. The absorption liquid also in that case preferably already contains as large a quantity as possible of formose and/or monohydric or polyhydric alcohols so that the reaction product is obtained in a highly concentrated form.

In the stationary state, if the process is carried out within the preferred temperature range of approximately 80° to 100° C., about one third of the water from the synthesis gas is evaporated by the heat of reaction liberated or carried away by the inert gases. The remainder of the water from the synthesis gases provides for a constant concentration of formose in the absorption liquid within the preferred limits indicated above. Once the stationary state is reached, the only substances which need to be added to the circulation, apart from synthesis gas, are an inorganic or organic base to maintain the required pH and, if indicated, catalyst, alcohols and other additives at the rate at which they are continuously removed from circulation with the reaction products.

In the preferred variation of the continuous process, in which formaldehyde absorption and formose formation take place simultaneously, the pH in the absorption liquid may vary within wide limits. The liquid is generally maintained at a pH of 3 to 10, preferably between 6 and 8. Side reactions, e.g. acetalization, occur at low pH values (pH below 4.5). This low pH is therefore normally avoided although it may in special cases be suitable for deliberately producing such modified formoses. It is surprising that the process according to the invention can also be carried out at a slightly alkaline pH without any significant tendency of formose to enter into reactions which cause brown discoloration.

The simultaneous absorption condensation of formaldehyde to formose preferably takes place at normal pressure at the boiling point of the reaction mixture. This has the advantage, as already mentioned above, that the high thermal energy of formose formation (which amounts to about 6.6 kilogram calories per mol of formaldehyde), as well as the carrier action of the inert gases can be used to distil off considerable quantities of water at the head of the absorption column. Formose solutions can then be concentrated with little consumption of energy. Aqueous formose solutions at concentrations of 60 to 80% by weight still have very low viscosities, particularly if they are mixed with hemiacetals or any of the other viscosity reducing additives mentioned above. They can easily be pumped through the cycle and can conveniently be freed from metal catalyst in anion exchangers. The discharged hot waste gases, which contain water vapor, may be used as they are for heating methanol or methanol/water mixtures required for the production of the synthesis gases in the formaldehyde reactors. The process according to the invention thus makes it possible to produce formose extremely economically by making use of the thermal energy in the synthesis gases as well as the heat of reaction of formose formation.

The present process may also be carried out at pressures within the range of approximately 10 to 400 mbar, preferably 12 to 20 mbar. The synthesis gases containing formaldehyde may be passed through the absorption column in the opposite direction to the absorption solution which has been heated to the reduced boiling temperature, approximately 45° to 55° C. The advantage of this variation of the process is that the exhaust gases in this case contain very large quantities of water and an extremely small quantity of residual formaldehyde. To compensate for the reduced velocity of formose formation when this procedure is employed, the formose solutions still containing relatively large quantities of formaldehyde may subsequently undergo further condensation at normal pressure, outside the circulation, in a cascade of stirrer vessels or in a continuous flow reaction tube until the desired formaldehyde conversion has been reached.

When normal pressure is employed, the average residence time of the absorption liquid may in similar manner be kept so short that the formaldehyde originally in the synthesis has is not completely converted into formose within the circulation, but only to an extent of about 30 to 50% by weight. For example, the remaining formaldehyde can be subsequently converted into formose in a reaction vessel (D in FIG. 1) placed outside the circulation.

For special purposes, for example if formose is to be used as a source of carbohydrate for microorganisms, the formose should contain mainly polyhydroxyaldehydes and polyhydroxyketones having free, not yet reduced aldehyde or keto groups or their cyclohemiacetal forms. In that case, it is advantageous to maintain a much lower temperature, preferably 10° to 50° C., during absorption of formaldehyde from the process gases in the process according to the invention. Subsequently the resulting solutions, which still contain relatively large residues of formaldehyde can be condensed in a separate reactor outside the circulation of absorption liquid, at approximately 30° to 55° C. Reduction reactions due to crossed Cannizzaro reactions can be greatly suppressed by this method.

As already explained above, if the absorption liquid contains no catalyst, the hemiacetals of the hydroxyl compounds in the absorption liquid are first formed in equilibrium with the formaldehyde dissolved in water, for example as represented by the following formulae:

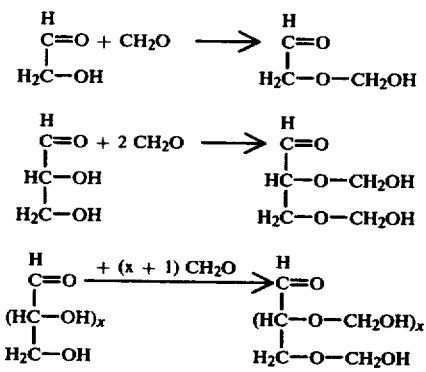

Since the dissociation equilibrium between these hemiacetals and free formaldehyde is established very rapidly in the presence of water, formose is also formed very rapidly from such mixtures after the addition of metal catalyst at 70° to 110° C., preferably at 80° to 100° C. The polyhydroxyaldehydes and polyhydroxyketones which are formed by the dissociation of the hemiacetals and which are capable of enediol formation develop their full cocatalytic activity.

In the variation of the process of the invention in which formaldehyde absorption and formation of formose take place one after the other, the pH is adjusted by the controlled addition of metal catalyst and continuous addition of small quantities of inorganic or organic bases, preferably to approximately 6.0 to 8.5, in particular 6.4 to 7.0, up to a formaldehyde conversion of 10 to 60%, preferably 30 to 50%, and thereafter to 4.0 to 6.5, preferably 5 to 6 until termination of the condensation reaction. A similar profile of the pH in the system, particularly in the residence vessel C of FIG. 1, can, of course, also be adjusted in the particularly preferred variation of the process, in which formose formation takes place continuously in the absorption liquid, by adding bases under controlled conditions at various points in the circulation of the absorption liquid.

If all or part of the formation of formose takes place outside the circulation of absorption liquid, the reaction may be carried out according to the invention in continuously operating cascades of stirrer vessels. The residual formaldehyde content can be exactly adjusted in this variation of the process by varying the residence time in the individual stirrer vessels of the cascade. The distribution of products in the reaction mixture and the average hydroxyl functionality of the mixture of polyhydric alcohols obtained from the reaction mixture by reduction can thus easily be varied within wide limits and in a reproducible manner. According to the invention, the condensation of formaldehyde to formose may be carried out in coiled reaction tubes under pressure, about 5 to 150 bar, preferably 10 to 70 bars, at elevated temperatures, preferably 105° to 140° C., instead of in cascades of stirrer vessels. When choosing suitable dimensions for the reaction coil it is, of course, necessary to take into account the cubic coefficients of expansion of the formose mixtures which are to be formed in order to avoid the development of excessively high fluid pressures.

Suitable reaction coils have been described for example, in German Auslegeschriften Nos. 1,667,051 and 1,921,045.

Any inorganic or organic bases may be used according to the invention to control the pH. The inorganic bases used are preferably oxides or hydroxides of alkaline metal and/or alkaline earth metals, most preferably sodium and potassium hydroxide. Urotropine, pyridine, secondary and tertiary amines and the so-called crown ether complexes of alkali metals are examples of suitable organic bases. Triethylamine, tri-n-butylamine, dimethylbenzylamine, diethylaminoethanol, hexahydrotriazines of primary aliphatic or cycloaliphatic amines and formaldehyde, and ethoxylation and propoxylation products of ethylene diamine, cyclohexylamine, aniline, etc. are examples of suitable tertiary amines.

Molecular rearrangement or caramelization reactions can be deliberately produced during or after the formation of formose by adding excess quantities of the above mentioned hydroxides or organic bases in order to obtain yellow to reddish brown sugar derivatives as already discussed above in connection with the cocatalyts. A pH of about 7.5 to 10.5, preferably 8.5 to 10, should generally be maintained for this purpose. Caramelized sugars produced in this way are valuable starting materials for the production of flame resistance polyurethane foams.

Conversely, the product mixtures may be acidified, to pH values of about 1 to 3, during or after the formation of formose, in which case intramolecular or intermolecular acetals are formed with elimination of water in accordance with the following reaction scheme, optionally in the presence of boric acid as catalyst:

Intramolecular acetal formation (idealized):

-continued

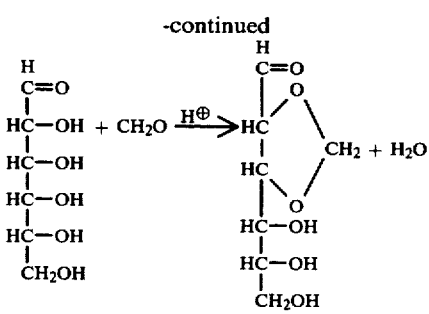

Intermolecular acetal formation (idealized):

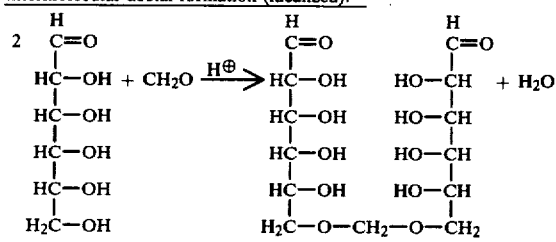

Such end products which have been modified by acetal formation have the advantage of having lower viscosities, which substantially improves their miscibility or emulsifiability with the higher molecular weight polyhydroxyl compounds used for polyurethane production.

As already mentioned above, the formation of formose releases large quantities of heat of reaction. The absorption solution can therefore be kept lightly boiling during the whole reaction time without external heat supply. If the reaction is carried out at a basic pH or in the presence of large quantities of catalyst or cocatalyst, larger quantities of heat are produced and lead to more vigorous boiling. The excess heat can easily be removed by external cooling. Within the preferred pH range indicated above, the reaction velocity is advantageously sufficiently low to allow the reaction to be stopped whenever desired by external cooling or the addition of acids in order to obtain a particular residual formaldehyde content or distribution of products. Within the given preferred pH range of 5 to 7, the reaction velocity can easily be controlled by slight changes in pH.

Particularly when the preferred catalysts are used (calcium and lead compounds), relatively high molecular weight polyol, hydroxyaldehydes and hydroxyketones, mainly having 5 and 6 carbon atoms, are obtained according to the invention without unwanted colored by-products if the condensation reaction of formaldehyde is continued to a residual formaldehyde content of from 0 to 1.5% by weight before the reaction is stopped by cooling and/or inactivation of the catalyst. The product mixtures obtained under these conditions are substantially free from formaldehyde. It is surprisingly found that even when formaldehyde is converted almost quantitatively in this way, the unwanted Cannizzaro reaction of formaldehyde with itself (disproportionation into methanol and formic acid), which reduces the formation of hydroxyaldehydes and hydroxyketones, is to a large extent prevented.

If, however, the condensation of formaldehyde is not complete but is interrupted at residual formaldehyde contents of between 0 and 10% by weight, preferably between 0.5 and 6% by weight, all of the various product distributions required for different fields of application can be obtained. As shown by gas chromatographic analysis of the hydrogenated and silylated product mixtures obtained in this way, the distribution of products obtained with a particular residual formaldehyde content and a particular pH profile is completely reproducible both with regard to the compounds which have from 2 to 4 carbon atoms and with regard to the compounds having 5 or more carbon atoms. This was not to be expected in view of the large number of reactions which take place simultaneously and side by side during the condensation of formaldehyde, only a few of which have been described above by way of example.

If, for example, the synthesis of formose is stopped when the reaction mixture still contains 8% by weight of free formaldehyde, the resulting product contains only a very small proportion of compounds having 6 or more carbon atoms (approximately 7% by weight), whereas the proportion of compounds which contain 2 hydroxyl groups after reduction is increased to about 15% by weight, the proportion of compounds having three hydroxyl groups in the reduced form is increased to about 20%, the proportion of compounds with 4 hydroxyl groups to 30% and the proportion of compounds with 5 hydroxyl groups to about 25%.

As will be explained more fully below, the residual formaldehyde content in the reaction mixtures can be used for numerous secondary or modification reactions with formose and/or other additives. Formaldehyde may, of course, also be added in controlled quantities for this purpose, for example in the form of aqueous solutions.

The formose solution may be post-treated, for example with the addition of an inorganic base and, optionally, excess formaldehyde at a pH of from 9 to 13, preferably 10 to 11 and a temperature of from 10° to 100° C., preferably 30° to 60° C., for a period which may vary from about 30 minutes to 12 hours. The crossed Cannizzaro reaction which takes place under these conditions reduces the carbonyl groups to hydroxyl groups. The inorganic bases used for this purpose are preferably hydroxides of sodium, potassium, calcium or barium and crown ether complexes of alkali metal atoms. The reducing reaction may be further accelerated by catalysts. The catalysts used for this purpose are preferably oxalates of transition metals, in particular of nickel, cobalt, iron, cadmium, zinc, copper chromium or manganese, and the said transition metals in their elementary form. Activated nickel used in the form of so-called Raney nickel and elementary zinc in the form of powder are particularly preferred. Other suitable catalysts according to the invention for the crossed Cannizzaro reaction are organic acid amides such as formamide, dimethylformamide and acetamide and tetraalkylammonium salts, in particular tetramethyl and tetraethylammonium chloride.

Aldol and dehydration reactions of formose to higher molecular weight and branched chain products take place in parallel with the crossed Cannizzaro reaction. In particular, the methylolation of carbon atoms in the α-position to the carbonyl group by aldol condensation with formaldehyde takes place as a side reaction even during the formation of formose, so that approximately 10 to 15% by weight of the formose consist of branched chain products. When lead catalysts are used, which are preferred according to the invention, this methylolation reaction in situ mainly takes place only at pH values above 7. This α-methylolation increases the functionality and isocyanate reactivity of the products of the process since it introduces additional primary hydroxyl groups into the formose. These aldolization reactions proceed via the open chain forms of sugars, which are in equilibrium with the cyclohemiacetals of the sugars.

According to the invention, this α-methylolation may be accelerated in the form of a heterogeneous catalysis by the addition of moderately basic to strongly basic ion exchangers. The caramelization reactions of sugars which normally occur at relatively high pH values are strongly suppressed and the acids formed during the synthesis of formose are partly bound.

The above described post-treatment of formose in the presence of formaldehyde in a basic reaction medium to bring about aldol condensations and/or cross Cannizzaro reactions may, of course, also be carried out continuously in a reaction tube. To adjust the reaction volume to the required pH, the inorganic or organic base is introduced in the required quantity at one or more points of the tube. In this case, it is also possible to vary the distribution of products and hydroxyl functionality of the resulting polyhydric alcohols within wide limits by varying the throughflow times. A preferred tertiary base for controlled aldolization is triethylamine. If desired, the residual formaldehyde content of the formose solutions prepared according to the invention may also be bound by N- or C-methylolation reactions by the addition of aminoplast forming or phenoplast forming monomers, e.g. urea, oxamide, thiourea, dicyandiamide, ε-caprolactam, phenol or bisphenol A, or by the addition of aldehyde and ketones which are suitable for α-methylolation (for example acetaldehyde, propionaldehyde, butyraldehyde, isobutyraldehyde, methyl ethyl ketone or cyclohexanone) or the addition of ammonia. Secondary or primary amines which react with formaldehyde to form aminals or hexahydrotriazines may also be added. Some of these reactions are represented by the following reaction scheme:

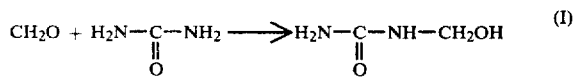

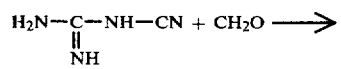

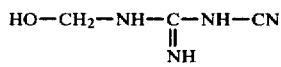

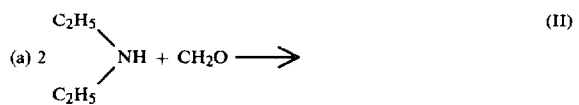

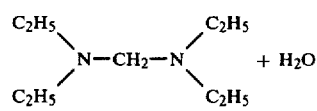

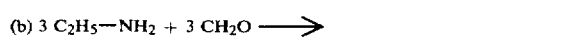

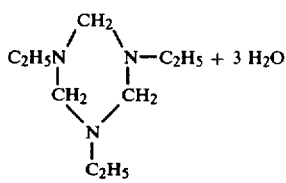

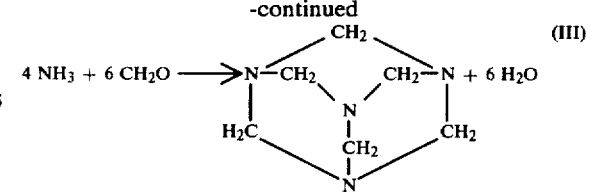

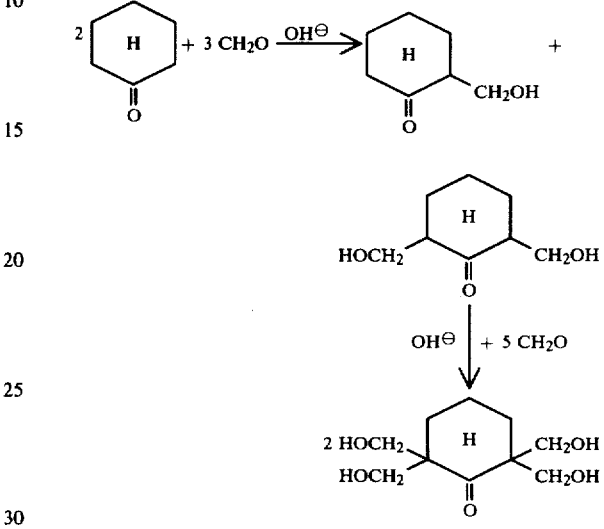

The N-methylol compounds formed according to reaction scheme I, in particular, may be dissolved in high concentrations in the dehydrated products of the process, partially with etherification with the polyhydroxyaldehydes or ketones taking place. Such modified formoses are the preferred starting products for the production of extremely flame resistant polyurethane foams. The above described methylolation of cyclohexanone, and the corresponding methylolation reactions of the aforesaid aldehydes, progress substantially more rapidly than the α-methylolation of formoses since the aldehyde and keto groups in the formoses are for the most part blocked by cyclohemiacetal or ketal formation.

Another method of trapping the residual formaldehyde in the products produced according to the invention consists of adding alkyphosphites such as diethylphosphite or dimethylphosphite, preferably in an amount of from 1 to 30% by weight, most preferably 2 to 20% by weight, based on the reaction mixture. A basic catalyzed reaction then results in the formation of α-hydroxymethylphosphonic acid esters or transesterification products with the hydroxyl groups of the formoses. Other CH-acidic compounds such as malonic acid esters or acetic acid esters react in a similar manner. Formoses which are modified with alkylphosphites in particular are valuable starting materials for the production of extremely flame resistant polyurethane foams.

It is particularly surprising that formoses according to the invention in any molecular distribution dissolve in the above mentioned phosphites to form clear solutions whereas glucose and other monosaccharides as well as sucrose are insoluble in phosphites. It has surprisingly been found that the solutions obtained have much lower viscosities than solutions of unmodified formoses and they are more readily emulsifiable or miscible with various low molecular weight and higher molecular weight polyhydroxyl compounds.

In formoses which have been modified with dialkyl phosphite, equilibria are established between free dialkyl phosphite, hydroxymethanephosphonic acid esters having the constitution represented by the following formula

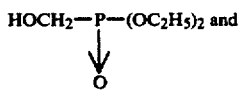

α-hydroxyphosphonic acid esters of the following constitution

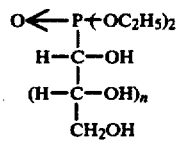

n = 0–6 the equilibria depending on the temperature. At elevated temperatures, higher than about 35° C., and particularly in the presence of catalytic quantities of inorganic bases or, better still, tertiary amines such as triethylamine or dimethylbenzylamine, these compounds undergo rearrangement reactions and trans-esterification reactions accompanied by the splitting off of alcohol. Cyclic phosphites of the formoses, or higher molecular weight polyphosphites, or formose esters of hydroxymethyl phosphonic acid are formed by intermolecular linkage of formoses. Any degree of transesterification can be obtained, depending on the quantity of alcohol split off, and the viscosities can thus be adjusted to values ranging, for example, from about 300 mPas at 20° C. to about 110,000 mPas at 20° C.

Since the formaldehyde-containing synthesis gases used according to the invention generally contain large quantities of molecular hydrogen, mostly about 6 to 7 volumes percent, the formoses may be treated with the exhaust gases still containing free hydrogen at an elevated temperature and under pressure, about 80° to 100° C. and 60 to 150 bar after the reaction products have been desalted.

Under these conditions, some of the aldehyde and keto groups in the products of the process may be reduced to hydroxyl groups in the presence of the usual hydrogenation catalysts such as, for example, Raney nickel. In a continuously operating plant using a conventional synthesis gas it is typically possible, for example, to treat about 100 kg of formose, containing about 400 carbonyl equivalents, with about 1200 equivalents of hydrogen from the formaldehyde-free exhaust gases per unit time.

It has already been indicated above that the absorption of formaldehyde in cocatalyst solutions and the subsequent irreversible conversion into formose proceed so rapidly that, in the process according to the invention, the synthesis gases are already almost quantitatively freed from formaldehyde by one passage through an absorption column. If desired, however, a plurality of absorption towers may be arranged in series in the process according to the invention in the same way as in conventional processes used for obtaining aqueous formaldehyde solutions from synthesis gases which contain formaldehyde. Even the slightest traces of formaldehyde are converted then into formose.

If desired, the process according to the invention may, of course, be combined with the recovery of formose from aqueous formaldehyde solutions. This may be done, for example, by using the formoses prepared by any method from aqueous formaldehyde solutions as cocatalysts for the process according to the invention.

Summarizing, it is found that the process according to the invention for preparing formoses provides the following important advantages over known processes:

1. The process according to the invention is extremely economical. By using the preferred absorption liquids containing from 10 to 80% by weight of cocatalyst, formoses of various compositions can be prepared reproducibly, rapidly, in quantitative yields and with low equipment cost from synthesis gases obtained from any formaldehyde production plants.

2. In the process of the invention, the thermal energy in the formaldehyde-containing synthesis gases, the heat of reaction produced in the formation of formose, and the capacity of the large volumes of inert gas to act as carriers for water can be optimally utilized for heating the absorption liquid, heating the methanol or methanol/water mixture for the preparation of formaldehyde, and for removing water by distillation from the resulting formose solutions at normal pressure, slight excess pressure or under vacuum, optionally by thin layer distillation.

3. By the process of the invention, it is possible to prepare mixtures of hydroxyaldehydes, hydroxyketones and polyhydric alcohols in which the proportion of polyhydric alcohols produced by crossed Cannizzaro reaction, is from 30 to 75% by weight. The molecular weight distribution and hydroxyl functionality of these products can be adjusted as desired according to the purposes for which the products are to be used. The results are reproducible. In particular, it is possible to prepare mixtures containing more than 90% by weight of compounds which have more than 4 carbon atoms. With suitable control of pH, these products are obtained colorless and are without unwanted decomposition products. After desalting, they can be hydrogenated without further purification. The product mixtures need not be isolated by distillation.

4. The condensation of formaldehyde to formose according to the invention may be carried out within a wide range of temperatures and pressures. The process according to the invention can also be carried out with a wide range of catalysts or mixed catalysts (almost any metal compounds as well as ash residues form biomasses and plant ashes) and cocatalysts (any formoses; oxidation products of polyhydric alcohols; artificial and natural invert sugars; honeys; hydrolysates of various polysaccharides and of vegetable materials and biomasses). The viscosity and miscibility of the products of the process and their compatibility with other polyhydroxyl compounds can be controlled by using hemiacetals of these cocatalysts as absorption liquids.

5. By adding monohydric alcohols and preferably polyhydric alcohols or their formaldehyde hemiacetals, the absorption capacity of the absorption liquids for formaldehyde obtained from the process gases can be greatly increased. The viscosity of the end products can be varied within wide limits and adapted to the particular purpose for which they are intended.

6. The process according to the invention makes it possible for the hydrogen present in the synthesis gas to be utilized for the reduction of keto and aldehyde groups in the sugar mixtures obtained.

7. In the process according to the invention, the preferred lead catalysts for formose formation can be used again either immediately, in the case of the solid bed catalysts mentioned above, or after a simple working up process, so that there is no accumulation of ecologically harmful lead waste.

8. Formoses modified in various ways can be prepared according to the invention by varying the pH. Acidification to pH values of from 1 to 4, optionally in the presence of orthoformic acid esters as water binding agents, causes the formose molecules to undergo acetalization and ketalization reactions with each other and/or with formaldehyde and/or with any monohydric or polyhydric alcohols added. In the basic pH range, the formoses can be reduced by a crossed Cannizzaro reaction with formaldehyde or with other low molecular weight aldehydes or ketones or their methylolation products. Alternatively this method can be used for varying the viscosity of the formoses and their miscibility with other polyhydroxyl compounds. Controlled methylolation in the α-position to the keto or aldehyde group in the polyhydroxyaldehydes and ketones obtained according to the invention is also possible. Branched products with increased hydroxyl functionality are thereby obtained. In this connection, it is particularly advantageous to add triethylamine or strongly basic ion exchangers to the absorption solution. This has the effect of keeping the pH constant during the reaction since small quantities of formic acid, lactic acid, saccharic acids, etc. formed during the reaction are bound to the matrix. The method therefore has the advantage of obviating the necessity to add large quantities of inorganic or organic bases. The formoses obtained are substantially acid-free and very easily hydrogenated. A more strongly alkaline pH can be used according to the invention for the controlled production of strongly caramelized sugar mixtures.

9. By adding compounds which have hydrogen atoms in the α-position to an aldehyde or keto group, it is possible to combine the synthesis of formose with the methylolation of these aldehydes and ketones. The properties of the product, such as their viscosity, miscibility with polyhydroxyl compounds, etc. can be varied within wide limits. In this connection it is particularly advantageous to use sterically hindered soluble amines such as diisobutylamine, triisobutylamine, diisopropylamine N,N-dimethylcyclohexylamine or N-methyl-isopropylcyclohexylamine, because the α-methylolation reaction then takes place substantially without interference from a Cannizzaro or crossed Cannizzaro reaction.

10. The addition of any alkylphosphites or α-hydroxymethylphosphonic acid esters to the products of the process is also of particular interest because it brings about the trans-esterification to polyphosphorous acid esters or partially saponified polyphosphorous acid esters of formoses. The viscosity of the formoses is greatly reduced and the polyurethane resin produced from the formoses are rendered flame resistant.

11. By coupling the formose synthesis with the N-methylolation of ureas and various monomers suitable for aminoplast or phenoplast formation (ε-caprolactam, oxamide, bisurethanes, phenols, naphthols, bisphenol A, phenol sulphonates and naphthol sulphonates) new mixtures of substances which are of interest for the production of extremely flame-resistant polyurethane foams and which can be converted by a simple process of acidification into sugar-aminoplast condensates or sugar-phenol condensates can be obtained by a continuous one pot process.

12. With suitable choice of residence times for the absorption liquid, the continuous process of formose synthesis can be interrupted at any point in the cycle. If desired, the subsequent reaction can be shifted to continuously operating reaction tubes or cascades of stirrer vessels outside the cycle. It is therefore possible to carry out the final stages of formose formation under very mild conditions, employing long reaction times and low temperatures and, if necessary with careful dehydration in a thin layer evaporator. These mild conditions result in formose mixtures which are distinguished by exceptionally high equivalents of carbonyl and aldehyde groups.

13. According to the invention, the residual formaldehyde need not be removed by distillation or degasification at elevated temperatures but can simply be bound by virtually spontaneous methylolation reactions of aldehydes, aminoplast and phenoplast formers, dialkylphosphites, CH-acidic compounds, ammonia, aniline and other primary or secondary amines. This results in modified formoses which are highly reactive with isocyanates and capable of forming flame-resistant polyurethane foams.

The present invention thus also relates to a process for the production of cellular or non-cellular polyurethane resins by the reaction of (a) polyisocyanates with (b) compounds containing at least two active hydrogen atoms and having a molecular weight of between 32 and 400, optionally (c) compounds containing at least two active hydrogen atoms and having a molecular weight of between 400 and 10,000 and optionally (d) blowing agents, catalysts and other known additives, in which process modified or unmodified formoses prepared according to the invention are used as component (b).

The polyisocyanates used as starting components according to the invention may be aliphatic, cycloaliphatic, araliphatic, aromatic or heterocyclic polyisocyanates such as those described, for example, by W. Siefken in Justus Liebigs Annalen der Chemie, 562, pages 75 to 136, for example ethylene diisocyanate, tetramethylene-1,4-diisocyanate, hexamethylene-1,6-diisocyanate, dodecane-1,12-diisocyanate, cyclobutane-1,3-diisocyanate, cyclohexane-1,3-and -1,4-diisocyanate and any mixtures of these isomers, 1-isocyanato-3,3,5-trimethyl-5-isocyanatomethylcyclohexane as described in German Auslegeschrift No. 1,202,785 and U.S. Pat. No. 3,401,190, hexahydrotolylene-2,4-diisocyanate and -2,6-diisocyanate and any mixtures of these isomers, hexahydrophenylene-1,3-diisocyanate and/or 1,4-diisocyanate, perhydrodiphenylmethane-2,4'-diisocyanate and/or 4,4'-diisocyanate, phenylene-1,3-diisocyanate and -1,4-diisocyanate, tolylene-2,4-diisocyanate and -2,6-diisocyanate and any mixtures of these isomers; diphenylmethane-2,4'-diisocyanate and/or 4,4'-diisocyanate, naphthylene-1,5-diisocyanate, triphenylmethane-4,4',4"-triisocyanate, polyphenyl-polymethylene polyisocyanates which can be obtained by aniline formaldehyde condensation followed by phosgenation and which have been described, for example, in British Pat. Nos. 874,430 and 848,671; m- and p-isocyanatophenyl-sulphonyl isocyanates according to U.S. Pat. 3,454,606 perchlorinated aryl polyisocyanates such as those described, for example, in German Auslegeschrift No. 1,157,601 and U.S. Pat. No. 3,277,138; polyisocyanates having carbodiimide groups as described in German Patent No. 1,092,007 and U.S. Pat. No. 3,152,162, diisocyanates of the kind described in U.S. Pat. 3,492,330, polyisocyanates with allophanate groups as described e.g. in British Pat. No. 994,890, Belgian Patent No. 761,626 and published Dutch Patent Application No. 7,102,524 polyisocyanates with isocyanurate groups, e.g. as described in U.S. Pat. No. 3,001,973, German Patents Nos. 1,022,789, 1,222,067 and 1,027,394 and German Offenlegungsschriften Nos. 1,929,034 and 2,004,048; polyisocyanates with urethane groups as described e.g. in Belgian Pat. No. 752,261 or U.S. Pat. No. 3,394,164; polyisocyanates with acylated urea groups according to German Patent No. 1,230,778, polyisocyanates with biuret groups as described e.g. in German Patent No. 1,101,394, U.S. Pat. Nos. 3,124,605 and 3,201,372 and in British Pat. No. 889,050, polyisocyanates prepared by telomerization reactions as described for example, in U.S. Pat. No. 3,654,106, polyisocyanates having ester groups such as those mentioned, for example, in British Pat. Nos. 965,474 and 1,072,956, U.S. Pat. No. 3,567,763 and German Patent No. 1,231,688 reaction products of the above mentioned isocyanates with acetals according to German Patent No. 1,072,385 and polyisocyanates containing polymeric fatty acid groups according to U.S. Pat. No. 3,455,883.

The distillation residues obtained from the commercial production of isocyanates and still containing isocyanate groups may also be used, optionally as solutions in one or more of the above mentioned polyisocyanates. Any mixtures of the above mentioned polyisocyanates may also be used.

As a general rule, it is particularly preferred to use commercially readily available polyisocyanates such as tolylene-2,4-diisocyanate and -2,6-diisocyanate and any mixtures of these isomers ("TDI"), polyphenylpolymethylene polyisocyanates of the kind which can be prepared by aniline formaldehyde condensation followed by phosgenation ("crude MDI") and polyisocyanates containing carbodiimide groups, urethane groups, allophanate groups, isocyanurate groups, urea groups of biuret groups ("modified polyisocyanates").

The starting components used according to the invention may also include compounds, generally with a molecular weight of 400 to 10,000, which have at least two hydrogen atoms capable of reacting with isocyanates. These compounds may contain amino groups, thiol groups or carboxyl groups but are preferably polyhydroxyl compounds, in particular compounds having from 2 to 8 hydroxyl groups, especially those with a molecular weight of from 800 to 10,000 and preferably 1,000 to 6,000, e.g. polyesters, polyethers, polythioethers, polyacetals, polycarbonates and polyester amides having at least 2, generally 2 to 8, but preferably 2 to 4 hydroxyl groups, of the kind known per se for the production of both homogeneous and cellular polyurethanes.

Suitable polyesters with hydroxyl groups include e.g. reaction products of polyvalent, preferably divalent alcohols, optionally with the addition of trivalent alcohols, and polyvalent, preferably divalent carboxylic acids. Instead of free polycarboxylic acids, the corresponding polycarboxylic acid anhydrides or corresponding polycarboxylic acid esters of lower alcohols or mixtures thereof may, of course, be used for preparing the polyesters. The polycarboxylic acids may be aliphatic, cycloaliphatic, aromatic and/or heterocyclic and they may be substituted, e.g. by halogen atoms, and/or unsaturated.

The following are mentioned as examples: Succinic acid; adipic acid; suberic acid; azelaic acid; sebacic acid; phthalic acid; isophthalic acid; trimellitic acid; phthalic acid anhydride; tetrahydrophthalic acid anhydride; hexahydrophthalic acid anhydride; tetrachlorophthalic acid anhydride; endomethylene tetrahydrophthalic acid anhydride; glutaric acid anhydride; maleic acid; maleic acid anhydride; fumaric acid; dimeric and trimeric fatty acids such as oleic acid which may be mixed with monomeric fatty acids; dimethyl terephthalate and terephthalic acid-bis-glycol esters. The following are examples of suitable polyvalent alcohols: Ethylene glycol, propylene glycol-(1,2) and -(1,3); butylene glycol-(1,4) and -(2,3); hexanediol-(1,6); octanediol-(1,8), neopentylglycol, cyclohexanedimethanol (1,4-bis-hydroxymethyl-cyclohexane), 2-methyl-1,3-propanediol, glycerol, trimethylol-propane, hexanetriol-(1,2,6), butanetriol-(1,2,4), trimethylol-ethane pentareythritol, quinitol, mannitol and sorbitol, methylglycoside, diethylene glycol, triethylene glycol, tetraethylene glycol polyethylene glycols, dipropylene glycol, polypropylene glycols, dibutylene glycol and polybutylene glycols. The polyesters may also contain a proportion of carboxyl end groups. Polyesters of lactones such as ε-caprolactone or hydroxycarboxylic acids such as ω-hydroxycaproic acid may also be used.

The polyesters used according to the invention which have at least 2, generally 2 to 8 and preferably 2 to 3 hydroxyl groups are also known per se and are prepared, for example, by the polymerization of epoxides such as ethylene oxide, propylene oxide, butylene oxide, tetrahydrofuran, styrene oxide or epichlorohydrin, either each on its own, e.g. in the presence of boron trifluoride or by addition of these epoxides, either as mixtures or successively, to starting components having reactive hydrogen atoms, such as water, alcohols, ammonia or amines, e.g. ethylene glycol, propylene glycol-(1,3) or -(1,2), trimethylolpropane, 4,4'-dihydroxydiphenylpropane, aniline, ethanolamine or ethylene diamine. Sucrose polyethers may also be used according to the invention, e.g. those described in German Auslegeschriften Nos. 1,064,938 and 1,176,358. It is in many cases preferred to use polyethers which contain predominantly primary hydroxyl groups (up to 90% by weight based on all the hydroxyl groups present in the polyether). Polyethers modified with vinyl polymers, e.g. the compounds obtained by the polymerization of styrene or acrylonitrile in the presence of polyethers as described in U.S. Pat. Nos. 3,383,351, 3,304,273, 3,523,093 and 3,110,695 and German Patent Specification No. 1,152,536, are also suitable, as well as polybutadienes which have hydroxyl groups.

Particularly to be mentioned among the polythioethers are the condensation products obtained by reacting thiodiglycol on its own and/or with other glycols, dicarboxylic acids, formaldehyde, aminocarboxylic acids or amino alcohols. The products obtained are polythio mixed ethers, polythio ether esters or polythio ether ester amides, depending on the cocomponents.

Suitable polyacetals include, for example, the compounds which can be prepared from glycols such as diethylene glycol, triethylene glycol, 4,4'-dioxethoxydiphenyl dimethylmethane, hexanediol and formaldehyde. Suitable polyacetals for the purpose of the invention may also be prepared by the polymerization of cyclic acetals.

The polycarbonates with hydroxyl groups used may be of the kind known per se, for example those which can be prepared by the reaction of diols such as propanediol-(1,3), butanediol-(1,4) and/or hexanediol-(1,6), diethylene glycol, triethylene glycol or tetraethylene glycol with diarylcarbonates, e.g. with diphenylcarbonate or phosgene.

Suitable polyester amides and polyamides include, for example, the predominantly linear condensates prepared from polyvalent saturated and unsaturated carboxylic acids or their anhydrides and polyvalent saturated and unsaturated amino alcohols, diamines, polyamines and mixtures thereof.

Polyhydroxyl compounds already containing urethane or urea groups and modified or unmodified natural polyols such as castor oil, carbohydrates or starch may also be used. Addition products of alkylene oxides and phenol formaldehyde resins or of alkylene oxides and urea formaldehyde resins are also suitable for the purpose of the invention.

Representatives of these compounds which may be used according to the invention have been described, for example, in High Polymers, Vol. XVI, "Polyurethanes, Chemistry and Technology" by Saunders-Frisch, Interscience Publishers, New York, London, Volume I, 1962, pages 32–42 and pages 44–54 and Volume II, 1964, pages 5–6 and 198–199 and in Kunststoff-Handbuch, Volume VII, Vieweg-Höchtlen, Carl-Hanser-Verlag, Munich, 1966, e.g. on pages 45–71.

Mixtures of the above mentioned compounds which contain at least two hydrogen atoms capable of reacting with isocyanates and have a molecular weight of from 400 to 10,000 may, of course, also be used, for example mixtures of polyethers and polyesters.

The starting components used according to the invention may also include compounds with a molecular weight of from 32 to 400 which have at least two hydrogen atoms capable of reacting with isocyanates. These compounds are also understood to be compounds containing hydroxyl groups and/or amino groups and/or thiol groups and/or carboxyl groups, preferably hydroxyl groups and/or amino groups, and they serve as chain lengthening agents or cross-linking agents. They generally have from 2 to 8 hydrogen atoms capable of reacting with isocyanates, preferably 2 or 3 such hydrogen atoms.

The following are examples of such compounds: Ethylene glycol, propylene glycol-(1,2) and -(1,3), butylene glycol-(1,4) and -(2,3), pentanediol-(1,5), hexanediol-(1,6), octanediol-(1,8), neopentyl glycol, 1,4-bis-hydroxymethylcyclohexane, 2-methyl-1,3-propanediol, glycerol, trimethylol propane, hexanetriol-(1,2,6), trimethylolethane, pentareythritol, quinitol, mannitol and sorbitol, diethylene glycol, triethylene glycol, tetraethylene glycol, polyethylene glycols with a molecular weight of up to 400, dipropylene glycol, polypropylene glycols with a molecular weight of up to 400, dibutylene glycol, polybutylene glycols with a molecular weight of up to 400, 4,4'-dihydroxy-diphenyl propane, dihydroxymethyl-hydroquinone, ethanolamine, diethanolamine, triethanolamine, 3-aminopropanol, ethylene diamine, 1,3-diaminopropane, 1-mercapto-3-aminopropane, 4-hydroxyphthalic acid, 4-aminophthalic acid, succinic acid, adipic acid, hydrazine, N,N-dimethylhydrazine, 4,4'-diaminodiphenylmethane, tolylenediamine, methylene-bis-chloroaniline, methylene-bis-anthranilic acid esters, diaminobenzoin acid esters and the isomeric chlorophenylene-diamines.

In this case again mixtures of various compounds having a molecular weight of from 32 to 400 and containing at least two hydrogen atoms capable of reacting with isocyanates may be used.

According to the invention, polyhydroxyl compounds which contain high molecular weight polyadducts or polycondensates in a finely dispersed or dissolved form may also be used. Such modified polyhydroxyl compounds are obtained when polyaddition reactions (e.g. reactions between polyisocyanates and aminofunctional compounds) or polycondensation reactions (e.g. between formaldehyde and phenols and/or amines) are carried out in situ in the above mentioned hydroxyl compounds. Processes of this kind have been described, for example, in German Auslegeschriften Nos. 1,168,075 and 1,260,142 and German Offenlegungsschriften Nos. 2,324,134; 2,423,984; 2,512,385; 2,513,815; 2,550,796; 2,550,797; 2,550,833 and 2,550,852. Polyhydroxyl compounds of this kind can also be obtained according to U.S. Pat. No. 3,869,413 or German Offenlegungsschrift No. 2,550,860 by mixing a previously prepared aqueous polymer dispersion with a polyhydroxyl compound and then removing the water from the mixture.

When such modified polyhydroxyl compounds are used as starting components for the polyisocyanate polyaddition process, polyurethane resins having substantially improved mechanical properties are in many cases obtained.

According to the invention, water and/or readily volatile organic substances may be used as blowing agents. Suitable organic blowing agents include, for example, acetone, ethyl acetate and halogen substituted alkanes such as methylene chloride, chloroform, ethylidene chloride, vinylidene chloride, monofluorotrichloromethane, chlorodifluoromethane, and dichlorodifluoromethane as well as butane, hexane, heptane and diethyl ether. The effect of a blowing agent can also be obtained by the addition of compounds which decompose at temperatures above room temperature to release gases such as nitrogen, e.g. azo compounds such as azoisobutyric acid nitrile. Further examples of blowing agents and the use of blowing agents have been described in Kunststoff-Handbuch, Volume VII, published by Vieweg and Höchtlen, Carl-Hanser-Verlag, Munich, 1966, e.g. on pages 108 and 109, 453 to 455 and 507 to 510.

Catalysts are also frequently used according to the invention. The catalyst added may be known per se, for example tertiary amines such as triethylamine, tributylamine, N-methylmorpholine, N-ethylmorpholine, N-cocomorpholine, N,N,N',N'-tetramethyl-ethylenediamine, 1,4-diazabicyclo(2,2,2)-octane, N-methyl-N'-dimethylaminoethyl-piperazine, N,N-dimethylbenzylamine, bis-(N,N-diethylaminoethyl)-adipate, N,N-diethylbenzylamine, pentamethyldiethylenetriamine, N,N-dimethylcyclohexylamine, N,N,N',N'-tetramethyl-1,3-butanediamine, N,N-dimethyl-β-phenylethylamine, 1,2-dimethylimidazole and 2-methylimidazole. Mannich bases known per se obtained from secondary amines such as dimethylamine and aldehydes, preferably formaldehyde, or ketones such as acetone, methyl ethyl ketone or cyclohexanone and phenols such as phenol, nonylphenol or bisphenol may also be used as catalysts.

Examples of catalysts which consist of tertiary amines having hydrogen atoms which are reactive with isocyanate groups include triethanolamine, triisopropanolamine, N-methyl-diethanolamine, N-ethyl-diethanolamine, N,N-dimethyl-ethanolamine and their reaction products with alkylene oxides such as propylene oxide and/or ethylene oxide.

Silaamines having carbon-silicon bonds as described e.g. in German Pat. No. 1,229,290 (corresponding to U.S. Pat. No. 3,620,984) may also be used as catalysts, e.g. 2,2,4-trimethyl-2-silamorpholine or 1,3-diethylaminomethyl-tetramethyldisiloxane.

Basic nitrogen compounds such as tetraalkylammonium hydroxides, alkali metal hydroxides such as sodium hydroxide, alkali metal phenolates such as sodium phenolate and alkali metal alcoholates such as sodium methylate may also be used as catalysts. Hexahydrotriazines are also suitable catalysts.

Organic metal compounds may also be used as catalysts according to the invention, in particular organic tin compounds.

The organic tin compounds preferably used are the tin (II) salts of carboxylic acids such as tin (II) acetate, tin (II) octoate, tin (II) ethyl hexate and tin (II) laurate and tin (IV) compounds such as dibutyl tin oxide, dibutyl tin dichloride, dibutyl tin diacetate, dibutyl tin dilaurate, dibutyl tin maleate or dioctyl tin diacetate. All of the above mentioned catalysts may, of course, be used as mixtures.

Further examples of catalysts which may be used according to the invention and details concerning the activity of the catalysts are given in Kunststoff-Handbuch, Volume VII, published by Vieweg and Höchtlen, Carl-Hanser-Verlag, Munich, 1966, e.g. on pages 96 to 102.

The catalysts are generally used in a quantity of between about 0.001 and 10% by weight, based on the quantity of formose.

Surface active additives such as emulsifiers and foam stabilizers may also be used according to the invention. Suitable emulsifiers include e.g. the sodium salts of ricinoleic sulphonate or salts of fatty acids with amines such as oleic acid diethylamine or stearic acid diethanolamine. Alkali metal or ammonium salts of sulphonic acids such as dodecylbenzenesulphonic acid or dinaphthylmethane disulphonic acid or of fatty acids such as ricinoleic acid or of polymeric fatty acids may also be used as surface active additives.

Particularly suitable foam stabilizers are the polyether siloxanes, especially those which are water-soluble. These compounds generally have a polydimethyl siloxane group attached to a copolymer of ethylene oxide and propylene oxide. Foam stabilizers of this kind have been described, for example, in U.S. Pat. Nos. 2,834,748, 2,917,480 and 3,629,308.

Other additives which may also be used according to the invention include reaction retarders, e.g. substances which are acid in reaction such as hydrochloric acid or organic acid halides; cell regulators known per se such as paraffins or fatty alcohols or dimethyl polysiloxanes; pigments; dyes; flame retarding agents known per se, such as tris-chloroethylphosphate, tricresyl phosphate or ammonium phosphate and polyphosphate; stabilizers against aging and weathering; plasticizers; fungistatic and bacteriostatic substances; and fillers such as barium sulphate, kieselguhr, carbon black or whiting.

Other examples of surface active additives, foam stabilizers, cell regulators, reaction retarders, stabilizers, flame retarding substances, plasticizers, dyes, fillers and fungistatic and bacteriostatic substances which may be used according to the invention and details concerning the use and mode of action of these additives may be found in Kunststoff-Handbuch, Volume VII, published by Vieweg and Höchtlen, Carl-Hanser-Verlag, Munich, 1966, e.g. on pages 103 to 113.

According to the invention, the components are reacted together by the known one-shot prepolymer or semiprepolymer process, often using mechanical devices such as those described in U.S. Pat. No. 2,764,565. Details concerning processing apparatus which may also be used according to the invention may be found in Kunststoff-Handbuch, Volume VII, published by Vieweg and Höchtlen, Carl-Hanser-Verlag, Munich, 1966, e.g. on pages 121 to 205.

According to the invention, the foaming reaction for producing foam products is often carried out inside molds. In this process, the foamable reaction mixture is introduced into a mold which may be made of a metal such as aluminum or a plastics material such as an epoxide resin, and it foams up inside the mold to produce the shaped product. This process of foaming in molds may be carried out to produce a product having a cellular structure on its surface or it may be carried out to produce a product having a compact skin and cellular core. According to the invention, the desired result can be obtained by either introducing just sufficient foamable reaction mixture to fill the mold with foam after the reaction or introducing a larger quantity of reaction mixture than is necessary to fill the mold with foam. The second method is known as "overcharging" and is a procedure which has been disclosed, e.g. in U.S. Pat. Nos. 3,178,490 and 3,182,104.

So-called external mold release agents known per se, such as silicone oils, are frequently used when foaming is carried out inside molds. However, so-called internal mold release agents may also be used, if desired in combination with external mold release agents, e.g. as disclosed in German Offenlegungsschriften Nos. 2,121,670 and 2,307,589.

Cold setting foams may also be produced according to the invention using methods disclosed in British Pat. No. 1,162,517 and German Offenlegungsschrift No. 2,153,086.

Foams may, of course, also be produced by the process of block foaming or by the laminator process known per se.

When the polyhydroxyl compounds obtainable according to the invention are reacted alone (without the addition of other isocyanate reactive components) with polyisocyanates which have a powerful elasticizing effect, such as polyisocyanates with a biuret structure as described in German Auslegeschrift No. 1,543,178, hard, light-fast, scratch resistant and solvent resistant surface coatings and lacquers are obtained.

Polyether alcohols with a high functionality can be obtained by propoxylation and/or ethoxylation of the polyols. Those polyether alcohols which have high hydroxyl numbers are suitable for the production of rigid or semi-rigid cellular polyurethane resins and those with low hydroxyl numbers are suitable for use as starting materials for highly elastic polyurethane foams.

Highly cross-linked polyesters which can be added to alkyd resins to improve their hardness can be obtained by reacting the mixtures of polyhydric alcohols prepared according to the invention with polybasic carboxylic acids of the kind mentioned above, e.g. phthalic acid, isophthalic acid, terephthalic acid, tetrahydro and hexahydro phthalic acid, adipic acid or maleic acid by the usual methods of polyester condensation as described, for example, in Houben-Weyl, Methoden der organischen Chemie, Vol. XIV 12, page 40. The hydroxyl polyesters synthesized from the hydroxyl compounds which have been prepared according to the invention are, of course, also suitable starting components for the production of polyurethane resins.

The polyhydric alcohols prepared according to the invention as well as the hydroxyaldehydes and hydroxyketones can also very easily be reacted with long chain aliphatic monocarboxylic acids such as caprylic, capric, lauric, myristic, palmitic, stearic, oleic, linoleic, arachidonic or behenic acid or their derivatives such as their methyl or ethyl esters or their anhydrides or mixed anhydrides to form esters which have hydroxyl groups. These hydroxyl esters resemble the ethoxylation products of the polyols as well as the carbamic acid esters obtained by reacting the polyhydroxyl compounds obtained according to the invention with long chain monoisocyanates such as n-octyl, n-decyl, n-dodecyl, myristyl, cetyl or stearyl isocyanate (see e.g. K. Lindner, Tenside Vol. III, Wissenschaftliche Verlagsgesellschaft Stuttgart, 1964, page 2336) in being non-ionogenic surface active compounds which are valuable emulsifiers, wetting agents and plasticizers. The compounds according to the invention may also be used as moisturizers in cosmetics and plastics, and as antifreezes.

These compounds according to the invention may also be used as carbohydrate-containing substrates in the nutrient media for microorganisms. Those products of the process which consist mainly of hydroxyaldehydes and hydroxyketones containing five or six carbon atoms have proved to be particularly suitable for this purpose.

Another particularly interesting aspect of the invention is that dehydrated crude formoses of the process according to the invention may be only partially ethoxylated or propoxylated by acid catalyzed reactions, e.g. preferably with the usual Lewis acids such as boron trifluoride etherate, the boron trifluoride acetic acid complex, antimony trichloride and aluminum chloride. In such a reaction, a significant amount of acetalization or ketalization on the carbonyl functions of the formose-sugar mixtures occurs at the same time in a single operation by ring opening addition of the oxirane in accordance with the following reaction scheme:

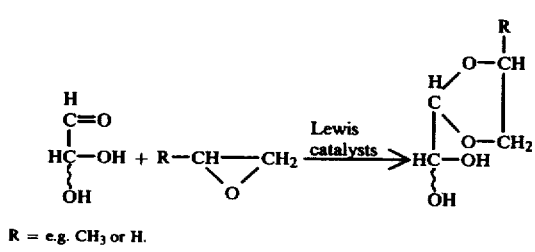

R = e.g. CH₃ or H.

Keto groups in the crude formoses are ketalized in accordance with the same reaction scheme but the reaction may also be directed so that the oxiranes undergo a considerable amount of polyaddition on the hydroxyl groups of the formoses to form polyether polyols.

Commercially interesting intermediate products are also obtained by reacting the formoses obtained according to the invention with acid anhydrides or mixed acid anhydrides, acrylonitrile, glycol carbonate, epichlorohydrin or dimethylsulphate. A particularly interesting reaction is the cyanoethylation of the formoses with 1 to 50% by weight, based on the formoses, of acrylonitrile. This reaction is preferably carried out in the presence of basic catalysts at pH values of from 7.5 to 9 and at temperatures of from 40° to 100° C., preferably 60° to 90° C. Hydrogenation of the cyanoethylation products gives rise to amino sugars which are of great interest for the production of polyurethane ureas and as hardeners for polyepoxides.

The hydroxyaldehydes and hydroxyketones obtained in the process according to the invention can easily be used for the production of polyhydric alcohols by known methods, if desired. For example, the aqueous solutions in which they are obtained can be reduced at room temperature with sodium borohydride or they can be reduced by electrolytic methods. Catalytic hydrogenation with hydrogen is another possible method. Any processes known in the art for the reduction of sugars to sugar alcohols may be employed for this purpose. Hydrogenation with Raney nickel in quantities of from 5 to 20% by weight, based on the quantity of hydroxyaldehyde and hydroxyketone mixture which is to be reduced, at hydrogen pressures of from 50 to 200 kg/cm² and temperatures of 20° to 200° C. is a particularly suitable method. However, catalysts which contain nickel, cobalt, copper, platinum, rhodium or palladium on inert carriers may be used with equally good results.

The formoses prepared according to the invention are also interesting solubilizing agents and solvents for sparingly soluble metal hydroxides such as the hydroxides of calcium, barium, rare earths, strontium, beryllium, zinc, magnesium, lead, thallium, divalent chromium, divalent manganese, divalent and trivalent iron, aluminum, divalent tin and divalent and trivalent cobalt. Such formose solutions which are enriched with various metal hydroxides are valuable catalysts for the reaction of isocyanates with water or polyhydroxyl compounds. At the same time, such solutions may, of course, be used as catalysts and cocatalysts for the autocondensation of formaldehyde and may therefore serve as, for example, absorbents in the process according to the invention.

The following Examples serve to explain the process according to the invention. Quantities given represent parts by weight or percentages by weight unless otherwise indicated.

EXAMPLE 1

A 10% aqueous formose solution having a viscosity of 1.9 mPas at 20° C., in which the reducing component amounted to 72% by weight (calculated as glucose) was used as absorption liquid. Based on the anhydrous product mixture, the molecular distribution in the absorption liquid of the compounds having 2 to 7 carbon atoms was as follows (determined by gas chromatographic analysis of the hydrogenated and subsequently silylated formoses):

Compounds with 2 C atoms: 2.87%
Compounds with 3 C atoms: 7.47%
Compounds with 4 C atoms: 14.45%
Compounds with 5 C atoms: 37.61%
Compounds with 6 C atoms: 30.92%
Compounds with 7 or more C atoms: 6.68%.

The formoses were prepared according to Example 1 of German Offenlegungsschrift No. 2,639,084 except that formose formation was stopped only after 1.4 hours. Before the resulting solution was dehydrated it was completely freed from lead and sodium or potassium ions on an acid ion exchanger and then from anions on a basic ion exchanger. The absorption liquid will be referred to hereinafter as absorbent I.

Figure 2:
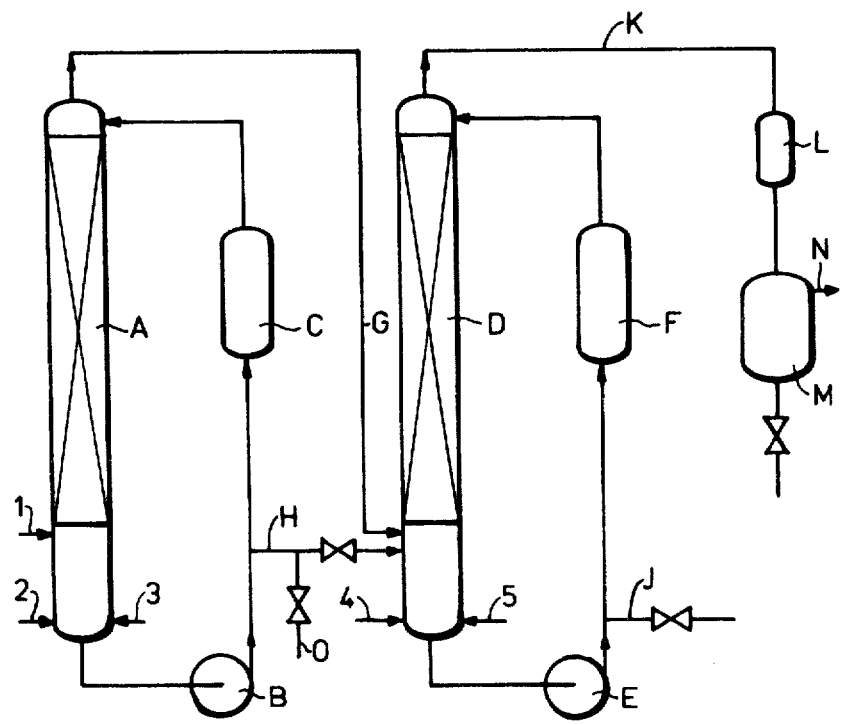

The apparatus used for the process described in this example is illustrated schematically in FIG. 2. The absorption columns have a diameter of 100 mm and a height of 2.35 m and are filled with clay saddles.

About 25 kg of the cocatalytically active absorption liquid is introduced into the sump of the absorption column (A) (capacity approximately 30 liters). This solution is kept in circulation by a pump (B) (throughout approximately 700 liters per hour) and heated to 80°–85° C. by means of an external heat exchanger (C) which can be used both for heating and for cooling. A further 25 kg of absorption liquid I are introduced into the sump of absorption column (D) and pumped through a heatable and coolable heat exchange (F) by the pump (E) (pump output approximately 500 liters per hour) to be preheated to temperatures of from 80° to 85° C. When these temperatures have been reached in both absorption columns, process gas containing formaldehyde (temperature above 85° C.) is introduced into absorption column (A) at 1 at the rate of 21.33 Nm³/h and from there it is conducted into absorption column (D) through the gas pipe (G).

The aqueous lead-II-acetate solution (concentration approximately 10%) is then introduced into the sump of absorption column (A) at 2 at a rate of approximately 180 ml/h and into the sump of absorption column (D) at 4 at a rate of approximately 80 ml/h. At the same time, a 10% aqueous sodium hydroxide solution is introduced into the sump of absorption columns (A) and (B) at 3 and 5 at such a rate that the pH in the columns is maintained at 6.5. It has been found in practice that this requires a supply of 375 to 420 ml/h of 10% NaOH solution for column (A) and from 71 to 80 ml/h of this solution for column (D). The formaldehyde synthesis gas, which has the following composition:

|  | Nm³/h | Vol. % |
|---|---|---|
| $N_2$ | 6.73 | 31.607 |
| $H_2$ | 1.35 | 6.441 |
| $CO_2$ | 0.31 | 1.477 |
| CO | 0.02 | 0.099 |
| $HC-OCH_3$ (O‖) | 0.01 | 0.066 |
| $CH_4$ | 0.01 | 0.066 |
| $CH_2O$ | 3.83 | 17.565 |
| $H_2O$ | 8.93 | 42.012 |
| $CH_3OH$ | 0.14 | 0.667 |
|  | 21.33 Nm³/h | 100.000 Vol. % | is introduced into the absorption columns in countercurrent to the absorption liquid.

To maintain a steady state when equilibrium has been established, the heat exchanger (C) must be cooled and the heat exchanger (F) moderately heated (to compensate for the loss of heat by radiation).

The absorption liquid from absorption column (A), which in the steady state contains approximately 40 to 50% of formoses and approximately 3 to 8% of residual formaldehyde, is continuously discharged into absorption column (D) through pipe (H) to keep the sump level constant. In column (D), the formaldehyde dissolved in the absorption solution and still present in the process gas is converted into formose. An approximately 50 to 60% aqueous formose solution having a residual formaldehyde content of not more than about 0.5% is discharged from the sump of absorption column (D) through pipe (I) (at a rate of approximately 8 to 10 kg/h).

The exhaust gases leaving the top of column (D) are transferred to the heat exchanger (L) and separator (M) through pipe (K). Water having a formaldehyde content of at the most 0.1% collects in the separator (M) at a rate of approximately 2.0 to 4.0 kg/h. The exhaust gas leaving the separator (M) through pipe (N) has approximately the following composition:

|  | Vol. - % |
|---|---|
| $N_2$ | 77–80 |
| $H_2$ | 15.5–16.5 |
| $CO_2$ | 3.6–3.8 |
| CO | 0.24 |
| traces of methane, methyl formate and water. | |

The continuously operating plant for the production of formose can be stopped at any time. When the apparatus is started up again, the 50 to 60% formose solution which is formed in the absorption towers can immediately be used as cocatalytically active absorption solution without being first diluted.

The formose solution leaving at (I) can be continuously freed from metal ions and anions such as formate and lactate ions by being passed over a commercial acid ion exchanger and if necessary also subsequently over a commercial basic ion exchanger, and can thereby be completely desalted. The formose solution thus obtained has an outstanding color quality and can easily be hydrogenated. It can be dehydrated in a vacuum, preferably in a falling film and/or thin layer evaporator at 50° to 60° C. The honey-like formose solution obtained with a water content of 8% has a viscosity of 86,700 mPas at 20° C. This formose, optionally as mixture with 10 to 30% by weight of elasticizing polyesters or polyethers with OH numbers of 20 to 90, is suitable for use as starting product for the production of open celled, rigid polyurethane foams with high flame resistance. It is surprisingly found that foaming of this starting product can be carried out at isocyanate indices (NCO × 100/OH) of as low as about 30 to 48.

When the procedure according to Example 1 is employed, a steady state of equilibrium in the reactor system, which is recognized by the constancy of composition of the formose leaving the apparatus at I, is reached after about 5 hours. At steady state, the proportion of formose which has a reducing action amounts to 71%, calculated as glucose. Gas chromatographic analysis of the hydrogenated and silylated reaction product shows the following molecular distribution:
Compounds with 2 C atoms: 1.78%
Compounds with 3 C atoms: 2.19%
Compounds with 4 C atoms: 4.33%
Compounds with 5 C atoms: 13.98%
Compounds with 6 C atoms: 45.96%
Compounds with 7 or more C atoms: 31.76%.

It is surprising that in this Example, formaldehyde condensation is not completely suppressed by the formation of sparingly soluble lead carbonate in spite of the relatively high proportion of carbon dioxide in the synthesis gases (608.9 g of carbon dioxide per hour, compared with 5130 g of formaldehyde per hour) and in spite of the fact that lead acetate is only introduced at a rate of about 27.7 g per hour. These quantities correspond to an approximately 162 times molar excess of carbon dioxide, based on the quantity required for lead carbonate formation.

EXAMPLE 2

Example 1 was repeated with absorption solutions II and III described below. At steady state, the products obtained are identical to those of Example 1, but the time required for reaching this steady state is considerably shortened with increasing concentration of formose in the absorption liquid.

Preparation of Absorption Liquid II

3000 Parts of a 37% aqueous formaldehyde solution (37 mol of formaldehyde) are heated to 70°–90° C. 30 Parts (0.08 mol) of lead(II) acetate are added at this temperature. The mixture is then further heated to 100° C. and adjusted to pH 6.7 at this temperature by dropwise addition of a 15% Ca(OH)$_2$ suspension.

After 6 hours, the formaldehyde content has dropped to 20% and the supply of Ca(OH)$_2$ is stopped. The pH of the reaction mixture then slowly falls. When pH 5.7 is reached, the mixture is maintained at this pH by further addition of Ca(OH)$_2$ suspension. After a further 7.5 hours, the residual formaldehyde content has dropped to 0.5% and the reaction mixture is cooled. An approximately 37% solution of a cocatalyst mixture consisting of hydroxyaldehydes and hydroxyketones is obtained. In this mixture, the molar ratio of compounds having 3 C atoms to compounds having 4 C atoms is 0.75, the molar ratio of compounds having 4 C atoms to compounds having 5 C atoms is 0.23 and the molar ratio of compounds having 5 C atoms to compounds having 6 C atoms is 0.67. The solution is suitable for use as cocatalyst without further treatment.

Preparation of Absorption Liquid III 30,000 Parts of a 37% aqueous formaldehyde solution (370 mol of formaldehyde) are heated to 70°–90° C. 150 Parts (0.4 mol) of lead (II) acetate and 810 parts of absorption liquid II are added at this temperature. The mixture is then heated to 90°–95° C. When this temperature is reached, the heat supply is removed. During the next 5 minutes, the pH of the solution is adjusted to 6.5 by the addition of approximately 2000 parts of a 10% sodium hydroxide solution. During the exothermic reaction which sets in immediately, the reaction temperature rises to 98°–99° C. and the reaction mixture begins to boil.

The pH is maintained at 6.5 by constant dropwise addition of NaOH solution until 30% conversion has been attained (formaldehyde content of the reaction mixture: 23.6%). The supply of NaOH is then stopped so that the pH of the mixture slowly drops. When the pH reaches 5.7, the slowly boiling reaction mixture is maintained at this pH by dropwise addition of a further 700 parts of 10% sodium hydroxide solution. After 30 minutes, the formaldehyde content has dropped to 16%, after a further 25 minutes to 13% and after a further 30 minutes to 8%. After another 10 minutes, the reaction mixture only contains 1.3% of formaldehyde.

The reaction is then stopped by cooling. When the temperature of the reaction mixture has dropped to 90° C., 50 parts of active charcoal are added. 100 Parts of potassium carbonate are added at 65° C. to precipitate the lead ions. After removal of the precipitated lead carbonate and the active charcoal by filtration, a clear, colorless solution is obtained, which is then concentrated by evaporation to 60% (absorption liquid III). Further concentration by evaporation in a water jet vacuum at 40° C. yields 11,713 parts of a colorless, viscous mixture of polyhydric alcohols, hydroxyaldehydes and hydroxyketones. A mixture of polyhydric alcohols is obtained from this by electrochemical reduction or catalytic hydrogenation. Gas chromatic analysis of the silylated polyhydric alcohols shows the following distribution of components:

dihydric alcohols: 0.2% by weight
trihydric alcohols: 2.6% by weight
tetrahydric alcohols: 4.6% by weight
pentahydric alcohols: 24.8% by weight
hexahydric alcohols: 44.5% by weight
heptahydric alcohols and:
higher valent alcohols: 23.5% by weight.

EXAMPLE 3

25 kg of the absorption liquid described in Example 1, which contains approximately 10% of formose, are introduced into the sump of absorption column A of FIG. 2 (capacity approximately 30 l). This solution is pumped over the external heat exchanger C (heatable and coolable) in column A by pump B (700 l/h) and heated until it reaches a temperature of about 85° to 90° C.

25 Liters of water are introduced into the sump of column D and pumped over the cooled heat exchanger F (20° to 40° C.) in column D by the pump E (500 l/h). When the aforesaid reaction temperature of 85° to 90° C. has been reached in column A, the formaldehyde process gas is introduced into absorption column A at temperatures above 85° C. at a rate of 21.33 Nm$^3$/h. A 10% lead acetate hydrate solution is then delivered into the sump of the absorption tower A at a rate of 260 ml/h. At the same time, 10% sodium hydroxide solution begins to be fed into the sump of column A to maintain the pH at 6.5. In practice, it is found that this requires from 440 to 500 ml/h of 10% sodium hydroxide solution. The formaldehyde process gas, which corresponds in its composition to the gas used in Example 1, is passed through absorption column A in countercurrent to the absorption liquid. The heat exchangers C and F are cooled as required for the operating conditions. At a steady state of equilibrium, the absorption liquid in column A has been concentrated to 60–70% by fresh formation of formose and, if the temperatures indicated above are employed (85° to 90° C.) it only contains 0.5 to 0.6% of residual formaldehyde in the sump of column A.

The formose formed in the process (7.0 to 8.3 kg/h) is continuously discharged through pipes H and O while the sump level in column A is kept constant.

When the process is carried out as described above, the process gas leaving column A has an increased water content and only contains a small residue of formaldehyde. The water is deposited in column D and used for removal of the remaining formaldehyde.

At a steady state of equilibrium, from 3.8 to 4.6 kg of water condensate containing 0.1 to 0.2% of formaldehyde are drawn off through pipe J while the sump level is kept constant. The gas is discharged from the apparatus through pipe N after flowing through pipe K, heat exchanger L and receiver M. A further 0.2 to 0.4 kg of water per hour (0.1 to 0.2% formaldehyde content) separate in the receiver M.

Due to the low viscosity of the 60 to 70% formose solution obtained in this process, the solution can be worked up, i.e. completely desalted over ion exchangers, as described in Example 1. It is an advantage of this procedure that higher formose concentrations can be obtained without additional supply of energy. The manufacturing costs are reduced.

If the continuous process is stopped, the 60 to 70% formose solution left in the apparatus may, of course, be used at any time in its undiluted form as cocatalytically active absorption liquid to start up the manufacture of formose again.

According to another variation of the process, the production of formaldehyde-containing formose in the first absorption column A and the formation of formaldehyde solutions at concentrations of up to 40% in absorption column D or optionally in further absorption columns or separators take place simultaneously.

EXAMPLE 4

Example 1 is repeated except that in this case neither catalyst nor sodium hydroxide solution is fed into absorption column A and the absorption liquid which is kept in circulation by pumping is kept at a temperature of about 50° C. by cooling the heat exchanger C. After 15 hours, the absorption liquid contains 48.3% of formaldehyde. The formaldehyde-containing absorption liquid is then continuously fed into an external cascade of stirrer vessels through pipe H with the addition of catalyst and sodium hydroxide solution, and is kept there for 15 minutes at a temperature of from 95° to 100° C. to be converted into formose.

The example is repeated with the same absorption liquid but with higher solid contents. At a formose content of 30%, the absorption liquid has a viscosity of 2.8 mPas/20° C., at 50% it has a viscosity of 6.8 mPas/20° C., at 60% a viscosity of 14 mPas/20° C. and at 70% it has a viscosity of only 42 mPas/20° C. In the latter case, the formaldehyde content of the absorption liquid can be increased to 64% without paraformaldehyde precipitating. Even these highly concentrated solutions can be converted extremely rapidly into formose in the external cascade of stirrer vessels, as described above.

EXAMPLE 5

This example describes the discontinuous variation of the process according to the invention. 213 Liters per hour of the synthesis gas described in Example 1 (containing about 51 g of formaldehyde per hour) are introduced into 250 g of an absorption liquid which contains 15% of a formose having the following molecular distribution:

$C_2$ fraction: 16.8% by weight
$C_3$ fraction: 2.10% by weight
$C_4$ fraction: 29.9% by weight
$C_5$ fraction: 25.1% by weight
$C_6$ fraction: 7.2% by weight.

The process gases are conducted into the absorption liquid through an inlet pipe which dips into a cylindrical reaction vessel to a point 0.5 cm above the bottom of the vessel. The reaction vessel has a cross-section of 4 cm and a height of 40 cm. Although the stirred absorption liquid is not pumped counter-current to the process gas and no packing is present, in other words the conditions provided by the apparatus are less advantageous than those described in Example 1, about 98% of the formaldehyde in the process gas is absorbed and converted into formoses.

The formation of formose is varied as follows with regard to the catalysts used and the pH control:

(a) 0.375 g of lead-II-acetate is dissolved at 25° C. in a mixture of 250 g of the 15% formose solution and 10 g of a 37% aqueous formaldehyde solution. This absorption liquid is then heated to 98° C. Synthesis gas is then introduced for one hour, while the pH is maintained at 6.6 by the addition of 0.71 g of NaOH dissolved in 5 g of water. After the absorption of approximately 49 g of formaldehyde in the course of one hour, the reaction vessel is rapidly cooled and the formation of formose is stopped when the residual formaldehyde content is 2.5 g. A formose solution which is exceptionally light in color is obtained by this method. Without further purification or removal of salt, the solution is concentrated to a water content of about 10% by weight in a thin layer evaporator at 50° C. and 18 Torr. A water clear solution having a viscosity of 14,500 mPas at 20° C. is obtained. Yield: 96 g.

The formose solution at that stage only contains about 2% by weight of formaldehyde bound in hemiacetal groups. By adding commercial emulsifiers and elasticizing hydroxyl polyethers or polyesters in proportions of 10 to 20% by weight, based on the quantity of formose, this formose-sugar mixture containing 10% by weight of water can be foamed up with crude diphenylmethane diisocyanate to yield open-celled, elasticized polyurethane foams which are highly flame resistant. The lead compounds dissolved in the crude formose act as catalysts for the isocyanate-water and isocyanate-OH reaction.

(b) The procedure is the same as described under (a) but the absorption liquid used in this case is a 15% aqueous solution of the formose described in Example 1 containing 72% of reducing agents, calculated as glucose. When, after a period of one hour, approximately 50 g of formaldehyde have been absorbed from the process gas and been converted almost completely to formose, the addition of sodium hydroxide solution is stopped and the pH is adjusted to 4.8 with acetic acid. This virtually stops the formation of formose. The process gas then continues to be fed into the absorption solution for a further 18 minutes. Approximately 15 g of formaldehyde are absorbed substantially without formose formation. The supply of process gas is then stopped. By the addition of 7.4 g of pulverulent calcium hydroxide or 3 g of diethylaminoethanol or 4 g of bis-hydroxyethylcyclohexylamine, the excess formaldehyde in the reaction mixture is bound in the course of 1.2 hours at 70° C. with α-methylolation of the resulting polyhydroxyaldehydes and polyhydroxyketones. In this variation of the process, the aldolization reactions are accompanied by crossed Cannizzaro reactions. The sugar component which has a reducing action, calculated as glucose, is thereby reduced from about 72% to 14%.

This variation of the example shows that the process according to the invention can be coupled with α-C-methylolation while crossed Cannizzaro reactions take place at the same time. The solution is concentrated by evaporation to a water content of about 10% by weight in a thin layer evaporator at 50° C. and 14 Torr without further purification or desalting. Yield: 113 g; Viscosity: 82,500 mPas/20° C.

The crude formose obtained may be used directly as activated polyol for the production of open celled, flame resistant polyurethane foams, as already described above.

(c) The procedure is initially the same as described under (a) but using a 15% aqueous formose solution according to Example 2 (absorption liquid III) as cocatalyst. In the course of one hour, approximately 50 g of formaldehyde in the absorption liquid which is maintained at a pH of 7.8 by the continuous addition of 8 g of calcium hydroxide are converted into aldolized formoses or formoses which are partially reduced by a crossed Cannizzaro reaction. Less than 0.5% of the calcium put into the process precipitates as calcium formate or calcium carbonate from the aqueous formose solution. When the filtered crude formose is concentrated by evaporation to a water content of approximately 10% by weight, the honey-like formose syrup remains completely clear, i.e. the sparingly soluble calcium formate formed in the Cannizzaro reaction is kept in solution by the formose. Yield: 99 g; viscosity: 105,000 mPas determined at 20° C.

(d) The procedure is the same as described under (c) except that the cocatalyst is used at substantially higher concentrations, as follows:

($d^1$) 50% formose solution corresponding to absorption liquid III (Example 2) Viscosity: 8.9 mPas at 20° C.

($d^2$) 60% formose solution corresponding to absorption liquid III (Example 2). Viscosity: 16.8 mPas at 20° C.

($d^3$) 70% formose solution having the molecular distribution of absorption liquid III. Viscosity: 59 mPas at 20° C.

The process gases containing formaldehyde are introduced in each case at a rate of 0.213 $Nm^3/h$ for 2 hours into 250 g of each of the absorption liquids mentioned above which act as cocatalyst. At the same time, while the pH is constantly controlled by means of an electrode, calcium hydroxide is continuously added in small quantities so that the pH is maintained at 8 to 8.2 (total 14.6 g). When this procedure is employed, $\alpha$-methylolation of the resulting formose-sugar mixtures proceeds very rapidly and crossed Cannizzaro reactions take place at the same time.

Approximately 97 g of the approximately 102 g of formaldehyde fed into the process are bound by the above mentioned reactions in the course of 2 hours. The filtered, dehydrated, yellowish-brown formose syrups form complexes with the calcium ions present. Formose syrups obtained in experiments $d^1$, $d^2$ and $d^3$ dehydrated to a water content of 10% by weight are completely clear. Due to the presence of complex basic calcium formate they are highly activated for isocyanate reactions.

(e) The same procedure is employed as described under (c) but the following are used as interesting new mixed catalysts:

($e^1$) 20 g of an ash residue of plant material (tobacco leaves) having the following analytical composition (converted to oxides): 36% CaO, 29.1% $K_2O$, 3.2% $Na_2O$, 7.4% MgO, 1.9% $Fe_2O_3$, 4.7% $P_2O_5$, 3.1% $SO_3$, 5.8% $SiO_2$, 6.7% Cl+trace elements;

($e^2$) 24 g of an ash residue from white cabbage leaves having the following composition: 28.5% CaO, 23.1% $K_2O$, 8.9% $Na_2O$, 4.1% MgO, 1.2% $Fe_2O_3$, 3.7% $P_2O_5$, 17.4% $SO_3$, 1.9% $SiO_2$, 12.6% Cl;

($e^3$) 27 g of an ash residue from protein-rich biomasses obtained from biological clarification plants, having the following composition: 21.5% calcium, 16.2% lead, 9.7% magnesium, 7.8% copper, 5.2% cadmium, 10.8% chromium, 27% iron, and in addition trace elements. The metals are in the form of carbonates, oxides, chlorides, phosphates and silicates.

In variations $e^1$ to $e^3$ of the experiment, approximately 50 g of formaldehyde from the process gases are converted into formoses in the course of one hour at pH 7.8, if indicated with the addition of small quantities of calcium hydroxide. The reaction product is filtered from the bulk of insoluble ash residues. When the crude formoses which have not been desalted are concentrated by evaporation to a water content of about 10% by weight, honey yellow formose syrups are obtained which contain about 3% by weight of various metals bound by complex formation and which have a high catalytic activity in the reaction with polyisocyanates.

EXAMPLE 6

Example 5a is repeated with various absorption liquids. One group of these absorption liquids consists of honeys of any origin which contain various enzymes and secretions from bees, i.e. natural invert sugars which contain nitrogen (Group I).

The other group of cocatalytically active absorption liquids which can be used according to the invention consists of concentrated hydrolysates of plant material or microbial biomasses which, after acid hydrolysis, have been desalted on ion exchangers containing basic groups (Group II).

Group I (a) Floral Honey from Bees

Nitrogen content of anhydrous products: 0.05%; viscosity of a 60% by weight solution in water: 11.8 mPas at 20° C.

(b) Water Clear Acacia Honey

Nitrogen content: 0.03%; viscosity of a 60% aqueous solution: 14 mPas; viscosity of a 15% solution in water-ethylene glycol (3:1): 22.5 mPas/20° C.

(c) Pale Yellow Rape Honey

Nitrogen content: 0.05%; viscosity of a 60% aqueous solution: 14 mPas at 20° C.

(d) Golden Yellow Fruit, Floral and Clover Honey

Nitrogen content 0.043%; viscosity of 60% aqueous solution: 12 mPas at 20° C.

(e) Lime Blossom Honey (Golden Yellow)

Nitrogen content 0.029%; viscosity of 60% aqueous solution: 16 mPas at 20° C.

(f) Dark Brown Buckwheat Honey

Nitrogen content: 0.041% viscosity of 60% aqueous solution: 16 mPas at 20° C.

(g) Yellow Brown Fir Tree Honey with Greenish Shimmer

Nitrogen content: 0.038%; viscosity of 60% aqueous solution 17 mPas at 20° C.

(h) Reddish Brown Heather Honey

Nitrogen content: 0.043%; viscosity of a 40% solution in ethylene glycol/$H_2O$ (1:1): 52 mPas.

Although absorption liquids (a) to (h) mentioned above differ in their nitrogenous components according to the plant source from which they are obtained (acacia, horse chestnut, fruit trees, broom, heather, hazelnut, buckwheat, rape, sunflower, thyme, bilberry, acorn, clover, gooseberry, dandelion, sage, silver fir, thistle, etc.), they are very similar to each other in their cocatalytic activity when used as cocatalysts and washing liquids for the synthesis of formose according to Example 5(a). The formose mixtures obtained are not significantly deepened in color.

Group II (a) 150 Parts by weight of moist, freshly cut grass (dry weight 32 parts by weight) are hydrolyzed under pressure in an autoclave for 6 hours at 130° C. in 300 parts by weight of water with the addition of 0.5 parts by weight of sulphuric acid. In the course of this process, various polysaccharide reserve materials, sugar-like cell constituents, celluloses and hemicelluloses as well as nucleic acids containing ribose and desoxyribose are partially hydrolyzed and converted into water-soluble mono- and oligo-saccharides. After filtration, removal of the sulphuric acid and any acids derived from the plant material, such as phosphoric acids, etc. by means of a commercial basic ion exchanger and concentration by evaporation under vacuum, a syrupy liquid is obtained. The hydrolyzed amino acids present in this liquid react with keto and aldehyde functions of the hydrolyzed polysaccharides in the course of the evaporation process to form yellowish brown products (Maillard reaction). Yield: 19 parts by weight.

(b) The procedure is the same as described under (a) but 160 parts by weight of a moist, active cell culture consisting of mycelium-like biomasses of a fully biologically operating clarification plant and containing a wide spectrum of pseudomona types and other microbial systems (dry weight 35 g) are used for hydrolysis. Yield: 12 parts by weight of a brown syrup.

(c) The procedure is exactly as described under (a) but using a moist, not dried bakers' yeast (150 parts by weight). Yield: 22 parts by weight of a brown syrup.

The syrupy mixtures prepared according to (a) to (c) are diluted to 10% with water or ethylene glycol/water and used as cocatalytically active absorption liquids as described in Example 5a. Colorless formoses similar in consistency to those obtained in Example 5a are obtained.

EXAMPLE 7

Preparation of the Absorption Liquids (a) 100 Parts by weight of absorption liquid I which has been concentrated to 10% by weight of water (see Example 1) are mixed with 100 parts by weight of ethylene glycol. Viscosity of absorption liquid at 20° C.: 267 mPas.

(b) The procedure is the same as described under (a) but the ethylene glycol is replaced by 100 parts by weight of diethylene glycol. Viscosity of absorption liquid at 20° C.: 695 mPas.

(c) The procedure is as described under (a) but the ethylene glycol is replaced by a mixture of 50 parts by weight of water and 50 parts by weight of glycerol. Viscosity of absorption liquid: 28 mPas/20° C.

(d) The procedure is the same as under (a) but the ethylene glycol is replaced by 100 parts by weight of tetraethylene glycol. The viscosity of the absorption liquid obtained is 1830 mPas/20° C.

(e) The procedure is the same as under (a) but the ethylene glycol is replaced by 100 parts by weight of methanol. Viscosity of absorption liquid obtained: 11 mPas/20° C.

(f) The procedure is as described under (a) but the ethylene glycol is replaced by 100 parts by weight of ethanol. Viscosity of absorption liquid obtained: 33 mPas/20° C.

(g) The procedure is as described under (a) but the ethylene glycol is replaced by 100 parts by weight of propylene glycol. Viscosity of absorption liquid: 873 mPas/20° C.

(h) The procedure is as described under (a) but the ethylene glycol is replaced by 100 parts by weight of dipropylene glycol. Viscosity of absorption liquid: 2900 mPas/20° C.

When 150 parts by weight of formaldehyde obtained from synthesis gases containing formaldehyde are passed through these absorption liquids for 3 hours by the method described in Example 5a, formose-sugar mixtures are obtained. After they have been dehydrated, they are more readily miscible with tetrapropylene glycol and higher molecular weight copolyethers of propylene oxide and ethylene oxide (1:1).

EXAMPLE 8

Preparation of the Absorption Liquids (a) 100 Parts by weight of absorption liquid I which has been concentrated to a water content of 10% by weight (see Example 1) are mixed with 100 parts by weight of a solution of 50 parts by weight of $$H_3C-C-C\begin{matrix}CH_2OH\\H\\O\end{matrix}$$
$$CH_2OH$$

or its cyclohemiacetal forms in 50 parts by weight of water. Viscosity of the 70% absorption liquid: 42 mPas/20° C.

(b) The procedure is the same as described under (a) but the 50 parts by weight of aldolized propionaldehyde are replaced by 50 parts by weight of the syrupy aldolized acetone represented by the following idealized constitutional formula:

$$\begin{matrix}HOCH_2\\ \\HOCH_2\end{matrix}CH-C-CH\begin{matrix}CH_2OH\\ \\ \\CH_2OH\end{matrix}$$
$$O$$

Viscosity of the absorption liquid at a concentration of 70%: 83 mPas at 20° C.

(c) The procedure is the same as described under (a) but the 50 parts by weight of aldolized propionaldehyde used there are replaced by 50 parts by weight of aldolized methyl ethyl ketone having the following idealized constitution:

$$\begin{matrix}HOH_2C& &CH_2OH\\|& &|\\CH-C-C-CH_3\\|&\|&|\\HOH_2C&O&CH_2OH\end{matrix}$$

Viscosity of 70% absorption liquid: 81 mPas at 20° C.

(d) The procedure is the same as described under (a) but the 50 parts by weight of aldolized propionaldehyde are replaced by 50 parts by weight of aldolized isobutyraldehyde or its dimeric cyclohemiacetal. Viscosity of the 70% absorption liquid: 110 mPas/20° C.

(e) The procedure is the same as described under (a) but the 50 parts by weight of aldolized propionaldehyde are replaced by 50 parts by weight of aldolized n-butyraldehyde represented by the following constitutional formula

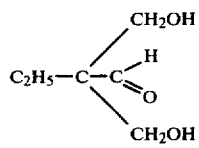

Viscosity of the 70% absorption liquid: 105 mPas/20° C.

(f) The procedure is the same as described under (a) but the 50 parts by weight of aldolized propionaldehyde used there are replaced by 50 parts by weight of a mixture of aldolized cyclohexanone which contains di-, tri- and tetramethylolcyclohexanones represented by the following constitutional formulae in addition to monomethylolcyclohexanone:

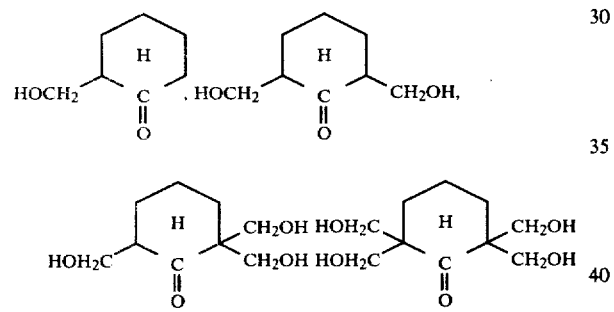

Viscosity of the 70% absorption liquid: 124 mPas/20° C.

Process According to the Invention 200 g of formaldehyde are condensed in each case in 250 g of absorption solutions (a) to (b) in the course of 4 hours by the general method of procedure described in Example 5a. Formose-sugar mixtures are obtained which can be mixed with tri- and tetrapropylene glycol to form stable solutions which show no tendency to crystallization or separation into its components at 5° C.

EXAMPLE 9

Preparation of the Absorption Liquids (a) 1000 g of absorption liquid III which has been concentrated by evaporation to 30% (see Example 2) are mixed with 1 mol of cyclopentanone.

(b) The procedure is the same as under (a) but the cyclopentanone is replaced by 1 mol of cyclohexanone.

(c) The procedure is the same as under (a) but the cyclopentanone is replaced by 1 mol of methyl ethyl ketone.

(d) The procedure is the same as under (a) but the cyclopentanone is replaced by 1 mol of propionaldehyde.

(e) The procedure is the same as under (a) but the cyclopentanone is replaced by 1 mol of isobutyraldehyde.

(f) The procedure is the same as under (a) but the cyclopentanone is replaced by 1 mol of n-butyraldehyde.

In all cases (a) to (f), 300 g of a 30% formalin solution (3 mol) is subsequently added and the aldehydes and ketones are methylolated (aldolized) in the course of 10 hours at room temperature by the addition of 10 g of calcium hydroxide.

Process According to the Invention

The water-soluble mixtures (a) to (f) obtained are used as in Example 5(a) in the form of 15% aqueous solutions as absorbents for formaldehyde-containing synthesis gases. Absorption of formaldehyde and its irreversible conversion into formose-sugar mixtures proceeds with a yield of 95 to 97%, based on gaseous formaldehyde.

EXAMPLE 10

This Example describes the use of active formaldehyde acceptors from the series of "aminoplast monomers" in absorption liquids according to the invention.

Preparation of the Absorption Liquids (a) 1000 g of absorption liquid III concentrated by evaporation to a formose content of 35% (see Example 2) are mixed with 1 mol of urea.

(b) The procedure is the same as under (a) but the urea is replaced by 0.3 mol of melamine.

(c) The procedure is the same as under (a) but the urea is replaced by 1 mol of dicyandiamide.

(d) The procedure is the same as under (a) but the urea is replaced by 1 mol of ethylene urea having the constitution represented by the following formula:

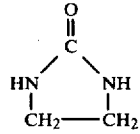

(e) The procedure is the same as under (a) but the urea is replaced by 1 mol of oxamide.

(f) The procedure is the same as under (a) but the urea is replaced by 1 mol of:

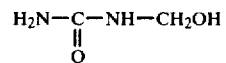

In all cases (a) to (g), 200 g of 30% formalin solution (2 mol) are subsequently added and the aminoplast monomers are methylolated in the course of 15 minutes at 60° C. in the presence of 0.8 g of potassium carbonate.

Clear absorption solutions which are stable in storage are obtained. When diluted to 15%, they have a viscosity of 1.8 to 2.5 mPas/20° C.

Process According to the Invention

When the 15% aqueous absorption liquids (a) to (f) are used in the process according to Example 5(a), approximately 96% of the gaseous formaldehyde in the synthesis gases is irreversibly absorbed with formation of formose-sugar mixtures.

EXAMPLE 11

Preparation of the Cocatalyst

500 Parts (6.17 mol of formaldehyde) of a 37% aqueous formalin solution and 5 g (0.013 mol) of lead-(II) acetate are together heated to the reflux temperature. In another vessel, 124 parts (2.0 mol) of ethylene glycol are mixed with 5 g (0.02 mol) of iodine. This mixture is introduced into the boiling formalin solution which is adjusted to pH 4 by this addition (due to the acid medium, the oxidizing agent is not yet activated at this point!). The heating bath is removed and a mixture of equal parts of potassium hydroxide and water (44% solution) is then added dropwise until the pH has been raised to 8.5. (The cocatalyst is now formed by the oxidizing agent which is activated in the basic range). The mixture then begins to boil and continues boiling without external supply of heat. Consumption of potassium hydroxide solution, calculated as solid potassium hydroxide: 4.9 parts. To maintain this exothermic reaction, a fresh supply of potassium hydroxide/water mixture is continuously added dropwise at such a rate that the reaction mixture is adjusted to pH 7.5. After 20 minutes, the formaldehyde content of the solution has dropped to 0.6%. Total consumption of potassium hydroxide solution, based on solid potassium hydroxide: 14.6 parts. To inactivate the catalyst, 1.3 parts of sulphuric acid in 10 parts of water are added. This causes lead sulphate to precipitate, and the pH drops to 4. The reaction mixture is left to cool and then suction filtered to remove insoluble constituents. After concentration by evaporation in a water jet vacuum at 70° C., 300 parts of a slightly yellowish, viscous mixture of polyhydric alcohols, hydroxyaldehydes and hydroxyketones are obtained. The mixture has a water content of 1% and containing 38.0% of reducing components, based on glucose. After catalytic hydrogenation and silylation, the gas chromatogram indicates the following distribution of components:

Dihydric alcohols: 44.6% by weight
Trihydric alcohols: 4.8% by weight
Tetrahydric alcohols: 7.3% by weight
Pentahydric alcohols: 10.3% by weight
Hexahydric alcohols: 23.8% by weight
Heptahydric and higher hydric alcohols: 9.2% by weight.

Process According to the Invention

Solutions of these formoses in water at concentrations of 3 to 70% are used as absorption liquids according to Example 5(a). They have excellent cocatalytic properties for rapid formose formation from process gases containing formaldehyde.

EXAMPLE 12

The procedure is the same as described in Example 5, variation e[1], but the ash residue used there as heterogeneous catalyst is replaced by higher molecular weight, insoluble matrices which are capable of swelling. These matrices were prepared as follows:

(a) 500 Parts by weight of a commercial ion exchanger containing sulphonic acid groups and based on polystyrene and divinylbenzene with a total capacity of 1.9 mval are charged with lead-II-ions by stirring a lead-II acetate solution and the ion exchanger together for 10 hours at room temperature. After swelling, 1 liter of the ion exchanger binds approximately 100 parts by weight of lead-II-ions. 3.4 g of the insoluble catalyst are used to convert 50 g of formaldehyde into formoses.

(b) 202 Parts by weight of a copolymer of styrene and maleic acid anhydride (molar ratio 1:1) are boiled with a lead-II acetate solution in water for 10 hours and then stirred for a further 10 hours at room temperature. The polymeric matrix binds approximately 198 parts by weight of lead-II ions. Approximately 1.7 parts by weight of polymeric matrix charged with lead-II ions are used for converting approximately 50 parts by weight of formaldehyde into formoses.

(c) 405 Parts by weight of an insoluble, cross-linked polymethylene urea having segment units represented by the following idealized constitutional formula:

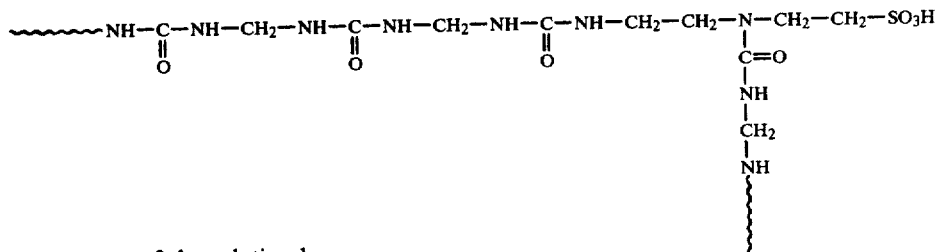

and obtained from 2 mol of urea, 1 mol of a diurea containing sulphonic acid groups having the following constitution:

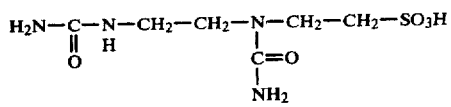

and 4.2 mol of formaldehyde by acid catalyzed condensation at 80° C. are charged with 99 parts by weight of lead-II-ions according to method (b). Approximately 3 g of the insoluble matrix charged with lead-II ions are used for converting 50 g of formaldehyde from the process gases.

(d) 500 Parts by weight of a commercial ion exchanger containing iminodiacetic acid groups and based on polystyrene crosslinked with divinylbenzene (capacity approximately 1.8 mval of the swelled resin) are charged with (d[1]) lead-II ions,
(d[2]) calcium ions by method (b).

One liter of catalysts obtained according to (d[1]) and (d[2]) contains approximately 102 parts by weight of lead-II ions or 21 parts by weight of calcium ions bound to the groups represented by the following formula:

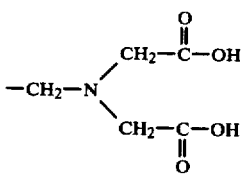

3 Parts by weight of matrix containing lead-II ions or approximately 15 parts by weight of matrix containing calcium ions are used for converting 50 parts by weight of formaldehyde from the process gases.

(e) 400 Parts by weight of a polycondensation product prepared from 1 mol of phenol, 1 mol of salicylic acid and 4 mol of formaldehyde by 10 hours' condensation at 90° C. in the presence of hydrochloric acid as catalyst (pH 1.5) are charged with ($e^1$) 150 parts by weight of lead-II ions and ($e^2$) 38 parts by weight of calcium ions. 4 Parts by weight of ($e^1$) or 10 parts by weight of ($e^2$) are used for converting 50 parts by weight of formaldehyde from the formaldehyde-containing process gases.

(f) 560 Parts by weight of a cross-linked, pulverulent polycondensation product prepared from 1 mol of phenol, 1 mol of

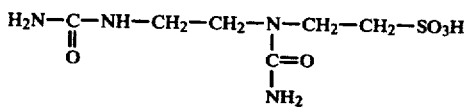

and 3.5 mol of formaldehyde at pH=1.3 and 90° C. are charged with 94 parts by weight of lead-II ions.

6 Parts by weight of this ion exchanger are used as catalyst for converting 50 parts by weight of formaldehyde from the process gases in accordance with Example 5.

(g) 420 Parts by weight of a cross-linked, pulverulent polycondensation product prepared by acid condensation from 1 mol of urea, 1 mol of the compound represented by the following formula:

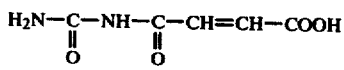

and 2.5 mol of formaldehyde by heating at 80° C. at pH 2 for 3 hours are charged with ($g^1$) 197 parts by weight of lead-II ions, ($g^2$) 21 parts by weight of magnesium ions, ($g^3$) 129 parts by weight of barium ions, ($g^4$) 38.5 parts by weight of calcium ions, ($g^5$) 109 parts by weight of tin-II ions and ($g^6$) 83 parts by weight of strontium ions.

A mixed catalyst is obtained by intimately milling 2 parts by weight of each of the insoluble catalysts $g^1$ to $g^6$. 6 Parts by weight of this mixed catalyst are used for the condensation of 51 parts by weight of formaldehyde in accordance with Example 5. A light colored formose-syrup solution is obtained.

EXAMPLE 13

The procedure is the same as in method (a) of Example 5 but 4 g of the insoluble matrix charged with lead-II ions prepared as described in Example 12, variation (b), are used as catalyst. The insoluble ion exchanger charged with lead-II ions continuously gives off catalytic quantities of lead-II ions to the solution so that the reaction is catalyzed by both homogeneous and heterogeneous catalysis. When approximately 101 g of formaldehyde from the formaldehyde containing process gas have been absorbed in the reaction mixture in the course of 2 hours at 98° C., the reaction mixture, which then has a residual formaldehyde content of 0.6%, is desalted by passing it over a cation exchanger and then over an anion exchanger. It is then concentrated by evaporation in a thin layer evaporator at 60° C. and 80 Torr. 154 g of a colorless, salt-free viscous product having a water content of 8.5% are obtained. The viscosity of the mixture containing polyhydroxyaldehydes, polyhydroxyketones and polyhydric alcohols is 81,000 mPas/20° C.

EXAMPLE 14

The procedure is analogous to that of Example 13 but in this case 14 g of the insoluble matrix containing calcium ions described in Example 12, variation ($d^2$) are used as catalyst. The pH is maintained at 9.5 during formose formation by the addition of 10% sodium hydroxide solution. The matrix, then depleted of calcium ions, is removed by filtration but in this case the formose is not desalted. When the formose solution has been concentrated to a water content of 10% by weight by thin layer evaporation at 55° C. and 18 Torr, it has a viscosity of 108,000 mPas/20° C. Yield: 162 g. 70% solutions of the completely dehydrated but not desalted crude formose in ethylene glycol, which have a viscosity of 1275 mPas at 20° C., are valuable starting materials for the production of rigid, open celled, flame resistant polyurethane polyureas.

EXAMPLE 15

4 g of a commercial ion exchanger resin based on polystyrene sulphonic acid cross-linked with divinyl benzene, which exchanger resin is charged with approximately 0.9 g of lead, are added at 70° C. to 250 g of a 15% formose solution obtained by concentrating absorption liquid I by evaporation (see Example 1). 0.21 $Nm^3$ (210 liters) of synthesis gas are introduced in the course of one hour according to Example 5(a). The reaction mixture is maintained at pH 6.9 by the addition of 10% sodium hydroxide solution and the reaction is stopped by rapid cooling when the residual formaldehyde content has dropped to 8.5% by weight. The reaction mixture is then filtered and freed from lead-II and sodium ions by passing it over a cation exchanger in the hydrogen ion form and from formic acid, lactic acid and small quantities of $C_4$-, $C_5$- and $C_6$-saccharic acids by passing it over an anion exchanger in the hydroxyl form. A completely desalted formose solution is obtained which, after dehydration, has a reducing sugar mixture component of 69%, calculated as glucose.

EXAMPLE 16

The procedure is the same as described in Example 5(a) but the concentration of cocatalyst in the absorption liquid is increased to 70% by weight (viscosity at 20° C.: 42 mPas). Desalting is not carried out and the crude formose solution obtained is dehydrated to a water content of 8.4%.

A mixture of 2 parts by weight of an emulsifier having the following constitution:

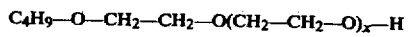

(average value of x=20), 37 parts by weight of the above crude formose having a water content of 8.4% and 30 parts by weight of an elasticizing polyether which has been prepared from trimethylol propane, propylene oxide and ethylene oxide and has an OH number of 28 is reacted with 128 parts by weight of a crude diphenylmethane diisocyanate (isocyanate content 29%) at 45° C. to form an open celled rigid polyurethane foam.

EXAMPLE 17

This example describes that discontinuous variation of the process according to the invention in which the formaldehyde is simply absorbed from the process gases in the absence of formose catalyst in the first phase of the process and the synthesis of formose is subsequently initiated whenever desired by the addition of formose catalysts.

Using the absorption apparatus described in Example 5, 213 liters per hour of a formaldehyde-containing synthesis gas which has been cooled to 100° C. are introduced at 85° C. into 250 g of a 30% aqueous formose solution which has the molecular distribution described for absorption liquid III (see Example 2). The above mentioned process gas has the composition indicated in Example 1. Approximately 71 g of formaldehyde are absorbed in absorption liquid in the course of 90 minutes. Methylene glycol and hemiacetals of the formose-sugar mixture introduced into the apparatus are thereby formed. These reaction products are in equilibrium with each other. 98% of the formaldehyde is absorbed in the course of the experiment.

The solution obtained, which is stable in storage, is subsequently reacted whenever desired to be converted into formose-sugar mixtures as follows:

(a) After a storage time of one hour at room temperature, 0.4 g of lead acetate is added to the solution which is then converted quantitatively into formose-sugar mixtures by heating for 35 minutes at 99° C. and pH 6.8 with the addition of small quantities of 10% NaOH.

(b) After a storage time of 24 hours, the solution is converted into formose-sugar mixtures by heating for one hour at 85° C. by method (a).

(c) After a storage time of one week, 1100 g of the absorption solution, which is stable in storage, is converted into formose at a temperature of only 50° C. and with the aid of pulverulent calcium hydroxide as catalyst instead of lead-II acetate. 21 g of calcium hydroxide are added at a uniform rate in the course of 6 hours so that the pH of the reaction mixture drops from 9.3 to 6.8. The solution, which is only slightly yellowish in color, is filtered. Only 0.5 g of an insoluble mixture of calcium formate and calcium carbonate is thereby removed. This means that more than 98% of the calcium ions are kept in solution by complex formation.

When the formose solution is concentrated by evaporation in a thin layer evaporator at 50° C. and 18 Torr, a yellowish sugar mixture is obtained containing 38% of reducing polyhydroxyaldehydes and polyhydroxyketones, calculated as glucose.

The relatively low proportion of reducing sugars is attributable to the crossed Cannizzaro reactions which take place to a considerable extent when calcium hydroxide is used as formose catalyst.

EXAMPLE 18

Several parallel experiments are carried out as described in Example 5(a) but the formation of formose is carried out at 80° C. with 100 g of a 70% solution of the cocatalyst indicated there. Although process gas containing formaldehyde is fed in at the rate of 416 liters per hour, 95% of formaldehyde is absorbed and converted into formose-sugar mixtures in spite of the unfavorable conditions of the apparatus (no scrubbing with countercurrent). When approximately 101 g of formaldehyde has been absorbed in the absorption liquid with the formation of formose or of hemiacetals and methylene glycol, the reaction is stopped at a residual formaldehyde content of 8.76% by weight and any formaldehyde which has not been converted into formoses is bound by various compounds which are capable of N-methylolation. For this purpose, 341 parts by weight of the formose solutions containing 8.76% by weight of formaldehyde are reacted in each case with the following aminoplast monomers:

(a) 60 parts by weight of urea,
(b) 35.5 parts by weight of thiourea,
(c) 42 parts by weight of dicyandiamide,
(d) 37.5 parts by weight of

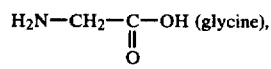

(e) 74 parts by weight of a diurethane having the following constitution:

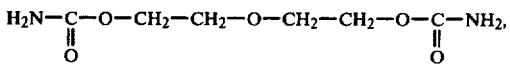

(f) 21 parts by weight of melamine,
(g) 113 parts by weight of ε-caprolactam,
(h) 85 parts by weight of pyrrolidone-(2),
(i) 93 parts by weight of aniline,
(j) 45 parts by weight of ethylamine,
(k) 11.3 parts by weight of ammonia,
(l) 105 parts by weight of diethanolamine.

In variations (a) to (h), the reaction with formaldehyde is carried out at 50° C. for one hour in the presence of 0.5% by weight of potassium carbonate as catalyst. When aniline, ethylamine, diethanolamine and ammonia are used as reactants, no catalysts are added since aminal formation, hexahydrotriazine formation and hexamethylene tetramine formation take place virtually spontaneously. Mixtures of formoses with oligomeric aminoplast condensates are obtained in all cases (a) to (l). After dehydration to water contents of 8%, the methylolated aminoplast formers either remain in solution in high concentrations in the formoses or undergo etherification reactions with the hydroxyl groups of the formoses. They may be foamed up with polyisocyanates to produce surprisingly flame-resistant open celled polyurethane-polyurea foams. The following polyisocyanates are preferred for this purpose: Polyisocyanates which have been obtained by the phosgenation of aniline-formaldehyde condensates; solutions of biuret- and allophanate-polyisocyanates of tolylene diisocyanates in monomeric tolylene diisocyanates and tolylene diisocyanates which contain isocyanurate groups, dissolved in monomeric tolylene diisocyanates having viscosities of from 105 mPas to 8500 mPas/20° C. The reaction of these formose-aminoplast monomer mixtures with polyisocyanates is advantageously carried out with the addition of from 10 to 20% by weight of elasticizing polyhydroxypolyethers or polyhydroxypolyesters, based on the quantity of formose-aminoplast mixture put into the process.

EXAMPLE 19

The procedure is exactly the same as in Example 18 but the 8.76% by weight of free formaldehyde is bound by reacting in each case 341 g of formose solution with the following ketones and aldehydes:

(a) 0.5 mol of cyclohexanone,
(b) 0.5 mol of cyclopentanone,
(c) 1 mol of isobutyraldehyde,
(d) 0.5 mol of butyraldehyde,
(e) 0.5 mol of methyl ethyl ketone,
(f) 0.5 mol of acetone.

The aldehydes and ketones added are methylolated in the α-position to the carbonyl group by heating with formaldehyde for 2 hours at 50° C. in the presence of 0.5 g of potassium carbonate as catalyst. Dehydration of reaction mixtures (a) to (f) in a thin layer evaporator at 50° C. and 18 Torr yields mixtures of formoses and the methylolated ketones and aldehydes. Compared with unmodified formoses, products (a) to (f) obtained by the process are more readily emulsifiable in higher molecular weight polypropylene glycol polyethers (OH number approximately 30 to 110) and have a substantially reduced viscosity at 30° C.: Viscosity of the initial formose containing 4% by weight of water: 110,000 mPas/30° C.;

Viscosity of (a): 67,000 mPas/30° C. at 4% water content.

Viscosity of (e): 58,000 mPas/30° C. at 4% water content.

EXAMPLE 20

The procedure is the same as described in Example 18 but the free formaldehyde is bound by the reaction of 341 g of formose solution with the following phenoplast monomers:

(a) 1 mol of phenol,
(b) 1 mol of resorcinol,
(c) 1 mol of cresol.

The phenols added are methylolated by the formaldehyde in the presence of 0.5 g of potassium carbonate as catalyst. When the reaction products are dehydrated in a thin layer evaporator at 55° C. and 18 Torr with the addition of phosphoric acid as catalyst, the aldehyde and keto groups of the formoses undergo condensation reactions with the partially methylolated phenols to produce highly viscous resins.

When CH-acidic compounds such as malonic acid esters or cyanoacetic acid esters are used in proportions of 0.2 mol, based on 1 mol of phenol, mixed condensates are obtained which can be emulsified in polyhydroxypolyethers having an average molecular weight of 2000 obtained from propylene oxide alone or propylene oxide and ethylene oxide (4:1), using 1 part by weight of the emulsifier represented by the following formula:

$$C_4H_9-O-CH_2-CH_2-(O-CH_2-CH_2)_{\overline{x}}-OH$$

$\overline{x}=20$.

EXAMPLE 21

(a) The procedure is the same as described in Example 5(a) but the absorption liquid used is a 24% aqueous solution of floral honey (N content of honey 0.04%). 213 Liters of formaldehyde-containing process gas (51 g of formaldehyde) having the composition indicated in Example 1 are passed through 250 g of this absorption liquid per hour at 99° C. The formose catalyst used is a pulverulent calcium hydroxide which is continuously added over a period of 106 minutes to maintain the pH of the reaction mixture at 7.3 to 7.5. The total quantity added is 12.5 g. After 106 minutes, approximately 91 g of formaldehyde have been absorbed. The introduction of process gas is then stopped. The reaction mixture, which still contains 16 g of unreacted formaldehyde, is then cooled (conversion: approximately 82%, based on the quantity of absorbed formaldehyde). On dehydration of the filtered formose solution, a pale yellow product mixture is obtained. The dehydrated product mixture (yield: 157 g; $H_2O$ content: 3% by weight) contains approximately 22 g of sparingly soluble calcium formate (14.1% by weight, based on the total yield) which will not crystallize even after prolonged storage. Owing to the use of calcium hydroxide as formose catalyst, crossed Cannizzaro reactions of the formose sugar mixtures with free formaldehyde take place as well as aldol condensations, so that the end product contains only 14.8% of reducing sugars, calculated as glucose.

(b) The procedure is the same as described under (a) but the reaction is carried out in the presence of 70 ml of a commercial basic ion exchanger in the form of beads. The polystyrene matrix of the exchanger, which has been crosslinked with divinylbenzene, contains 190 milliequivalents per 100 g of strongly basic groups having the following constitution:

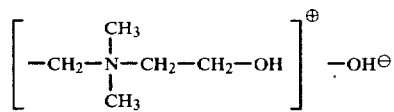

By this measure, the quantity of calcium hydroxide can be reduced to 7.5 parts by weight while keeping to the same pH values during the reaction because the formic acid formed by the crossed Cannizzaro reaction is fixed to the ion exchanger with neutralization. Yield of crude formose: 147 g, water content: 3.5% by weight.

(c) The procedure is the same as described under (b) but with different pH control and a different absorption liquid. 250 g of a completely desalted 30% formose solution having the molecular composition indicated for absorption liquid I (Example 1) are used as cocatalytically active absorption liquid. The pH is adjusted to 6.3-6.5 during the reaction by the addition of calcium hydroxide (a total of 4.5 g of catalyst is added). The introduction of process gas is stopped after 106 minutes and the reaction mixture is then maintained at 99° C. for 5 hours. Yield: 145 g; water content 3.8%.

The crossed Cannizzaro reaction is suppressed by using a different pH control than that of embodiment (a). The sugar component which has a reducing action therefore amounts to 31.7%.

EXAMPLE 22

The procedure is the same as in embodiment (a) of Example 21 but the absorption liquid I from Example 1 (250 g) concentrated to 30% is used as cocatalyst. The temperature during absorption of formaldehyde from the process gases is maintained at 50° C. by cooling. 4 g of Ca(OH)$_2$ are added in the course of 106 minutes so that the pH of the absorption solution drops from 10.1 to 8.5. The supply of process gas is then stopped and a further 5 g of calcium hydroxide are added portion wise at a temperature of 50° C. in the course of 5 hours so that the reaction mixture is adjusted to a pH of from 8.4 to 8.2. At that stage, the reaction product still contains 31 g of free formaldehyde. The crude formose solution is filtered and then dehydrated at pH 6.5 and 60° C. in a rotary evaporator under a vacuum of 16 Torr. 145 g of a pale yellowish product are obtained. Water content 3.5%. The crude formose, which contains approximately 6.5% by weight of calcium formate in solution, has a reducing sugar content of 45%.

Since dehydration under vacuum removes only about 3.5 g of the unreacted formaldehyde, the end product still contains about 27 g of formaldehyde bound by hemiacetal formation to the hydroxyl groups of the formose-sugar mixtures. The resulting product mixture containing hemiacetal groups has a powerful disinfectant, bactericidal and fungicidal activity, for example on biomasses of biological clarification plants which are in the process of cell division, and it prevents decomposition and decay processes in dried high protein biomasses, which would otherwise give rise to unpleasant odors.

EXAMPLE 23

Modification of Formose With Diethylphosphite (a) The procedure is as described in Example 5(a) but the formation of formose is carried out at 80° C. with 250 g of a 70% aqueous solution of the cocatalyst indicated in the said example. When, after expiry of two hours, 100 g of formaldehyde have been absorbed in the absorption liquid with the formation of formoses or of hemiacetals of formoses and methylene glycol, the condensation reaction is stopped at a residual formaldehyde content of 8% by weight, and any formaldehyde which has not been converted into formoses is bound by the formation of hydroxymethylphosphonic acid diethyl ester.

For this purpose, 341 g of the formose solution which contains 8% by weight of formaldehyde, amounting to a total formaldehyde content of about 27.3 g (0.9 mol) are first completely dehydrated and mixed with 137.9 g (1 mol) of diethylphosphite with stirring at room temperature for 8 hours in the presence of 2 g of triethylamine as catalyst.

Hydroxymethylphosphonic acid diethylester and various α-hydroxymethylphosphonic acid esters of formose are thereby formed due to the high reactivity of formaldehyde. A surprisingly low viscosity mixture, having a viscosity of only 670 mPas at 20° C. (viscosity of unmodified formose: 108,000 mPas/20° C.) is obtained in a yield of 412 g. When this mixture is heated to 50° C. in a vacuum, ethanol is split off. This is due to the fact that hydroxymethylphosphonic acid methyl ester and free diethylphosphite surprisingly readily undergo trans-esterification reactions with the hydroxyl groups of the formoses.

The extremely low viscosity of the modified formoses and the miscibility of these formoses with other polyols greatly facilitate foaming reactions with polyisocyanates and lend considerable interest to the products of the process as components with flame resistant properties which can be built into the reaction products in the diisocyanate polyaddition process.

(b) 412 g of the anhydrous mixture described under (a) are heated to 50° C. at 14 Torr. The molecular rearrangement and transesterification reactions mentioned above take place under these conditions, accompanied by elimination of alcohol. Approximately 45 g of ethanol are distilled off in the course of 2 hours, during which the viscosity of the mixture continuously rises. After removal by distillation of 1 mol of alcohol, the viscosity rises to approximately 9000 mPas at 20° C., and when a total of 1.5 mol of ethyl alcohol has been split off a viscosity of 16,500 mPas at 20° C. is reached.

(c) The procedure is the same as described under (a) but condensation is continued until it has been completed, and the formoses obtained, which are substantially free from formaldehyde, are reacted with 855 g (approximately 6.2 mol) of diethylphosphite as described under (b), this reaction being accompanied by trans-esterification. When 6 mol of ethanol have been split off, low viscosity mixtures are obtained in which the formoses originally put into the process have been almost quantitatively esterified with diethylphosphite to mixed esters. Such mixed esters which have the following idealized constitution

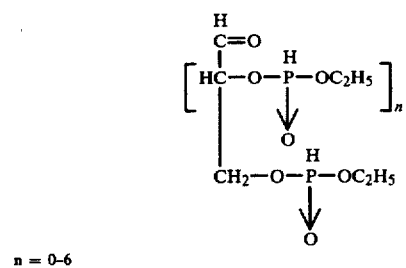

n = 0-6 are miscible with tolylene diisocyanate either on their own or as mixtures with free diethylphosphite.

EXAMPLE 24

This example describes acetalization reactions in formose mixtures which still contain formaldehyde. Formose-formaldehyde full acetals which are free from formaldehyde are thereby obtained by intermolecular or intramolecular full acetal formations. The products obtained consist mainly of mixtures of compounds having the following idealized constitutions:

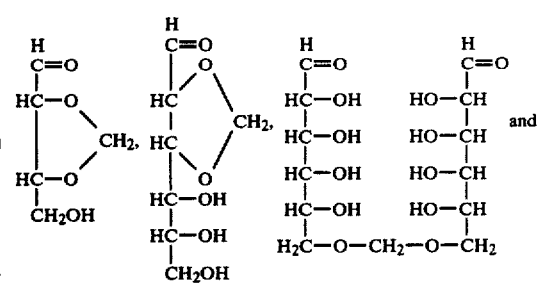

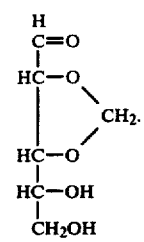

To carry out these reactions, the procedure is initially the same as described in Example 5a but formose formation is carried out at 80° C. with 250 g of a 70% solution of the cocatalyst indicated there. When 100 g of formaldehyde have been absorbed in the absorption liquid in the course of 2 hours with the formation of formoses or of hemiacetals of formoses and methylene glycol, formose formation is stopped at a residual formaldehyde content of approximately 8% by weight.

0.5 g of boric acid and 0.1 g of orthophosphoric acid are added to the formaldehyde-containing formose solution which is then completely dehydrated in a rotary evaporator at pH 2 in the course of 3 hours. The formaldehyde reacts quantitatively with the formoses to form whole acetals. 258 g of an anhydrous acetal mixture are obtained.

EXAMPLE 25

This example describes, in variations (a) to (c), the controlled aldolization of formose-sugar mixtures in the α-position to the carbonyl groups, formose-sugar mixtures being thereby obtained which have an average of at least two primary hydroxyl groups per molecule and are more reactive with polyisocyanates than the formoses originally present. It is interesting to find that this measure has the additional effect of substantially lowering the viscosity of the formoses.

(a) 400 g of a completely desalted aqueous solution containing 48% by weight of formoses, which solution has been prepared by the continuous method according to Example 1 (approximately 192 g of formose solid content) are mixed with 100 g of a 30% formalin solution (1 mol) and 6 g of triethylamine. The mixture is heated to 80° C. with stirring and the reduction in formaldehyde content is registered by titration with sodium sulphite. After only 45 minutes, the formaldehyde content in the solution has dropped from 6% to 0.5% and α-aldolization is completed. The hot solution is clarified by the addition of 8 g of active charcoal and filtered. The solution thus obtained was only a light yellowish tinge and contains, inter alia, α-aldolized formoses having the following idealized constitutions:

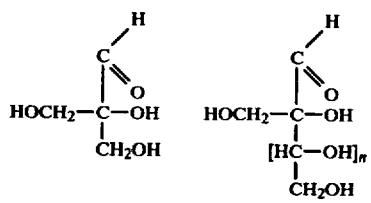

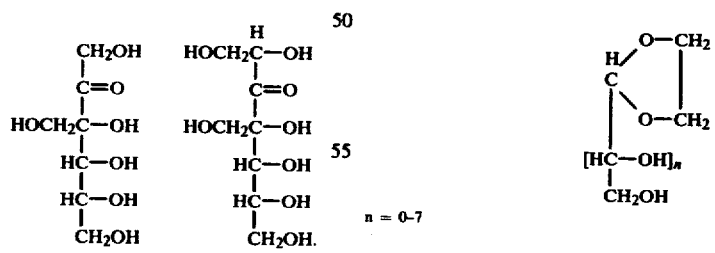

n = 1-7

After dehydration of these α-aldolized formoses to a water content of 2.9% in a rotary evaporator at 60° C. and 16 Torr, 229 g of a pale yellow aldolized formose syrup are obtained. This syrup has a viscosity of only 6500 mPas at 55° C. whereas the original formoses have a viscosity at the same water content of 16,500 mPas at 55° C.

It is surprisingly found that when the procedure is carried out as described above, α-aldolization occurs very much is preference to any possible crossed Cannizzaro reactions. Analytically determined triethyl ammonium formate formation indicates that only 1.8 g of the formaldehyde put into the process (approximately 6% of the total quantity) enters into Cannizzaro or crossed Cannizzaro reactions.

(b) The procedure is as described under (a) but triethylamine is replaced by 7 g of tri-n-propylamine. It is found that quantitative α-aldolization is terminated after only 35 minutes at 95° C.

(c) The procedure is the same as described under (a) but triethylamine is replaced by 5 g of dihydroxyethyl cyclohexylamine. It is found that quantitative α-aldolization is completed after about 42 minutes at 95° C.

The α-aldolized formoses prepared according to variations (a) to (c) are particularly interesting for the production of rigid polyurethane foams on account of the high proportion of primary alcoholic groups contained in them (approximately two primary OH equivalents at an average molecular weight of about 195) and their low viscosity. Extremely low viscosity solutions can be prepared by mixing these α-aldolized formoses with diethyl phosphite in a proportion by weight of 2:1 by the method described in Example 23.

EXAMPLE 26

This example describes the partial acetalization and ketalization of the carbonyl groups of formoses with ethylene glycol. The following method is employed:

400 g of the 48% aqueous solution of crude formose from Example 1, which has not been desalted and which contains about 192 g of sugar mixtures in which the proportion of reducing sugars is approximately 71%, are mixed with 47 g (approximately 0.76 mol) of ethylene glycol and concentrated to a residual water content of 2.5% by weight by evaporation in a thin layer evaporator at 60° C. and 18 Torr in the presence of 0.5 g of boric acid and 0.2 g of phosphoric acid as catalyst. Dehydration under these conditions is accompanied by acetalization of the formoses; it may be assumed that preferential formation of the 5-membered dioxolan derivatives having the following idealized constitution takes place:

$$\begin{array}{c} H \diagup\!\!\!{}^{O-CH_2} \\ C \\ \diagdown\!\!\!{}_{O-CH_2} \\ [HC-OH]_n \\ | \\ CH_2OH \end{array}$$

n = 0-7

Yield: 239 g.

Acetalization causes the reducing sugar component in the product mixture to drop to 12.5%, based on glucose. The acetalized formose has a viscosity of only 8700 mPas at 55° C., compared with 16,500 mPas of the original formose. Due to this low viscosity, the acetal and ketal mixtures of this example are more easily miscible or emulsifiable with hydroxypolyethers and hydroxypolyesters.

EXAMPLE 27

This example describes the use of formose-sugar mixtures prepared according to the invention as active cocatalysts for the discontinuous preparation of formoses from 37% by weight aqueous formalin solutions by the process according to German Offenlegungsschrift 2,639,084.

30,000 g of a 37% aqueous formaldehyde solution (370 mol of formaldehyde) are heated to 90° C. 145 g of lead-II acetate as catalyst and 1500 g of the 48% formose solution from Example 1 are added as cocatalyst at this temperature. The mixture is heated to 95° C. with vigorous stirring. When this temperature is reached, the supply of heat is removed. During the following 5 minutes, the pH of the solution is adjusted to 6.5 by the addition of approximately 2000 g of 10% sodium hydroxide solution. The reaction temperature rises to 98°–99° C. in the course of the exothermic reaction which sets in at once, and the reaction mixture begins to boil. The pH is maintained at 6.5 by continuous dropwise addition of NaOH solution until 30% conversion is reached (formaldehyde content of the reaction mixture: 23.6%). The supply of NaOH is then stopped, and the pH of the mixture slowly falls. When the pH has dropped to 5.7, the reaction mixture, which continues to boil gently, is maintained at this pH by dropwise addition of a further 700 g of 10% sodium hydroxide solution. The formaldehyde content drops to 14% after 20 minutes, to 12% after 35 minutes and to 8% after 40 minutes. After a further 10 minutes, the reaction mixture only contains 0.9% of formaldehyde.

Complete desalting followed by dehydration of the resulting formose solution in a thin layer evaporator at 60° C. and 18 Torr results in 12,700 g of a light yellow formose syrup. The viscosity of this formose syrup, which contains 8.4% by weight of water, is 83,400 mPas at 20° C.

EXAMPLE 28

This example describes the catalytic hydrogenation of formose-sugar mixtures which have been prepared according to the invention. 80 g of Raney nickel are added to 3500 g of the 48% aqueous formose solution according to Example 1, which is free from lead and completely desalted. The solution is hydrogenated at a hydrogen pressure of 200 kp/cm$^2$ and initially at room temperature until no more hydrogen is taken up. The temperature is then slowly raised in several steps to 160° C. and hydrogenation is carried to completion. Hydrogenation is completed after a total hydrogenation time of 6 to 10 hours. After filtration to remove the catalyst, a clear, colorless solution is obtained, from which 1700 g of a viscous mixture of polyhydric alcohols are obtained by concentration under vacuum. The mixture is colorless, in active towards Fehling's solution and does not turn brown when boiled with alkalies.

According to gas chromatographic analysis, the formite mixture has the following molecular distribution after silylation:

$C_2$ fraction: 1.58% by weight
$C_3$ fraction: 2.29% by weight
$C_4$ fraction: 4.23% by weight
$C_5$ fraction: 12.98% by weight
$C_6$ fraction: 45.96% by weight
$C_7$ and higher molecular weight fractions: 32.96% by weight.

The formite contains a total of 46% by weight of hydroxyl groups.

(a) 140 g of the formite are trans-esterified with 630 g of methyl stearate in 1200 g of dimethylformamide in the presence of 15 g of sodium methylate at 100° C. and 180 Torr until no more methanol is split off. A waxy mass is obtained after removal of the dimethyl formamide by distillation. This mass is freed from unesterified formite by treatment with hot water. The aqueous slurry is pressed off to remove excess water and dried under vacuum. A white, waxy mass which has good surface active properties is obtained.

(b) 140 g of the formite are reacted portionwise with 290 g of molten stearyl isocyanate at 110° C. in the presence of 0.8 g of triethylene diamine as catalyst to form a formite-stearyl urethane having free hydroxyl groups. After a reaction time of one hour, the reaction mixture is cooled. A waxy product having good emulsification properties is obtained.

(c) 112 g of the formite are quantitatively acetylated in the course of 2 hours with 408 g of acetic acid anhydride (4 mol), i.e. using about 1 mol of excess acetic acid anhydride, at 120° C. in the presence of 0.6 g of sodium acetate as catalyst. After removal of the acetic acid formed in the reaction and of unreacted acetic acid anhydride, a polyacetal-formite mixture is obtained in a yield of 280 g. This mixture may be used as plasticizer for synthetic resins, particularly for flexible and rigid polyurethane foams, with interesting elasticizing properties.

EXAMPLE 29

The unreduced dehydrated formose from Example 1 is acetylated as described in Example (28c). Modified formoses are obtained in which the cyclohemiacetal groups of the sugar mixtures are completely acetylated and open chain aldoses have been converted into acylals on their aldehyde groups in accordance with the following idealized formula:

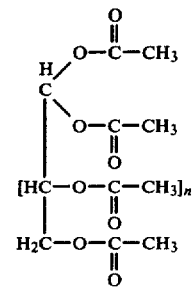

n = 0–7.

The acetyl groups which are bound as acylals saponify in the presence of water even at room temperature whereas the ester groups are not hydrolyzed under these conditions.

EXAMPLE 30

159 g of acrylonitrile (3 mol) are added dropwise at 90° C. to a mixture of 112 g of a crude formose which has been prepared by the continuous method described in Example 1. The formose is used desalted and has been dehydrated to a water content of 2.8% by weight of water. 0.5 g of potassium carbonate as catalyst are also added. A brownish colored cyanoethylated formite syrup is obtained in a yield of 270 g.

EXAMPLE 31

Use of the formoses according to the invention for the preparation of hydroxyl containing formose-phenoplast precondensates which have a disinfectant and germ-killing action.

400 g of the 48% aqueous crude formose solution according to Example 1 are condensed with 143 g of phenol (approximately 1.52 mol) in the presence of 0.5 g of concentrated sulphuric acid and 0.8 g of boric acid as condensation catalyst be heating at 100° C. for 5 hours. Water and small quantities of unreacted phenol are then removed, first at 60° C./18 Torr and then at 90° C./14 Torr. The sulphuric acid is neutralized by the addition of 10% sodium hydroxide solution and the condensation mixture is completely dehydrated by further heating under vacuum at 100° C. and 14 Torr. 315 g of a highly viscous brown resin consisting of phenol-formose condensates having the following idealized constitution

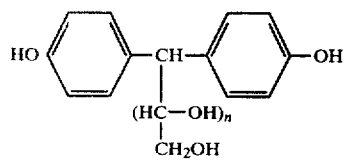

(n = 0-7)

and branched chain phenol-formose condensates in addition to approximately 25% by weight of formites present in the original formose mixture are obtained.

The condensate obtained is soluble in water due to the numerous hydroxyl groups in the formose residue. It has a powerful disinfecting action on biomasses of biological clarification plants. When 5 parts by weight of the 50% condensate solution are added to 30 parts by weight of a mycelial biomass which is in the process of cell division, cell death occurs and putrefaction processes of the dried, protein-rich biomasses, causing unpleasant, strong odors, are prevented.

EXAMPLE 32

Use of formoses prepared according to the invention for the Maillard reaction.

400 g of the 48% aqueous formose solution from Example 1, which has optionally been desalted, are reacted with (a) 60 g of urea and 37.5 g of aminoacetic acid (0.5 mol), (b) 93 g of aniline and 4.6 g of formic acid (0.1 mol)

for 8 hours at 100° C. with stirring. Condensation, dehydration and complicated rearrangement reactions take place with the formation of unsaturated sugars and continuous deepening of the color to form brownish red reaction products. After dehydration of the reaction products in a rotary evaporator at 70° C. and 18 Torr, highly viscous formose-Maillard conversion products having a reddish-brown color are obtained in both cases (a) and (b).

They are eminently suitable for the production of open celled rigid polyurethane-polyurea foams with high flame resistance. They are also excellent tanning agents.

EXAMPLE 33

This example describes the preparation of alkoxylated formose mixtures by the addition reaction of propylene oxide on OH groups of the formoses in the presence of Lewis catalysts.

1200 g of the completely desalted aqueous solution obtained according to Example 1, containing 48% by weight of formose and having a reducing sugar content of 71%, are dehydrated to a water content of 2.9% by weight in a rotary evaporator under a vacuum at 60° C. (viscosity: 108,000 mPas/35° C.). In variations (a) to (c), 0.5 g of a complex of 1 mol of boron trifluoride and 1 mol of acetic acid (BF$_3$.CH$_3$COOH) is then slowly stirred at room temperature into 100 g of the resulting formose syrup under a nitrogen atmosphere. Reaction mixtures (a) to (c) are vigorously stirred under a nitrogen atmosphere and the following quantities of propylene oxide are added dropwise, slowly and at a uniform rate, over a period of 2 hours at 49° C.:

(a) 58 g of propylene oxide (1 mol)
(b) 87 g of propylene oxide (1.5 mol)
(c) 116 g of propylene oxide (2 mol).

After neutralization with small quantities of sodium hydroxide solution or 25% aqueous ammonia solution, reaction mixtures (a) to (c) are freed from traces of propylene oxide and small quantities of water at 50° C. The viscosity and the proportion of reducing sugar component in the resulting formosepolyether are surprisingly low.

(a) Yield: 156 g; viscosity: 26,000 mPas at 35° C.; reducing sugar component in the polyether: 19.8%, calculated as glucose.

This sharp drop in the proportion of reducing sugar component when propoxylation is carried out shows that a considerable proportion of the carbonyl groups in the formoses had been acetalized or ketalized, presumably primarily by ring opening addition of propylene oxide to 1,3-dioxolan derivatives.

(b) Yield: 182 g; viscosity of the polyether at 35° C.: 16,840 mPas; proportion of sugar which has a reducing action: 14.6%, based on glucose.

(c) Yield: 208 g, viscosity of the polyether at 35° C.: 5772 mPas; proportion of sugar component with reducing action: 12.2%, based on glucose. The OH number of the polyether is 495, the acid number 0.6%.

All the polyether mixtures (a) to (c) are more compatible than dehydrated crude formoses with both high molecular weight and low molecular weight polyhydroxyl compounds as well as with isocyanates. Another important feature is that the polyethers obtained according to (a) to (c) are considerably more reactive with polyisocyanates than the formose polyethers conventionally prepared by OH$^\ominus$ catalysis in the presence of sodium hydroxide solution or potassium hydroxide solution. Polyaddition of propylene oxide to formose catalyzed with Lewis acids appears to take place fairly selectively in accordance with the following reaction scheme:

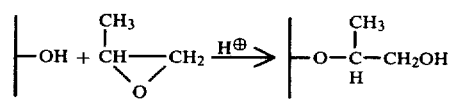

This leads to primary hydroxyl groups whereas polyaddition catalyzed with bases leads statistically and consequently to at least 50% of secondary hydroxyl groups being present in the polyether. Moreover, the $OH^{\ominus}$ catalyzed reaction results in dark colored products and is accompanied by decomposition reactions of the formoses.

Rigid to semirigid polyurethane foams can be produced from polyether mixtures (a) to (c) by means of known formulations and methods.

Polyaddition of 1500 parts by weight of propylene oxide to 100 parts by weight of formose by a method analogous to (c) in the presence of increased quantities of $BF_3$-acetate results in polyethers with OH numbers in the range of 56 to 60 which are very suitable for the production of flexible foams.

EXAMPLE 34

Use of formoses prepared according to the invention and their modification products as starting components for the production of flame-resistant polyurethane foams.

(a) 128 g of urea (2.13 mol) are dissolved in 400 g of the 48% crude formose prepared by the continuous method according to Example 1. The formose may have been desalted and is almost free from formaldehyde. The solution is concentrated to a solid content of 85% by weight (solution A) by evaporation in a rotary evaporator under vacuum.

57 Parts by weight of solution A, containing approximately 29,3% by weight of formose, 20 parts by weight of urea and 8,3 parts by weight of water, are mixed at 35° C. with 20 parts by weight of a propylene oxide-ethylene oxide mixed polyether with OH number 28 which has been started on trimethylolpropane. The polyether contains 0.6 parts by weight of an emulsifier having the following constitution:

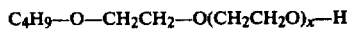

$C_4H_9$—O—$CH_2CH_2$—O$(CH_2CH_2O)_x$—H (x = average 20)

1.2 Parts by weight of a commercial silicone stabilizer (stabilizer OS 610 of Bayer AG), 0.2 parts by weight of endoethylenepiperazine and 0.25 parts by weight of tin-(II) octoate are added to the vigorously stirred mixture, and 127 parts by weight of a phosgenation product of a commercial aniline-formaldehyde condensate mixture are then stirred in. The polyisocyanate used has an isocyanate content of 29%. Foaming begins within a short time, proceeds completely trouble-free and is completed after 5 minutes. An open celled rigid foam containing urea and biuret groups and having a unit weight of 27.5 kg/m$^3$ is obtained.

In spite of the high water content in the formulation, no discoloration is found at the center of the finished foam.

The foam is completely free from any undesirable odor of caramel. Taking into account all the NCO, OH and NH$_2$ equivalents used (including the water added), the rigid foam is calculated to have been produced with an index of about 45. When the rigid foam is cut up into strips measuring 2 cm $\times$ 1 cm $\times$ 10 cm, the strips cannot be ignited by the flame of a bunsen burner, and the speed of propagation of the flame is therefore zero. Moreover, no spread of flame can be obtained by exposing the strip to a bunsen flame for over 30 seconds; combustion consists merely of carbonization of the foam with liberation of gases of combustion with a high water content.

(b) The same procedure is employed as described under (a) but 5 parts by weight of an association of 1 mol of propylene glycol and 1 mol of $\epsilon$-caprolactam are added to the polyol mixture as active catalyst for the blowing reaction. A rigid, open celled foam is obtained as described under (a). Foam formation is completed after only 4 minutes and the foam obtained has a unit weight of 25 kg/m$^3$. The flame resistance of the foam is equal to that of the product described under (a).

(c) The procedure is the same as described under (a) but 2 parts by weight of $\epsilon$-caprolactam are added for more powerful activation of the isocyanate/water reaction. The quantity of polyisocyanate introduced is increased to 244 parts by weight. The process is therefore carried out at an index of approximately 90. The rigid foam obtained does not have the same high flame resistance as the foam produced under (a) but it does have the tendency to self-extinguishing after it has been ignited.

(d) The procedure is the same as described under (a) but the formoses is replaced by an equal quantity of the formose which has been aldolized with formaldehyde in the $\alpha$-position to the carbonyl groups as described in Example 25. Since this $\alpha$-aldolized formose has at least two primary hydroxyl groups per molecule, the foaming process proceeds 1.5 times more rapidly at the same catalyst concentration, as measured by the rise time. When foamed at an index of 45, the rigid foam obtained is just as flame resistant as the product described under (a).

The high flame resistance of elasticized rigid foams produced at low indices as described under (a), (b) and (d) is presumably due to the formation of water of dehydration as well as to the water formed by condensation of the carbonyl groups of the formose with urea during the combustion process.

(e) The procedure described under (a) is repeated but the formose content in the formulation is replaced by 55 parts by weight of the following modified formoses:

($e^1$) formose according to Example 8(f) (modification with methylolated cyclohexanone), ($e^2$) formose according to Example 18(c) (dicyandiamide modification), ($e^3$) formose according to Example 18(f) (melamine modification), ($e^4$) formose according to Example 23(a) (diethylphosphite modification), ($e^5$) formose according to Example 32(a) (Maillard modification), ($e^6$) formose according to Example 33(a) (propoxylated formose), ($e^7$) freshly prepared mixture of 33 parts by weight of formose, 36 parts by weight of diethylphosphite and 20 parts by weight of the elasticizing polyhydroxyl polyether described under (a).

Each of the modified formoses contains 7 parts by weight of water. The elasticized rigid foams obtained according to ($e^1$) to ($e^7$) are to a large extent open celled and have the following unit weights and fire characteristics:

| Example | Unit weight (kg/m$^3$) | Fire characteristics |
|---|---|---|
| $e^1$ | 30 | excellent flame resistance and tendency to carbonization as in Example 34 a) |
| $e^2$ | 27 | |
| $e^3$ | 29 | |
| $e^4$ | 25 | |
| $e^5$ | 24 | |

| Example | Unit weight (kg/m³) | Fire characteristics |
|---|---|---|
| e⁶ | 25 | less high flame resistance |
| e⁷ | 26 | high flame resistance and tendency to carbonization |

The reduced flame resistance of e⁶ is presumably due to the lower carbonyl group content of the reaction mixture.

EXAMPLE 35

Use of formose-polyethers for the production of substantially closed celled rigid foams.

A mixture of 100 parts by weight of the polyether prepared from formose and propylene oxide according to Example 33(c), containing a reducing sugar component of 12.2% and having an OH number of 495, 1.5 parts by weight of a commercial silicone stabilizer (stabilizer OS 610 of Bayer AG), 0.5 part by weight of endoethylene piperazine, 4.5 parts by weight of a liquid associate mixture of 2.5 parts by weight of ε-caprolactam and 2 parts by weight of water and 40 parts by weight of monofluorotrichloromethane is vigorously mixed with 152 parts by weight of a commercial phosgenation product of aniline-formaldehyde condensate (isocyanate content 29%). Rapid and uniform foam formation follows. The foam obtained has a unit weight of 37 kg/m³.

What is claimed is:

1. In a process for the preparation of cellular or non-cellular polyurethane resins by the reaction of
(a) polyisocyanates with
(b) compounds with a molecular weight of between 32 and 400 having at least two active hydrogen atoms, and optionally
(c) compounds with a molecular weight of between 400 and 10,000 having at least two active hydrogen atoms, and optionally
(d) blowing agents, catalysts and other known additives, the improvement which comprises using as component (b) products prepared by the condensation of formaldehyde in an aqueous reaction medium in the presence of metal compounds as catalysts and of compounds capable of enediol formation as cocatalysts, by introducing synthesis gases containing formaldehyde continuously or discontinuously at temperatures of between 10° and 150° C. into an absorption liquid comprising
(a) 5 to 99% by weight of water,
(b) 0.1 to 90% by weight of compounds capable of enediol formation as cocatalysts,
(c) 0 to 20% by weight of soluble or insoluble metal compounds as catalysts optionally bound to high molecular weight carriers, and
(d) 0 to 60% by weight of one or more monohydric or higher hydric low molecular weight alcohols and/or higher molecular weight polyhydroxyl compounds and having a pH of 3 to 10, and the formaldehyde being condensed at the same time or, if the absorption solution contains no catalyst, the formaldehyde being condensed by the addition of catalyst, stopping the condensation of formaldehyde with itself by cooling and/or by inactivation of the catalyst with acids in known manner when the reaction mixture has a residual formaldehyde content of from 0 to 10% by weight; removing the catalyst in known manner; and reducing the aldehyde and keto groups present in the reaction product to hydroxyl groups.

* * * * *